(12) United States Patent
Chilkoti et al.

(10) Patent No.: US 12,084,480 B2
(45) Date of Patent: *Sep. 10, 2024

(54) UNSTRUCTURED NON-REPETITIVE POLYPEPTIDES HAVING LCST BEHAVIOR

(71) Applicant: Duke University, Durham, NC (US)

(72) Inventors: Ashutosh Chilkoti, Durham, NC (US); Nicholas Tang, Durham, NC (US); Garrett Kelly, Durham, NC (US)

(73) Assignee: Duke University, Durham, NC (US)

( * ) Notice: Subject to any disclaimer, the term of this patent is extended or adjusted under 35 U.S.C. 154(b) by 66 days.

This patent is subject to a terminal disclaimer.

(21) Appl. No.: 17/477,192

(22) Filed: Sep. 16, 2021

(65) Prior Publication Data

US 2022/0098248 A1 Mar. 31, 2022

Related U.S. Application Data

(63) Continuation of application No. 16/335,734, filed as application No. PCT/US2017/052887 on Sep. 22, 2017, now Pat. No. 11,155,584.

(60) Provisional application No. 62/399,123, filed on Sep. 23, 2016.

(51) Int. Cl.
| | | |
|---|---|---|
| C07K 14/31 | (2006.01) | |
| A61K 38/00 | (2006.01) | |
| A61K 47/65 | (2017.01) | |
| G01N 33/68 | (2006.01) | |

(52) U.S. Cl.
CPC .............. *C07K 14/31* (2013.01); *A61K 47/65* (2017.08); *G01N 33/68* (2013.01); *A61K 38/00* (2013.01); *C07K 2319/02* (2013.01); *C07K 2319/21* (2013.01); *G01N 2800/52* (2013.01)

(58) Field of Classification Search
CPC ............... C07K 14/31; C07K 2319/02; C07K 2319/21; C07K 2319/00; C07K 14/00; A61K 47/65; A61K 38/00; G01N 33/68; G01N 2800/52; A61P 35/00
See application file for complete search history.

(56) References Cited

U.S. PATENT DOCUMENTS

| | | | |
|---|---|---|---|
| 4,415,732 A | 11/1983 | Caruthers et al. |
| 4,458,066 A | 7/1984 | Caruthers et al. |
| 4,500,707 A | 2/1985 | Caruthers et al. |
| 4,554,101 A | 11/1985 | Hopp |
| 4,668,777 A | 5/1987 | Caruthers et al. |
| 4,973,679 A | 11/1990 | Caruthers et al. |
| 4,976,734 A | 12/1990 | Urry et al. |
| 5,153,319 A | 10/1992 | Caruthers et al. |
| 5,250,516 A | 10/1993 | Urry |
| 5,278,302 A | 1/1994 | Caruthers et al. |
| 5,336,256 A | 8/1994 | Urry |
| 5,453,496 A | 9/1995 | Caruthers et al. |
| 5,534,408 A | 7/1996 | Green et al. |
| 5,578,577 A | 11/1996 | Ching et al. |
| 5,580,859 A | 12/1996 | Felgner et al. |
| 5,602,244 A | 2/1997 | Caruthers et al. |
| 5,676,646 A | 10/1997 | Hofmann et al. |
| 5,679,647 A | 10/1997 | Carson et al. |
| 5,702,359 A | 12/1997 | Hofmann et al. |
| 5,703,055 A | 12/1997 | Felgner et al. |
| 5,935,776 A | 8/1999 | Green et al. |
| 6,068,650 A | 5/2000 | Hofmann et al. |
| 6,096,020 A | 8/2000 | Hofmann |
| 6,120,493 A | 9/2000 | Hofmann |
| 6,150,148 A | 11/2000 | Nanda et al. |
| 6,181,964 B1 | 1/2001 | Hofmann et al. |
| 6,192,270 B1 | 2/2001 | Hofmann et al. |
| 6,207,749 B1 | 3/2001 | Mayes et al. |
| 6,208,893 B1 | 3/2001 | Hofmann |
| 6,216,034 B1 | 4/2001 | Hofmann et al. |
| 6,233,482 B1 | 5/2001 | Hofmann et al. |
| 6,241,701 B1 | 6/2001 | Hofmann |
| 6,245,515 B1 | 6/2001 | Vogelstein et al. |
| 6,296,831 B1 | 10/2001 | Weller et al. |
| 6,302,874 B1 | 10/2001 | Zhang et al. |
| 6,413,587 B1 | 7/2002 | Hawker et al. |
| 6,512,060 B1 | 1/2003 | Matyjaszewski et al. |
| 6,541,580 B1 | 4/2003 | Matyjaszewski et al. |
| 6,623,950 B1 | 9/2003 | Osten et al. |
| 6,649,138 B2 | 11/2003 | Adams et al. |
| 6,660,247 B1 | 12/2003 | Gutowska et al. |
| 6,841,617 B2 | 1/2005 | Jeong et al. |
| 6,852,834 B2 | 2/2005 | Chilkoti |
| 6,869,588 B2 | 3/2005 | Weller et al. |

(Continued)

FOREIGN PATENT DOCUMENTS

| | | | |
|---|---|---|---|
| AU | 2007265628 B2 | 12/2012 |
| CA | 2327325 A1 | 11/1999 |

(Continued)

OTHER PUBLICATIONS

Liu et al., "Stable Evans Blue Derived Exendin-4 Peptide for Type 2 Diabetes Treatment," Bioconjugate Chem, 2016, 27: 54058.

(Continued)

*Primary Examiner* — Marcela M Cordero Garcia

(74) *Attorney, Agent, or Firm* — Michael Best & Friedrich LLP

(57) ABSTRACT

Described herein are unstructured polypeptides lacking any discernible repeat motif. Also described herein are fusion proteins including at least one of the unstructured polypeptides and at least one binding polypeptide. Further described are methods for treating a disease in a subject in need thereof. The methods may include administering to the subject an effective amount of the fusion protein.

14 Claims, 6 Drawing Sheets

Specification includes a Sequence Listing.

(56) References Cited

U.S. PATENT DOCUMENTS

| | | | |
|---|---|---|---|
| 7,033,571 B2 | 4/2006 | Gutowska et al. |
| 7,087,244 B2 | 8/2006 | Jeong et al. |
| 7,300,922 B2 | 11/2007 | Sullenger et al. |
| 7,429,458 B2 | 9/2008 | Chilkoti |
| 7,531,524 B2 | 5/2009 | Rusconi |
| 7,664,545 B2 | 2/2010 | Westersten et al. |
| 7,674,882 B2 | 3/2010 | Kaplan et al. |
| 8,129,330 B2 | 3/2012 | Martinez et al. |
| 8,283,125 B2 | 10/2012 | Cebolla Ramirez et al. |
| 8,470,967 B2 | 6/2013 | Chilkoti et al. |
| 8,497,356 B2 | 7/2013 | Chilkoti et al. |
| 8,506,963 B2 | 8/2013 | Li et al. |
| 8,586,347 B2 | 11/2013 | Lochhead et al. |
| 8,841,414 B1 | 9/2014 | Raucher et al. |
| 8,912,310 B2 | 12/2014 | Chilkoti et al. |
| 8,937,153 B2 | 1/2015 | Abrahmsén et al. |
| 9,127,047 B2 | 9/2015 | Chilkoti |
| 9,132,178 B2 | 9/2015 | Philip |
| 9,138,743 B2 | 9/2015 | Yager et al. |
| 9,482,664 B2 | 11/2016 | Chilkoti et al. |
| 9,592,303 B2 | 3/2017 | Chilkoti et al. |
| 9,771,396 B2 | 9/2017 | Chilkoti et al. |
| 9,804,170 B2 | 10/2017 | Krishna et al. |
| 9,890,420 B2 | 2/2018 | Chilkoti et al. |
| 10,064,954 B2 | 9/2018 | Wu |
| 10,131,690 B2 | 11/2018 | Bonny et al. |
| 10,302,636 B2 | 5/2019 | Chilkoti et al. |
| 10,364,451 B2 | 7/2019 | Chilkoti et al. |
| 10,385,115 B2 | 8/2019 | Chilkoti et al. |
| 10,434,182 B2 | 10/2019 | Weng et al. |
| 2001/0034050 A1 | 10/2001 | Chilkoti |
| 2002/0052443 A1 | 5/2002 | Greenwald et al. |
| 2002/0146794 A1 | 10/2002 | Tomycz |
| 2003/0008308 A1 | 1/2003 | Enzelberger et al. |
| 2003/0138829 A1 | 7/2003 | Unger et al. |
| 2003/0175290 A1 | 9/2003 | Renner et al. |
| 2003/0185741 A1 | 10/2003 | Matyjaszewski et al. |
| 2003/0225251 A1 | 12/2003 | Sallberg et al. |
| 2003/0233675 A1 | 12/2003 | Cao et al. |
| 2004/0053976 A1 | 3/2004 | Martinez et al. |
| 2004/0101852 A1 | 5/2004 | Bennett et al. |
| 2004/0192072 A1 | 9/2004 | Snow et al. |
| 2005/0186214 A1 | 8/2005 | Liu et al. |
| 2005/0255554 A1 | 11/2005 | Chilkoti |
| 2005/0288229 A1 | 12/2005 | Sindrey et al. |
| 2006/0025524 A1 | 2/2006 | Schneider et al. |
| 2006/0034796 A1 | 2/2006 | Ashwell et al. |
| 2006/0051798 A1 | 3/2006 | Mirkin et al. |
| 2007/0087114 A1 | 4/2007 | Chilkoti et al. |
| 2007/0117173 A1 | 5/2007 | Levison et al. |
| 2008/0181861 A1 | 7/2008 | Jiang et al. |
| 2009/0098652 A1 | 4/2009 | Stupp et al. |
| 2009/0215194 A1 | 8/2009 | Magni et al. |
| 2009/0247424 A1 | 10/2009 | Chilkoti et al. |
| 2010/0015070 A1 | 1/2010 | Bollschweiler et al. |
| 2010/0022455 A1 | 1/2010 | Chilkoti |
| 2010/0048473 A1 | 2/2010 | Chaikof et al. |
| 2010/0120018 A1 | 5/2010 | Quake et al. |
| 2010/0241054 A1 | 9/2010 | Dacey et al. |
| 2010/0311059 A1 | 12/2010 | Didion et al. |
| 2010/0311669 A1 | 12/2010 | Greene et al. |
| 2010/0325765 P1 | 12/2010 | Pait et al. |
| 2011/0082283 A1 | 4/2011 | Dagher et al. |
| 2011/0119778 A1 | 5/2011 | Liss |
| 2011/0165557 A1 | 7/2011 | Ah et al. |
| 2011/0207673 A1 | 8/2011 | Chilkoti et al. |
| 2011/0248698 A1 | 10/2011 | Kikuchi et al. |
| 2011/0294189 A1 | 12/2011 | Chilkoti et al. |
| 2011/0303303 A1 | 12/2011 | Proper et al. |
| 2011/0305718 A1 | 12/2011 | Mugica et al. |
| 2012/0172298 A1 | 7/2012 | Andersen et al. |
| 2012/0208742 A1 | 8/2012 | Primiano et al. |
| 2013/0039927 A1 | 2/2013 | Dewhurst et al. |
| 2013/0079277 A1 | 3/2013 | Chilkoti |
| 2013/0079280 A1 | 3/2013 | Baca et al. |
| 2013/0096058 A1 | 4/2013 | Baca et al. |
| 2013/0102993 A1 | 4/2013 | Kim et al. |
| 2013/0130384 A1 | 5/2013 | Okamoto et al. |
| 2013/0157889 A1 | 6/2013 | Chilkoti et al. |
| 2013/0165389 A1 | 6/2013 | Schellenberger et al. |
| 2013/0172274 A1 | 7/2013 | Chilkoti |
| 2013/0197359 A1 | 8/2013 | Park et al. |
| 2013/0315823 A1 | 11/2013 | Trieu |
| 2013/0330335 A1 | 12/2013 | Bremel et al. |
| 2014/0024600 A1 | 1/2014 | Chilkoti et al. |
| 2014/0163201 A1 | 6/2014 | Winter et al. |
| 2014/0275227 A1 | 9/2014 | Hoge et al. |
| 2014/0294932 A1 | 10/2014 | Kim et al. |
| 2015/0094270 A1 | 4/2015 | Harris et al. |
| 2015/0099707 A1 | 4/2015 | Pastan et al. |
| 2015/0112022 A1 | 4/2015 | Chilkoti et al. |
| 2016/0017278 A1 | 1/2016 | Montclare et al. |
| 2016/0114053 A1 | 4/2016 | Chilkoti |
| 2016/0120952 A1 | 5/2016 | Chilkoti |
| 2016/0200787 A1 | 7/2016 | Matern et al. |
| 2016/0209356 A1 | 7/2016 | Herget et al. |
| 2016/0220727 A1 | 8/2016 | Lu et al. |
| 2016/0250165 A1 | 9/2016 | Sullenger et al. |
| 2016/0271262 A1 | 9/2016 | Lopez et al. |
| 2016/0303091 A1 | 10/2016 | Wang |
| 2016/0348147 A1 | 12/2016 | Lopez et al. |
| 2016/0355802 A1 | 12/2016 | Isaacs et al. |
| 2017/0088670 A1 | 3/2017 | Rowan et al. |
| 2017/0102357 A1 | 4/2017 | Liang et al. |
| 2017/0166621 A1 | 6/2017 | Boettcher et al. |
| 2017/0170142 A1 | 6/2017 | Edelstein et al. |
| 2017/0189545 A1 | 7/2017 | Lee et al. |
| 2017/0233714 A1 | 8/2017 | Chilkoti et al. |
| 2017/0239363 A1 | 8/2017 | Chilkoti et al. |
| 2017/0369651 A1 | 12/2017 | Cheng et al. |
| 2018/0037609 A1 | 2/2018 | Chilkoti et al. |
| 2018/0135060 A1 | 5/2018 | Romero Ramos et al. |
| 2018/0161772 A1 | 6/2018 | Rammohan et al. |
| 2018/0171337 A1 | 6/2018 | O'Neill et al. |
| 2018/0200196 A1 | 7/2018 | Fahmy et al. |
| 2018/0217136 A1 | 8/2018 | Chilkoti et al. |
| 2018/0231469 A1 | 8/2018 | Gibbons et al. |
| 2018/0238864 A1 | 8/2018 | Burd et al. |
| 2018/0258157 A1 | 9/2018 | Chilkoti et al. |
| 2018/0326044 A1 | 11/2018 | Carter |
| 2018/0327752 A1 | 11/2018 | Pillay et al. |
| 2018/0369399 A1 | 12/2018 | Hershfield et al. |
| 2019/0016763 A1 | 1/2019 | Kitazawa et al. |
| 2019/0204309 A1 | 7/2019 | Gibbs |
| 2019/0285623 A1 | 9/2019 | Chilkoti et al. |
| 2019/0292549 A1 | 9/2019 | Zhang et al. |
| 2019/0345228 A1 | 11/2019 | Chilkoti et al. |
| 2020/0078313 A1 | 3/2020 | Roy et al. |
| 2020/0121809 A1 | 4/2020 | Hope et al. |
| 2020/0148724 A1 | 5/2020 | Chilkoti et al. |
| 2020/0163878 A1 | 5/2020 | Baumhof et al. |
| 2020/0181555 A1 | 6/2020 | Hinojosa et al. |
| 2021/0128734 A1 | 5/2021 | Chilkoti et al. |
| 2021/0154143 A1 | 5/2021 | Chilkoti et al. |

FOREIGN PATENT DOCUMENTS

| | | |
|---|---|---|
| CA | 2423488 A1 | 4/2002 |
| CN | 104725628 B | 4/2018 |
| CN | 112961065 A | 6/2021 |
| EP | 1670315 B1 | 4/2017 |
| EP | 2664340 B1 | 2/2020 |
| JP | 2014-156428 A | 8/2014 |
| JP | 2014-534265 A | 12/2014 |
| WO | WO1991/019813 A1 | 12/1991 |
| WO | WO2003/040165 A2 | 10/2002 |
| WO | WO2004/096124 A2 | 11/2004 |
| WO | WO2006/004778 A2 | 1/2006 |
| WO | WO2006/110292 A2 | 10/2006 |
| WO | WO2007/073486 A2 | 6/2007 |
| WO | WO2007/108013 A2 | 9/2007 |
| WO | WO2007/134245 A2 | 11/2007 |
| WO | WO2008/012543 A1 | 1/2008 |
| WO | WO2008/030968 A2 | 3/2008 |

(56) References Cited

FOREIGN PATENT DOCUMENTS

| | | |
|---|---|---|
| WO | WO2009/067584 A1 | 5/2009 |
| WO | WO2010/054699 A1 | 5/2010 |
| WO | WO2010/057154 A1 | 5/2010 |
| WO | WO2010/096422 A1 | 8/2010 |
| WO | WO2011/025572 A1 | 3/2011 |
| WO | WO2011/123813 A2 | 10/2011 |
| WO | WO2012/162426 A1 | 11/2012 |
| WO | WO2013/049234 A2 | 4/2013 |
| WO | WO2013/065009 A1 | 5/2013 |
| WO | WO2013/106715 A1 | 7/2013 |
| WO | WO2014/037373 A1 | 3/2014 |
| WO | WO2014/194244 A1 | 12/2014 |
| WO | WO2015/011231 A1 | 1/2015 |
| WO | WO2015/130846 A2 | 9/2015 |
| WO | WO2016/065273 A1 | 4/2016 |
| WO | WO2016/065300 A1 | 4/2016 |
| WO | WO2016/090103 A1 | 6/2016 |
| WO | WO2016/154530 A1 | 9/2016 |
| WO | WO2017/015132 A1 | 1/2017 |
| WO | WO2017/024182 A1 | 2/2017 |
| WO | WO2017/112825 A2 | 6/2017 |
| WO | WO2017/112826 A2 | 6/2017 |
| WO | WO2017/192449 A1 | 11/2017 |
| WO | WO2018/115401 A1 | 6/2018 |
| WO | WO2018/144854 A1 | 8/2018 |
| WO | WO2019/103744 A1 | 5/2019 |
| WO | WO2019/147954 A1 | 8/2019 |
| WO | 2020/037100 A1 | 2/2020 |
| WO | WO2020/037214 A1 | 2/2020 |
| WO | 2020/051223 A1 | 3/2020 |
| WO | WO2020/160472 A1 | 8/2020 |
| WO | 2021/178898 A1 | 9/2021 |
| WO | 2022/016089 A2 | 1/2022 |
| WO | 2022/178438 A1 | 8/2022 |

OTHER PUBLICATIONS

United States Patent Office Notice of Allowance for U.S. Appl. No. 17/015,315 dated Apr. 26, 2023 (7 pages).
United States Patent Office Action for U.S. Appl. No. 17/051,202 dated Jun. 21, 2023 (10 pages).
AACR, "AACR Cancer Progress Report 2016," Clin Cancer Res, Oct. 2016, vol. 22, Issue 19, 143 pages.
Aaron et al., "Elastin as a Random-Network Elastomer—a Mechanical and Optical Analysis of Single Elastin Fibers," Biopolymers, 1981, 20(6):1247-1260.
Abbaspourrad et al., "Controlling release from pH-responsive microcapsules, " Langmuir, 2013, 29: 12697-12702.
Abbaspourrad et al., "Polymer microcapsules with programmable active release," J Am Chem Soc, 2013, 135: 7744-7750.
Abbruzzese et al., "A phase I clinical, plasma, and cellular pharmacology study of gemcitabine," J. Clin. Oncol. 1991, 3, 491-498.
Adams et al., "Safety and utilization of blood components as therapeutic delivery systems," Curr Pharm Biotechnol, 2003, 4(5): 275-82.
Adams et al., "Sustained release of antibiotics from injectable and thermally responsive polypeptide depots," J Biomed Mater Res B Appl Biomater, Jul. 2009, vol. 90B, Issue 1, pp. 67-74.
Adamska et al., "Pancreatic ductal adenocarcinoma: Current and evolving therapies," J Mol Sci, Jun. 2017, vol. 18, Issue 7, pp. 1338-1380.
Adiseshaiah et al., "Nanomedicine strategies to overcome the pathophysiological barriers of pancreatic cancer," Nat Rev Clin Oncol, Dec. 2016, vol. 13, Issue 12, pp. 750-765.
Agarwal et al., "One-step microfluidic generation of pre-hatching embryo-like core-shell microcapsules for miniaturized 3D culture of pluripotent stem cells," Lab Chip, 2013, 13: 4525-4533.
Ahmed et al., "Preliminary Identification of Potential Vaccine Targets for the COVID-19 Coronavirus (SARS-CoV-2) Based on SARS-CoV Immunological Studies," Viruses, 2020, 12:254, 15 pages.

Aladini et al., "Chemical Synthesis and Characterization of Elastin-Like Polypeptides (ELPs) With Variable Guest Residues," J Pept Sci, May 2016, vol. 22, Issue 5, pp. 334-342.
Alarcon et al., "Exendin 4 controls insulin production in rat islet beta cells predominantly by potentiation of glucose-stimulated proinsulin biosynthesis at the translational level," Diabetologia, 2006, 49(12):2920-2929.
Albanese et al., "The effect of nanoparticle size, shape, and surface chemistry on biological systems," Annu. Rev. Biomed. Eng., Aug. 2012, vol. 14, pp. 1-16.
Alconcel et al., "FDA-approved poly(ethylene glycol)-protein conjugate drugs," Polym. Chem., vol. 2, Apr. 2011, Issue 7, pp. 1442-1448.
Alghoul et al., "The effect of hyaluronan hydrogel on fat graft survival," Aesthet Surg J, 2012, 32: 622-633.
Allen et al., "Liposomal drug delivery systems: from concept to clinical applications," Adv Drug Deliv Rev, Elsevier, Jan. 2013, 65(1):36-48.
Alley et al., "Feasibility of drug screening with panels of human tumor cell lines using a microculture tetrazolium assay," Cancer Res., 1988, 48, 589-601.
Aluri et al., "Elastin-like peptide amphiphiles Form nanofibers with tunable length," Biomacromolecules, Sep. 2012, vol. 13, Issue 9, pp. 2645-2654.
Amanat et al., "A serological assay to detect SARS-CoV-2 seroconversion in humans," Nat Med, 2020, 26(7): 1033-1036.
American Diabetes Association, Standards of medical care in diabetes—2018. Diabetes Care, Jan. 2018, vol. 41, Supplement 1, pp. S1-S159.
American Hospital Association, "AHA Hospital Statistics," 2020 edition. Available at: <https://www.aha.org/statistics/fast-facts-us-hospitals>.
American Society of Plastic Surgeons, "2017 Plastic Surgery Statistics Report," Oct. 2018, 25 pages.
Amiram et al., "A depot-forming glucagon-like peptide-1 fusion protein reduces blood glucose for five days with a single injection," J. Control. Release, Nov. 2013, vol. 172, Issue, pp. 144-151.
Amiram et al., "Evolution of translation machinery in recoded bacteria enables multi-site incorporation of nonstandard amino acids," Nat Biotechnol, 2015, 33: 1272-1279.
Amiram et al., "Injectable protease-operated depots of glucagon-like peptide-1 provide extended and tunable glucose control," Proc. Natl. Acad. Sci., Feb. 2013, vol. 110, Issue 8, pp. 2792-2797.
Andersen et al., "Extending Half-life by Indirect Targeting of the Neonatal Fc Receptor (FcRn) Using a Minimal Albumin Binding Domain," Journal of Biological Chemistry, Feb. 2011, vol. 286, Issue 7, pp. 5234-5241.
Anselmo et al., "Nanoparticles in the clinic, " Bioeng Transl Med, Jun. 2016, 1(1):10-29.
Antos et al., "Lipid Modification of Proteins through Sortase-Catalyzed Transpeptidation," J. Am. Chem. Soc., Dec. 2008, vol. 130, Issue 48, pp. 16338-16343.
Antos et al., "Site-Specific N- and C-Terminal Labeling of a Single Polypeptide Using Sortases of Different Specificity," J. Am. Chem. Soc., Aug. 2009, vol. 131, Issue 31, pp. 10800-10801.
Appleyard et al., "Multiplexed protein quantification with barcoded hydrogel microparticles," Anal Chem, 2011, 83: 193-199.
Arami et al., "In vivo delivery, pharmacokinetics, biodistribution and toxicity of iron oxide nanoparticles," Chem Soc Rev, Dec. 2015, 44(23):8576-8607.
Arias et al., "Superior preclinical efficacy of gemcitabine developed as chitosan nanoparticulate system," Biomacromolecules, Jan. 2011, vol. 12, Issue 1, pp. 97-104.
Armbruster et al., "Limit of blank, limit of detection and limit of quantitation," Clin Biochem Rev, 2008, 29 Suppl 1: S49-52.
Armstrong et al., "Antibody against poly(ethylene glycol) adversely affects PEG-asparaginase therapy in acute lymphoblastic leukemia patients," Cancer, Jul. 2007, vol. 110, Issue 1, pp. 103-111.
Armstrong et al., "The Hydrodynamic Radii of Macromolecules and Their Effect on Red Blood Cell Aggregation," Biophys. J., 2004, 87, 4259-4270.
Arner et al., "FGF21 attenuates lipolysis in human adipocytes—a possible link to improved insulin sensitivity," FEBS Lett, May 2008, vol. 582, Issue 12, pp. 1725-1730.

(56) References Cited

OTHER PUBLICATIONS

Arnida et al., "Geometry and surface characteristics of gold nanoparticles influence their biodistribution and uptake by macrophages," Eur J Pharm Biopharm, Apr. 2011, vol. 77, Issue 3, pp. 417-423.
Arshavsky-Graham et al., "Lab-on-a-Chip Devices for Point-of-Care Medical Diagnostics," Advances in Biochemical Engineering/Biotechnology, 2020, 19 pages.
Asai et al., "Protein polymer hydrogels by in situ, rapid and reversible self-gelation," Biomaterials, Jul. 2012, vol. 33, Issue 21, pp. 5451-5458.
Astete et al., "Synthesis and characterization of PLGA nanoparticles," Journal of Biomaterials Science, Polymer Edition 2006, 17(3):247-289.
Atun et al., "Expanding global access to radiotherapy," Lancet Oncol, Sep. 2015, vol. 16, Issue 10, pp. 1153-1186.
Atyeo et al., "Distinct Early Serological Signatures Track with SARS-CoV-2 Survival," Immunity, 2020, 53: 524-532.
Averick et al., "ATRP under biologically relevant conditions: grafting from a protein," ACS Macro. Lett., Jan. 2012, vol. 1, Issue 1, pp. 6-10.
Averick et al., "Protein-polymer hybrids: conducting ARGET ATRP from a genetically encoded cleavable ATRP initiator," Eur. Polym. J., Oct. 2013, vol. 49, Issue 10, pp. 2919-2924.
Awai et al., "Studies of the metabolism of I-131-labeled human transferrin," J. Lab. Clin. Med. 61, 1963, 363-396.
Awasthi et al., "Comparative benefits of Nab-paclitaxel over gemcitabine or polysorbate-based docetaxel in experimental pancreatic cancer," Carcinogenesis, Oct. 2013, vol. 34, Issue 10, pp. 2361-2369.
Awasthi et al., "Evaluation of combination treatment benefits of nab-paclitaxel in experimental pancreatic cancer," Journal of Clinical Oncology, 2012, 30, 170.
Axup et al., "Synthesis of site-specific antibody-drug conjugates using unnatural amino acids," Proc Natl Acad Sci USA, Feb. 2012, vol. 109, Issue 40, pp. 16101-16106.
Azhdarinia et al., "Regional radiochemotherapy using in situ hydrogel," Pharm Res., 2005, 22, 776-783.
Babu, "The contribution of intrinsically disordered regions to protein function, cellular complexity, and human disease," Biochem Soc Trans, Oct. 2016, 44(5):1185-1200.
Bache et al., "Investigating the accuracy of microstereotactic-body-radiotherapy utilizing anatomically accurate 3D printed rodent-morphic dosimeters," Medical Physics, Feb. 2015, vol. 42, Issue 2, pp. 846-855.
Badi, "Non-linear PEG-based thermoresponsive polymer systems," Progress in Polymer Science, Mar. 2017, vol. 66, pp. 54-79.
Bae et al., "Targeted drug delivery to tumors: myths, reality and possibility," J Control Release, Elsevier, Aug. 2011, 153(3):198-205.
Baggio et al., "A recombinant human glucagon-like peptide (GLP)-1-albumin protein (Albugon) mimics peptidergic activation of GLP-1 receptor-dependent pathways coupled with satiety, gastrointestinal motility, and glucose homeostasis," Diabetes 53, 2004, 2492-2500.
Baggio et al., "Biology of Incretins: GLP-1 and GIP," Gastroenterology, May 2007, vol. 132, Issue 6, pp. 2131-2157.
Bailey et al., "Genomic analyses identify molecular subtypes of pancreatic cancer," Nature, Mar. 2016, vol. 531, Issue 7592, pp. 47-52.
Bain et al., "Formation of monolayer films by the spontaneous assembly of organic thiols from solution onto gold," Journal of the American Chemical Society, 1989, 111: 321-335.
Balaji, "Subdermal fat grafting for Parry-Romberg syndrome," Ann Maxillofac Surg, 2014, 4: 55-59.
Balu et al., "An16-resilin: an advanced multi-stimuli-responsive resilin-mimetic protein polymer," Acta Biomater, Nov. 2014, 10:4768-4777.
Bamford et al., "The COSMIC (Catalogue of Somatic Mutations in Cancer) database and website," British Journal of Cancer, 2004, 91, 355-358.
Banani et al., "Biomolecular condensates: organizers of cellular biochemistry," Nat Rev Mol Cell Biol, May 2017, 18(5):285-298.
Banerjee et al., "Nanoparticles in cancer chemotherapy," Prog Mol Biol Transl Sci, Elsevier, Nov. 2011, 104:489-507.
Banga et al., "Parenteral controlled delivery and parmacokinetics of therapeutic peptides and proteins," (CRC Press, Boca Raton, FL, 2005).
Banjade et al., "Phase transitions of multivalent proteins can promote clustering of membrane receptors," Elife, Oct. 2014, 3:e04123.
Bansal et al., "PEGylation improves pharmacokinetic profile, liver uptake and efficacy of Interferon gamma in liver fibrosis," J. Control. Release, Sep. 2011, vol. 154, Issue 3, pp. 233-240.
Banskota et al., "Genetically encoded stealth nanoparticles of a zwitterionic polypeptide-paclitaxel conjugate have wider therapeutic window than Abraxane in multiple tumor models," Nano Lett, Mar. 2020, 20(4):2396-2409.
Banyard et al., "Preparation, Characterization, and Clinical Implications of Human Decellularized Adipose Tissue Extracellular Matrix (hDAM): A Comprehensive Review," Aesthet Surg J, 2016, 36: 349-357.
Baraf et al., "Infusion-related reactions with pegloticase, a recombinant uricase for the treatment of chronic gout refractory to conventional therapy," J Clin Rheumatol, 2014, 20: 427-432.
Barbuti et al., "Paclitaxel through the ages of anticancer therapy: Exploring its role in chemoresistance and radiation therapy," Cancers, Dec. 2015, vol. 7, Issue 4, pp. 2360-2371.
Barnett et al., "Normal tissue reactions to radiotherapy: towards tailoring treatment dose by genotype," Nat Rev Cancer, Feb. 2009, vol. 9, Issue 2, pp. 134-142.
Barton et al., "Estimating the demand for radiotherapy form the evidence: A review of changes from 2003 to 2012," Radiother Oncol, Jul. 2014, vol. 112, Issue 1, pp. 140-144.
Baskar et al., "Cancer and Radiation Therapy: Current Advances and Future Directions," Int. J. Med. Sci., Feb. 2012, vol. 9, Issue 3, pp. 193-199.
Bates et al., "Block copolymer thermodynamics: theory and experiment," Annu Rev. Phys. Chem., 1990, 41:525-57.
Bedford et al., "WW domain-mediated interactions reveal a spliceosome-associated protein that binds a third class of proline-rich motif: The proline glycine and methionine-rich motif," PNAS, 1998, 95: 10602-10607.
Beenken et al., "The FGF family: biology, pathophysiology and therapy," Nat Rev Drug Discov, Mar. 2009, vol. 8, Issue 3, pp. 235-253.
Begg et al., "Strategies to improve radiotherapy with targeted drugs," Nat Rev Cancer, Apr. 2011, vol. 11, Issue 4, pp. 239-253.
Bellucci et al., "A noncanonical function of sortase enables site-specific conjugation of small molecules to lysine residues in proteins," Angew. Chem. Int. Ed. 54, Jan. 2015, vol. 54, Issue 2, pp. 441-445.
Bellucci et al., "Three-in-One Chromatography-Free Purification, Tag Removal, and Site-Specific Modification of Recombinant Fusion Proteins Using Sortase A and Elastin-like Polypeptides," Angewandte Chemie International Edition, Mar. 2013, vol. 52, Issue 13, pp. 3703-3708.
Bender et al., "Synthesis, Crystallization, and Biological Evaluation of an Orally Active Prodrug of Gemcitabine," J. Med. Chem., Nov. 2009, vol. 52, Issue 22, pp. 6958-6961.
Benn et al., "Physiology of Hyperuricemia and Urate-Lowering Treatments," Front Med (Lausanne), 2018, 5: 160, 28 pages.
Bennett et al., "Association of Fat Grafting With Patient-Reported Outcomes in Postmastectomy Breast Reconstruction," JAMA Surg, 2017, 152: 944-950.
Berisio et al., "Imino Acids and Collagen Triple Helix Stability: Characterization of Collagen-like Polypeptides Containing Hyp-Hyp-Gly Seqeucne Repeats," JACS, 2004, 126: 11402-11403.
Bernacki et al., "Length-dependent aggregation of uninterrupted polyalanine peptides," Biochemistry, Sep. 2011, vol. 50, Issue 43, pp. 9200-9211.
Berndt et al., "Synthetic lipidation of peptides and amino acids: Monolayer structure and properties," J. Am. Chem. Soc., 1995, 117, 9515-9522.
Berry et al., "Development and characterisation of neutralising monoclonal antibody to the SARS-coronavirus," J Virol Methods, 2004, 120: 87-96.

(56) References Cited

OTHER PUBLICATIONS

Bessa et al., "Thermoresponsive self-assembled elastin-based nanoparticles for delivery of BMPs," Journal of Controlled Release, Mar. 2010, vol. 142, Issue 3, pp. 312-318.
Best, "Computational and theoretical advances in studies of intrinsically disordered proteins," Curr Opin Struct Biol, Feb. 2017, 42:147-154.
Bhattacharyya et al., "A paclitaxel-loaded recombinant polypeptide nanoparticle outperforms Abraxane in multiple murine cancer models," Nat. Commun., Aug. 2015, Issue 6, Article 7939, 30 pages.
Bhattacharyya et al., "Encapsulating a Hydrophilic Chemotherapeutic into Rod-Like Nanoparticles of a Genetically Encoded Asymmetric Triblock Polypeptide Improves its Efficacy," Advanced functional materials, Mar. 2017, vol. 27, Issue 12, Article 1605421, 9 pages.
Bidwell et al., "Development of elastin-like polypeptide for thermally targeted delivery of doxorubicin," Biochemical Pharmacology, Mar. 2007, vol. 73, Issue 5, pp. 620-631.
Binz et al., "Engineering novel binding proteins from nonimmunoglobulin domains," Nat Biotechnol, 2005, 23(10):1257-68.
Blanco et al., "Principles of nanoparticle design for overcoming biological barriers to drug delivery," Nat Biotechnol, Sep. 2015, 33(9):941-51.
Blasko et al., "Brachytherapy for carcinoma of the prostate: Techniques, patient selection, and clinical outcomes," Seminars in Radiation Oncology, 2002, 12, 81-94.
Blasko et al., "The role of external beam radiotherapy with I-125/Pd-103 brachytherapy for prostate carcinoma," Radiother Oncol, 2000, 57, 273-278.
Blasko et al., "Transperineal percutaneous iodine-125 implantation for prostatic carcinoma using transrectal ultrasound and template guidance," Endocurietherapy/Hyperthermia Oncology, 1987, 3, 131-139.
Bley et al., "Microtubule stabilising agents and ionising radiation: Multiple exploitable mechanisms for combined treatment," Eur J Cancer, Jan. 2013, vol. 49, Issue 1, pp. 245-253.
Bobo et al., "Nanoparticle-based medicines: a review of FDA-approved materials and clinical trials to date." Pharmaceutical research, Oct. 2016, vol. 33, Issue 10, pp. 2373-2387.
Bocci et al., "The pharmacological bases of the antiangiogenic activity of paclitaxel," Angiogenesis, Jul. 2013, vol. 16, Issue 3, pp. 481-492.
Bochicchio et al., "Investigating by CD the molecular mechanism of elasticity of elastomeric proteins," Chirality, Sep. 2008, vol. 20, Issue 9, pp. 985-994.
Boekhorst et al., "Genome-wide detection and analysis of cell wall-bound proteins with LPxTG-like sorting motifs," J. Bacteriol. 187, 2005, 4928-4934.
Boeynaems et al., "Protein Phase Separation: A New Phase in Cell Biology," Trends Cell Biol, Jun. 2018, 28(6):420-435.
Boeynaems et al., "Spontaneous driving forces give rise to protein-RNA condensates with coexisting phases and complex material properties," Proc Natl Acad Sci U S A, 2019, 116:7889-7898.
Boldt, "Use of albumin: an update," Br J. Anaesth., Mar. 2010, vol. 104, Issue 3, pp. 276-284.
Bond, "Exenatide (Byetta) as a novel treatment option for type 2 diabetes mellitus," Proc. (Bayl. Univ. Med. Cent.), Jul. 2006, vol. 19, Issue 3, pp. 281-284.
Bontempo et al., "Streptavidin as a macroinitiator for polymerization: in situ protein-polymer conjugate formation," J. Am. Chem. Soc., 2005, 6508-6509.
Borst et al., "The Therapeutic Antibody LM609 Selectively Inhibits Ligand Binding to Human αVβ3 Integrin via Steric Hindrance," Structure, Nov. 2017, 25(11):1732-1739.e5.
Bowditch et al., "Identification of a novel integrin binding site in fibronectin. Differential utilization by β3 integrins," Journal of Biological Chemistry, 1994, 269(14):10856-10863.
Boyer et al., "Well-Defined Protein-Polymer Conjugates via in Situ RAFT Polymerization," J. Am. Chem. Soc., Jun. 2007, vol. 129, Issue 22, pp. 7145-7154.

Branco et al., "Self-assembling materials for therapeutic delivery," Acta Biomaterialia, Mar. 2009, vol. 5, Issue 3, pp. 817-831.
Brangwynne et al., "Polymer physics of intracellular phase transitions," Nature Physics, Nov. 2015, 11(11):899-904.
Brannon-Peppas et al., "Nanoparticle and targeted systems for cancer therapy," Advanced Drug Delivery Reviews, Elsevier, Sep. 2012, 64(11):206-212.
Broome et al., "Expanding the utility of beta-galactosidase complementation: piece by piece," Mol Pharm, ACS Publications, Feb. 2010, 7(1):60-74.
Broyer et al., "Emerging synthetic approaches for protein-polymer conjugations," Chem. Commun., Feb. 2011, vol. 47, Issue 8, pp. 2212-2226.
Brusa et al., "Antitumor activity and pharmacokinetics of liposomes containing lipophilic gemcitabine prodrugs," Anticancer Res., Jan. 2007, vol. 27, Issue 1A, pp. 195-199.
Bryant et al., "Serology for SARS-CoV-2: Apprehensions, opportunities, and the path forward," Sci Immunol, 2020, 5: eabc6347, 4 pages.
Brzezinski et al., "Autologous Fat Grafting to the Breast Using REVOLVE System to Reduce Clinical Costs," Ann Plast Surg, 2016, 77: 286-289.
Burchard, "Light Scattering Techniques," Physical techniques for the study of food biopolymers, 1994, 151-213.
Burke et al., "Multimodal nanoparticle imaging agents: design and applications," Philos Trans A Math Phys Eng Sci, Nov. 2017, 375:20170261.
Burnouf, "Modern plasma fractionation," Transfus. Med. Rev., Apr. 2007, vol. 21, Issue 2, pp. 101-117.
Buteau et al., "Glucagon-like peptide-1 prevents beta cell glucolipotoxicity," Diabetologia, 2004, 47(5):806-815.
Butler et al., "B-Cell Deficit and Increased B-Cell Apoptosis in Humans With Type 2 Diabetes," Diabetes, 2003, 52(1):102-110.
Cabral et al., "Accumulation of sub-100 nm polymeric micelles in poorly permeable tumours depends on size," Nature Nanotechnology, Oct. 2011, vol. 6, Issue 12, pp. 815-823.
Cabrera et al., "Automated, High-Throughput Assays for Evaluation of Human Pancreatic Islet Function," Cell Transplant, First published Nov. 2007, vol. 16, Issue 10, pp. 1039-1048.
Cabrera et al., "Glutamate Is a Positive Autocrine Signal for Glucagon Release," Cell Metab, Jun. 2008, vol. 7, Issue 6, pp. 545-554.
Cai et al., "Long-acting preparations of exenatide," Drug Des. Devel. Ther., Sep. 2013, vol. 7, pp. 963-970.
Calabrese et al., "Frequency, distribution and immunologic nature of infusion reactions in subjects receiving pegloticase for chronic refractory gout," Arthritis Res Ther, 2017, 19: 191, 7 pages.
Caliceti et al., "Pharmacokinetic and biodistribution properties of poly(ethylene glycol)-protein conjugates," Adv. Drug Deliv. Rev, 2003, 55, 1261-1277.
Callahan et al., "Triple stimulus-responsive polypeptide nanoparticles that enhance intratumoral spatial distribution," Nano Letters, Mar. 2012, vol. 12, Issue 4, pp. 2165-2170.
Camilloni et al., "Determination of secondary structure populations in disordered states of proteins using nuclear magnetic resonance chemical shifts," Biochemistry, Feb. 2012, vol. 51, Issue 11, pp. 2224-2231.
Campbell et al., "Pegylated peptides V. Carboxy-terminal PEGlyted analogs of growth hormone-releasing factor (GRF) display enhanced duration of biological activity in vivo," J. Peptide Res., 1997, 49:527-537.
Cao et al., "Monitoring the effects of anti-angiogenesis on the radiation sensitivity of pancreatic cancer xenografts using dynamic contrast-enhanced computed tomography," Int J Radiation Oncol Biol Phys, Feb. 2014, vol. 88, Issue 2, pp. 412-418.
Cardenes et al., "Locally advanced pancreatic cancer: Current therapeutic approach," The Oncologist, Jun. 2006, vol. 11, Issue 6, pp. 612-623.
Carreiras et al., "Expression and localization of alpha v integrins and their ligand vitronectin in normal ovarian epithelium and in ovarian carcinoma," Gynecol Oncol, 1996, 62(2):260-7.
Carrico et al., "Introducing genetically encoded aldehydes into proteins," Nat Chem Biol, Jun. 2007, vol. 3, Issue 6, pp. 321-322.

(56) References Cited

OTHER PUBLICATIONS

Cataldo et al., "Radiation-induced crosslinking of collagen gelatin into a stable hydrogel," Journal of Radioanalytical and Nuclear Chemistry, Sep. 2008, vol. 275, Issue 1, pp. 125-131.

Caves et al., "Thermal inactivation of uricase (urate oxidase): mechanism and effects of additives," Biochemistry, 2013, 52: 497-507.

Centers for Disease Control and Prevention, "National Diabetes Statistics Report, 2017," Atlanta, GA: Centers for Disease Control and Prevention, US Department of Health and Human Services; 2017. Reviewed: Feb. 24, 2018.

Ceska et al., "A new and rapid method for the clinical determination of a-amylase activities in human serum and urine. Optimal conditions," Clinica Chimica Acta, 1969, 26, 437-444.

Cha et al., "Microfluidics-assisted fabrication of gelatin-silica core-shell microgels for injectable tissue constructs," Biomacromolecules, 2014, 15: 283-290.

Chae et al., "Pharmacokinetic and pharmacodynamic evaluation of site-specific PEGylated glucagon-like peptide-1 analogs as flexible postprandial-glucose controllers," J Pharm Sci, 2009, 98(4): 1556-1567.

Chakrabartty et al., "Stability of α-Helices," Adv Protein Chem, 1995, 46, 141-176.

Champion et al., "Particle shape: a new design parameter for micro- and nanoscale drug delivery carriers," J Control Release, Elsevier, Aug. 2007, 121(1-2):3-9.

Champion et al., "Role of particle size in phagocytosis of polymeric microspheres," Pharm Res, Srpinger, Mar. 2008, 25(8):1815-21.

Champion et al., "Role of target geometry in phagocytosis," Proc Natl Acad Sci U S A, The National Academy of Sciences of the USA, Mar. 2006, 103(13):4930-4.

Champion et al., "Shape induced inhibition of phagocytosis of polymer particles," Pharm Res, Springer, Jan. 2009, 26(1):244-9.

Chang et al., "Thermoprecipitation of Glutathione S-Transferase by Glutathione-Poly(N-isopropylacrylamide) Prepared by RAFT Polymerization," Macromolecular Rapid Communications, Oct. 2010, 31: 1691-1695.

Chang et al., "Tumor-stroma interaction in orthotopic primary pancreatic cancer xenografts during hedgehog pathway inhibition," Int. J. Cancer, Jul. 2013, vol. 133, Issue 1, pp. 225-235.

Chapin et al., "Rapid microRNA profiling on encoded gel microparticles," Angew Chem Int Ed Engl, 2011, 50: 2289-2293.

Chatterjee et al., "Type 2 diabetes," The Lancet, Jun. 2017, vol. 389, Issue 10085, pp. 2239-2251.

Chaudhury et al., "The major histocompatibility complex-related Fc receptor for IgG (FcRn) binds albumin and prolongs its lifespan," J Exp Med, 2003, 197(3): p. 315-22.

Chen et al., "Anisotropic hydrogels fabricated with directional freezing and radiation-induced polymerization and crosslinking method," Materials Letters, Dec. 2012, vol. 89, pp. 104-107.

Chen et al., "Anti-hypervariable region antibody induced by a defined peptide: An approach for studying the structural correlates of idiotypes," PNAS, 1984, 81:1784-1788.

Chen et al., "Bioinspired Modular Synthesis of Elastin-Mimic Polymers To Probe the Mechanism of Elastin Elasticity," J. Am. Chem. Soc., Mar. 2010, vol. 132, Issue 13, pp. 4577-4579.

Chen et al., "Real-world patterns of pegloticase use for treatment of gout: descriptive multidatabase cohort study," BMJ Open, 2020, 10: e041167, 6 pages.

Chen et al., "Rheology of Soft Materials," Annual Review of Condensed Matter Physics, May 2010, vol. 1, pp. 301-322.

Chen et al., "Site-specific labeling of cell surface proteins with biophysical probes using biotin ligase," Nat Methods, 2005, 2(2):99-104.

Chen et al., "The influence of polymer topology on pharmacokinetics: differences between cyclic and linear PEGylated poly(acrylic acid) comb polymers," J Control Release, 2009, 140: 203-209.

Chen et al., "The use of self-adjuvanting nanofiber vaccines to elicit high-affinity B cell responses to peptide antigens without inflammation," Biomaterials, Nov. 2013, vol. 34, Issue 34, pp. 8776-8785.

Chen, "Small-molecule delivery by nanoparticles for anticancer therapy," Trends Mol Med, Cell Press, Dec. 2010, 16(12):594-602.

Chilkoti et al., "Design of thermally responsive, recombinant polypeptide carriers for targeted drug delivery," Advance Drug Delivery Reviews, 2002, 54:1093-1111.

Chilkoti et al., "Stimulus responsive elastin biopolymers: applications in medicine and biotechnology," Curr Opin Chem Biol, Dec. 2006, vol. 10, Issue 6, pp. 652-657.

Chilkoti et al., "Targeted drug delivery by thermally responsive polymers," Advanced Drug Delivery Reviews, 2002, 54:613-630.

Chin et al., "Addition of p-azido-I-phenylalanine to the genetic code of *Escherichia coli*," Journal of the American Chemical Society, 2002, 124: 9026-9027.

Chithrani et al., "Determining the size and shape dependence of gold nanoparticle uptake into mammalian cells," Nano Lett, Apr. 2006, vol. 6, Issue 4, pp. 662-668.

Chithrani et al., "Elucidating the mechanism of cellular uptake and removal of protein-coated gold nanoparticles of different sizes and shapes," Nano letters, ACS Publications, Jun. 2007, 7(6):1542-1550.

Chitkara et al., "Self-Assembling, Amphiphilic Polymer-Gemcitabine Conjugate Shows Enhanced Antitumor Efficacy Against Human Pancreatic Adenocarcinoma," Bioconjug. Chem., Jun. 2013, vol. 24, Issue 7, pp. 1161-1173.

Cho et al., "Effects of hofmeister anions on the phase transition temperature of elastin-like polypeptides," J. Phys. Chem. B., Nov. 2008, vol. 112, Issue 44, pp. 13765-13771.

Cho et al., "Hydrogen bonding of β-turn structure is stabilized in D(2)O," J Am Chem Soc, Oct. 2009, vol. 131, Issue 42, pp. 15188-15193.

Cho et al., "Therapeutic nanoparticles for drug delivery in cancer," Clin. Cancer Res., Mar. 2008, vol. 14, Issue 5, pp. 1310-1316.

Chockalingam et al., "Design and application of stimulus-responsive peptide systems," Protein Engineering, Design & Selection, Apr. 2007, 20(4):155-161.

Choi et al., "Multiplexed detection of mRNA using porosity-tuned hydrogel microparticles," Anal Chem, 2012, 84: 9370-9378.

Choi et al., "Recent advances in engineering microparticles and their nascent utilization in biomedical delivery and diagnostic applications," Lab Chip, 2017, 17: 591-613.

Choi et al., "Renal Clearance of Nanoparticles," Nature biotechnology, Oct. 2007, vol. 25, Issue 10, pp. 1165-1170.

Chow et al., "Peptide-based biopolymers in biomedicine and biotechnology," Mater. Sci. Eng. R Reports, Jan. 2008, vol. 62, Issue 4, pp. 125-155.

Chow et al., "Ultra-High Expression of a Thermally Responsive Recombinant Fusion Protein in *E. coli*," Biotechnology Progress, Sep. 2006, vol. 22, Issue 3, pp. 638-646.

Choy et al., "Investigation of taxol as a potential radiation sensitizer," Cancer, 1993, 71, 3774-3778.

Christensen et al., "Fusion order controls expression level and activity of elastin-like polypeptide fusion proteins," Protein Science, Jul. 2009, vol. 18, Issue 7, pp. 1377-1387.

Christensen et al., "Predicting Transition Temperatures of Elastin-Like Polypeptide Fusion Proteins," Biomacromolecules, Mar. 2013, vol. 14, Issue 5, pp. 1514-1519.

Chu et al., "Controllable monodisperse multiple emulsions," Angew Chem Int Ed Engl, 2007, 46: 8970-8974.

Chu et al., "Molecular Diagnosis of a Novel Coronavirus (2019-nCOV) Causing an Outbreak of Pneumonia," Clin Chem, 2020, 66(4): 549-555.

Cid-Arregui et al., "Perspectives in the treatment of pancreatic adenocarcinoma," World Journal of Gastroenterology, Aug. 2015, vol. 21, Issue 31, pp. 9297-9316.

Ciezki et al., "Brachytherapy or surgery? A composite view," Oncology, Oct. 2009, vol. 23, Issue 11, pp. 960-964.

Cima, "AVMA Guidelines for the Euthanasia of Animal: 2013 Edition," Journal of the American Veterinary Medical Association, Jan. 2013, vol. 242, 102 pages.

Cirulis et al., "Viscoelastic properties and gelation of an elastin-like polypeptide," Journal of Rheology, Sep. 2009, vol. 53, Issue 5, pp. 1215-1228.

(56) References Cited

OTHER PUBLICATIONS

Clarke et al., "Tropoelastin massively associates during coacervation to form quantized protein spheres," Biochemistry, Jul. 2006, vol. 45, Issue 33, pp. 9989-9996.
Clavé et al., "Amylase, lipase, pancreatic isoamylase, and phospholipase A in diagnosis of acute pancreatitis," Clinical Chemistry, 1995, 41, 1129-1134.
Coin et al., "Solid-phase peptide synthesis: from standard procedures to the synthesis of difficult sequences," Nat. Protoc., Dec. 2007, vol. 2, Issue 12, 3247-3256.
Colomb et al., "Radiation-Convertible Polymers from Norbornenyl Derivatives. Crosslinking with Ionizing Radiation," Journal of Applied Polymer Science, 1970, 14, 1659-1670.
Cong et al., "Nucleocapsid Protein Recruitment to Replication-Transcription Complexes Plays a Crucial Role in Coronaviral Life Cycle," J Virol, 2020, 94: e01925-19, 21 pages.
Conner et al., "Regulated portals of entry into the cell," Nature, 2003, 422(6927):37-44.
Conrad et al., "ELPylated anti-human TNF therapeutic single-domain antibodies for prevention of lethal septic shock," Plant Biotechnology Journal, Jan. 2011, vol. 9, Issue 1, pp. 22-31.
Coskun et al., "Fibroblast Growth Factor 21 Corrects Obesity in Mice," Endocrinology, Dec. 2008, vol. 149, Issue 12, pp. 6018-6027.
Costa et al., "Active Targeting of Cancer Cells by Nanobody Decorated Polypeptide Micelle with Bio-orthogonally Conjugated Drug," Nano letters, Dec. 2018, 19(1):247-254.
Costa et al., "Photo-crosslinkable unnatural amino acids enable facile synthesis of thermoresponsive nano- to microgels of intrinsically disordered polypeptides," Adv Mater, 2018, 30(5): 1704878.
Craik et al., "The future of peptide-based drugs," Chemical biology & drug design 81, Dec. 2013, vol. 81, Issue 1, pp. 136-147.
Crowther, "The ELISA guidebook," Methods Mol Biol, 2000, 149(III-IV): 1-413.
Cui et al., "Amino acid sequence in constitutionally isomeric tetrapeptide amphiphiles dictates architecture of one-dimensional nanostructures," J. Am. Chem. Soc., Aug. 2014, vol. 136, Issue 35, 12461-12468.
Cui et al., "Self-assembly of peptide amphiphiles: from molecules to nanostructures to biomaterials," Biopolymers, Jan. 2010, vol. 94, Issue 1, pp. 1-18.
Dai et al., "Versatile biomanufacturing through stimulus-responsive cell-material feedback," Nature chemical biology, Sep. 2019, 15(10):1017-1024.
Dalhaimer et al., "Single Molecule Visualization of Stable, Stiffness-Tunable, Flow-Conforming Worm Micelles," Macromolecules, 2003, 36(18):6873-6877.
Dalla Poza et al., "Targeting gemcitabine containing liposomes to CD44 expressing pancreatic adenocarcinoma cells causes an increase in the antitumoral activity," Biochim. Biophys. Acta, May 2013, vol. 1828, Issue 5, pp. 1396-1404.
Darling et al., "Viscoelastic properties of zonal articular chondrocytes measured by atomic force microscopy," Osteoarthritis Cartilage, 2006, 14: 571-579.
Darzynkiewicz et al., "DNA content measurement for DNA ploidy and cell cycle analysis," Current Protocols in Cytometry, 2001, 7.5.1-7.5.24.
Das et al., "Conformations of intrinsically disordered proteins are influenced by linear sequence distributions of oppositely charged residues," Proc Natl Acad Sci U S A, National Academy of Sciences, Aug. 2013, 110(33):13392-13397.
Dasgupta et al., "Isopeptide Ligation Catalyzed by Quintessential Sortase A: Mechanistic Cues From Cyclic and Branched Oligomers of Indolicidin," The Journal of Biological Chemistry, May 2011, vol. 286, No. 27, pp. 23996-24006, Supplemental Information.
Day et al., "A new glucagon and GLP-1 co-agonist eliminates obesity in rodents," Nat Chem Biol, Oct. 2009, 5:749.
De et al., "Temperature-Regulated Activity of Responsive Polymer-Protein Conjugates Prepared by Grafting-from via RAFT Polymerization," J. Am. Chem. Soc. Jul. 2008, 130, 11288-11289.

De Leon-Rodriguez et al., "Multifunctional thermoresponsive designer peptide hydrogels," Acta Biomaterialia, 2017, 47: 40-49.
De Simone et al., "Accurate random coil chemical shifts from an analysis of loop regions in native states of proteins," J Am Chem Soc, Nov. 2009, 131, 16332-16333.
Deer et al., "Phenotype and genotype of pancreatic cancer cell lines," Pancreas, May 2010, 39, 425-435.
Dejana et al., "The role of adherens junctions and VE-cadherin in the control of vascular permeability," J Cell Sci, Jul. 2008, 121, 2115-2122.
Delaglio et al., "NMRPipe: A multidimensional spectral processing system based on UNIX pipes," Journal of Biomolecular NMR 6, 1995, 277-293.
DeLisser et al., "Vascular endothelial platelet endothelial cell adhesion molecule 1(PECAM-1) regulates advanced metastatic progression," PNAS, Oct. 2010, 107, 18616-18621.
Dennis et al., "Albumin binding as a general strategy for improving the pharmacokinetics of proteins," J Biol Chem, 2002, 277(38): p. 35035-43.
Dennis et al., "Co-Translational Myristoylation Alters the Quaternary Structure of HIV-1 Nef in Solution," Proteins: Structure, Function, and Bioinformatics, 2005, 60:658-669.
Depp et al., "Native protein-initiated ATRP: A viable and potentially superior alternative to PEGylation for stabilizing biologics," Acta Biomater. Feb. 2009, 5, 560-569.
Deshayes et al., "Radium 223 dichloride for prostate cancer treatment," Drug Des Devel Ther, Sep. 2017, 11, 2643-2651.
DeYoung et al., "Encapsulation of exenatide in poly-(D,L-lactide-co-glycolide) microspheres produced an investigational long-acting once-weekly formulation for type 2 diabetes," Diabetes Technol Ther, Nov. 2011, 13, 1145-1154.
Diana et al., "Prognostic role and correlation of CA9, CD31, CD68 and CD20 with the desmoplastic stroma in pancreatic ductal adenocarcinoma," Oncotarget, Nov. 2016, 7, 72819-72832.
Diehl et al., "A Good Practice Guide to the Administration of Substances and Removal of Blood Including Routes and Volumes," J Appl Toxicol, 2001, 21, 15-23.
Dignon et al., "Relation between single-molecule properties and phase behavior of intrinsically disordered proteins," Proc Natl Acad Sci U S A, Oct. 2018, 115(40):9929-9934.
Dignon et al., "Sequence determinants of protein phase behavior from a coarse-grained model," PLoS Comput Biol, Jan. 2018, 14(1):e1005941.
Dincer et al., "Multiplexed Point-of-Care Testing—xPOCT," Trends Biotechnol, 2017, 35(8): 728-742.
Ding et al., "Mechanism for the alpha-helix to beta-hairpin transition," Proteins, 2003, 53, 220-228.
Ding et al., "βKlotho Is Required for Fibroblast Growth Factor 21 Effects on Growth and Metabolism," Cell Metab, Sep. 2012, 16(3):387-393.
Dong et al., "An interactive web-based dashboard to track COVID-19 in real time," Lancet Infect Dis, 2020, 20: 533-534.
Donnelly et al., "DNA Vaccines," Ann. Rev. Immunol., 1997, 15, 617-648.
Dreher et al., "Evaluation of an elastin-like polypeptide-doxorubicin conjugate for cancer therapy," J. of Controlled Release, 2003, 91:31-43.
Dreher et al., "Temperature triggered self-assembly of polypeptides into multivalent spherical micelles," J. Am. Chem. Soc. Jan. 2008, 130, 687-694.
Dreher et al., "Thermal cycling enhances the accumulation of a temperature-sensitive biopolymer in solid tumors," Cancer Res, May 2007, 67, 4418-4424.
Dreher, M. R. Ph.D. Thesis, Duke University, Durham, NC, Apr. 2006.
Dreis et al., "Preparation, Characterisation and Maintenance of Drug Efficacy of Doxorubicin-Loaded Human Serum Albumin (HSA) Nanoparticles," Int. J. Pharm., Aug. 2007, 341, 207-214.
Drucker "Mechanisms of Action and Therapeutic Application of Glucagon-like Peptide-1," Cell Metab, Apr. 2018, 27(4):740-756.
Drucker et al., "The incretin system: glucagon-like peptide-1 receptor agonists and dipeptidyl peptidase-4 inhibitors in type 2 diabetes," Lancet 368, Nov. 2006, 1696-1705.

(56) References Cited

OTHER PUBLICATIONS

Drucker, "Glucagon-like peptides," Diabetes 47, 1998, 159-169.
Drucker, "Incretin action in the pancreas: potential promise, possible perils, and pathological pitfalls," Diabetes, Oct. 2013, 62, 3316-3323.
Du et al., "Endoscope-assisted brachytherapy for pancreatic cancer: From tumor killing to pain relief and drainage," Journal of interventional gastroenterology, Jan. 2011, 1, 23-27.
Du et al., "Tailor-made dual pH-sensitive polymer-doxorubicin nanoparticles for efficient anticancer drug delivery," J. Am. Chem. Soc., Oct. 2011, 133, 17560-17563.
Duan et al., "Fibronectin type III domain based monobody with high activity," Biochemistry, Oct. 2007 46(44):12656-12664.
Duan et al., "Improving the thermostability and catalytic efficiency of Bacillus deramificans pullulanase by site-directed mutagenesis," Appl Environ Microbiol, American Society for Microbiology, Jul. 2013, 79(13):4072-4077.
Dubey et al., "Development and evaluation of folate functionalized albumin nanoparticles for targeted delivery of gemcitabine," Int J Pharm., Aug. 2015, 492(1-2):80-91.
Ducreux et al., "Radiation plus docetaxel and cisplatin in locally advanced pancreatic carcinoma: A non-comparative randomized phase II trial," Digestive and Liver Disease, Oct. 2014, 46, 950-955.
Duke University, "Gemcitabine/Nab-Paclitaxel With HIGRT in Resectable Pancreatic Cancer," Clinical Trial NCT02318095 <https://clinicaltrials.gov/ct2/show/NCT02318095> Webpage accessed Jan. 11, 2017.
Duncan, "The dawning era of polymer therapeutics," Nature Reviews Drug Discovery, 2003, 2, 347-360.
Duncan, R. "Polymer conjugates as anticancer nanomedicines," Nat. Rev. Cancer, Sep. 2006, 6, 688-701.
Duronio et al., "Protein N-myristoylation in *Escherichia coli*: Reconstitution of a eukaryotic protein modification in bacteria," Proc. Natl. Acad. Sci. USA, 1990, vol. 87, pp. 1506-1510.
Dutta et al., "The Nucleocapsid Protein of SARS-CoV-2: a Target for Vaccine Development," J Virol, 2020, 94(13): e00647-20, 2 pages.
Dyrberg et al., "Peptide as Atigens," J. Exp. Med., 1986, 164:1344-1349.
Dzuricky et al., "Avidity and Cell Uptake of Integrin Targeting Polypeptide Micelles is Strongly Shape Dependent," Nano letters, Sep. 2019, 19(9):6124-6132.
Dzuricky et al., "The Convergence of Artificial Protein Polymers and Intrinsically Disordered Proteins," Biochemistry, May 2018, 57(17):2405-2414.
Egan et al., "The Insulinotropic Effect of Acute Exendin-4 Administered to Humans: Comparison of Nondiabetic State to Type 2 Diabetes," The Journal of Clinical Endocrinology & Metabolism, 2002, 87, 1282-1290.
Ehlerding et al., "Biodegradable and Renal Clearable Inorganic Nanoparticles," Adv Sci (Weinh), Feb. 2016, 3(2):1500223.
Eisenhaber et al., "Prediction of lipid posttranslational modifications and localization signals from protein sequences: Big-II, NMT and PTS1," Nucleic Acids Res., 2003, 31, 3631-3634.
Eisenhauer et al., "New response evaluation criteria in solid tumours: Revised RECIST guideline (version 1.1)," Eur J Cancer, Jan. 2009, 45(2):228-247.
Ekladious et al., "Polymer-drug conjugate therapeutics: advances, insights and prospects," Nature Reviews Drug Discovery, 2019, 18:273-294.
El-Assaad et al., "Saturated Fatty Acids Synergize with Elevated Glucose to Cause Pancreatic B-Cell Death," Endocrinology, 2003, 144(9):4154-4163.
Elbaum-Garfinkle et al., "The disordered P granule protein LAF-1 drives phase separation into droplets with tunable viscosity and dynamics," Proc Natl Acad Sci U S A, Jun. 2015, 112(23):7189-7194.
Ellis, "Macromolecular crowding: obvious but underappreciated," Trends Biochem. Sci., 2001, 26 (10), 597-604.

Elsabahy et al., "Design of polymeric nanoparticles for biomedical delivery applications," Chem Soc Rev, Royal Society of Chemistry, Apr. 2012, 41(7):2545-61.
Elvin et al., "Synthesis and properties of crosslinked recombinant pro-resilin," Nature, 2005, 437(7061):999-1002.
Elzoghby et al., "Implications of Protein- and Peptide-Based Nanoparticles as Potential Vehicles for Anticancer Drugs," Advances in Protein Chemistry and Structural Biology, Academic Press, Elsevier, Mar. 2015, Chapter Six, vol. 98, pp. 169-221.
Engin et al., "Thermoradiotherapy in the management of superficial malignant tumors," Clinical Cancer Research, 1995, 1, 139-145.
Eom et al., "The number of operations required for completing breast reconstruction," Plast Reconstr Surg Glob Open, 2012, 2: e242.
Erickson-Miller et al., "Differential toxicity of camptothecin, topotecan and 9-aminocamptothecin to human, canine, and murine myeloid progenitors (CFU-GM) in vitro," Cancer Chemother. Pharmacol., 1997, 39 (5), 467-472.
Etrych et al., "HPMA Copolymer Conjugates of Paclitaxe; and Docetaxel with pH-Controlled Drug Release," Molecular Pharmaceutics, Jun. 2010, 7(4):1015-1026.
Falk et al., "Hyperthermia in oncology," Int J Hyperthermia, 2001, 17, 1-18.
Farazi et al., "Structures of *Saccharomyces cerevisiae* N-myristoyltransferase with bound myristoylCoA and peptide provide insights about substrate recognition and catalysis," Biochemistry, 2001, 40, 6335-6343.
Farmer et al., "Conformational behavior of chemically reactive alanine-rich repetitive protein polymers," Biomacromolecules, 2005, 6, 1531-1539.
Farokhzad et al., "Targeted nanoparticle-aptamer bioconjugates for cancer chemotherapy in vivo," Proc Natl Acad Sci U S A, The National Academy of Sciences of the USA, Apr. 2006, 103(16):6315-20.
Fathallah et al., "Immunogenicity of Subcutaneously Administered Therapeutic Proteins—a Mechanistic Perspective," The AAPS Journal, 2013, 15(4): 897-900.
Feng et al., "Protein resistant surfaces: comparison of acrylate graft polymers bearing oligo-ethylene oxide and phosphorylcholine side chains," Biointerphases, Mar. 2006, 1 (1), 50.
Fernandez-Colino et al., "Amphiphilic Elastin-Like Block Co-Recombinamers Containing Leucine Zippers: Cooperative Interplay between Both Domains Results in Injectable and Stable Hydrogels," Biomacromolecules, Sep. 2015, 16, 3389-3398.
Finan et al., "A rationally designed monomeric peptide triagonist corrects obesity and diabetes in rodents," Nat Med, Jan. 2015, 21:27-36.
Finan et al., "Unimolecular Dual Incretins Maximize Metabolic Benefits in Rodents, Monkeys, and Humans," Sci Transl Med, Oct. 2013, 5(209):209ra151.
Fluegel et al., "Chain stiffness of elastin-like polypeptides," Biomacromolecules, Oct. 2010, 11, 3216-3218.
Fosgerau et al., "Peptide therapeutics: current status and future directions," Drug Discovery Today, Jan. 2015, 20, 122-128.
Fox et al., "Soluble polymer carriers for the treatment of cancer: the importance of molecular architecture," Acc Chem Res, 2009, 42(8):1141-1151.
Frandsen et al., "Recombinant protein-based polymers for advanced drug delivery," Chem Soc Rev, 2012, 41: 2696-2706.
Franzmann et al., "Phase separation of a yeast prion protein promotes cellular fitness," Science, Jan. 2018, 359(6371):eaao5654.
Free et al., "A Phase 1, multi-center, randomized, double-blind, placebo controlled study to evaluate the safety/tolerability, pharmacokinetic and hemodynamic response following single ascending subcutaneous doses of PB1046 (Vasomera) in subjects with essential hypertension," Circulation, Mar. 2018, 130:A19112.
Friedman et al., "Directed Evolution to Low Nanomolar Affinity of a Tumor-Targeting Epidermal Growth Factor Receptor-Binding Affibody Molecule," J. Mol. Biol., Mar. 2008, 376, 1388-1402.
Frilling et al., "Recommendations for management of patients with neuroendocrine liver metastases," The lancet oncology, Jan. 2014, 15, e8-21.

(56) References Cited

OTHER PUBLICATIONS

Fu et al., "Nanoparticle Albumin—Bond (NAB) Technology is a Promising Method for Anti-Cancer Drug Delivery," Recent Patents on Anti-Cancer Drug Discovery, Nov. 2009. 4(3):262-272.
Fujiwara et al., "Modulating effect of the PI3-kinase inhibitor LY294002 on cisplatin in human pancreatic cancer cells," Journal of Experimental & Clinical Cancer Research, Nov. 2008, 27, 76.
Furgeson et al., "Structural optimization of a "smart" doxorubicin-polypeptide conjugate for thermally targeted delivery to solid tumors," Journal of Controlled Release, Jan. 2006, 110:362-369.
Furumoto et al., "Effect of coupling of albumin onto surface of PEG liposome on its In vivo disposition," International Journal of Pharmaceutics, Mar. 2007, 329(1-2): p. 110-116.
Gaberc-Porekar et al., "Obstacles and pitfalls in the PEGylation of therapeutic proteins," Curr. Opin. Drug Discov. Devel. 11, Mar. 2008, 242-250.
Gabizon et al., "Prolonged circulation time and enhanced accumulation in malignant exudates of doxorubicin encapsulated in polyethylene-glycol coated liposomes," Cancer Res., Feb. 1994, 54, 987-992.
Gabriel et al., "Fat grafting and breast reconstruction: tips for ensuring predictability," Gland Surg, 2015, 4: 232-243.
Gaich et al., "The Effects of LY2405319, an FGF21 Analog, in Obese Human Subjects with Type 2 Diabetes," Cell Metab, Sep. 2013, 18(3):333-340.
Ganson et al., "Control of hyperuricemia in subjects with refractory gout, and induction of antibody against poly(ethylene glycol) (PEG), in a phase I trial of subcutaneous PEGylated urate oxidase," Arthritis Res. Ther. 8, Feb. 2006, R12-R22.
Ganson et al., "Pre-existing anti-polyethylene glycol antibody linked to first-exposure allergic reactions to pegnivacogin, a PEGylated RNA aptamer," J Allergy Clin Immunol, May 2016, 137(5): 1610-1613, e1617.
Gao et al., "In situ growth of a PEG-like polymer from the C terminus of an intein fusion protein improves pharmacokinetics and tumor accumulation" PNAS Early Edition, Jul. 2010, vol. 107, 1-6.
Gao et al., "In situ growth of a PEG-like polymer from the C terminus of an intein fusion protein improves pharmacokinetics and tumor accumulation," Proc. Natl. Acad. Sci., Sep. 2010, 107(38):16432-16437.
Gao et al., "In situ growth of a stoichiometric PEG-like conjugate at a protein's N-terminus with significantly improved pharmacokinetics," Proc. Natl. Acad. Sci., Sep. 2009, 15231-15236.
Gao, "Site-specific and in situ growth of stealth polymer conjugates of proteins with significally improved pharmacology," Journal of Controlled Release, Nov. 2013, 172(1):e116-e117.
Garanger et al., "Structural Evolution of a Stimulus-Responsive Diblock Polypeptide Micelle by Temperature Tunable Compaction of its Core," Macromolecules, Sep. 2015, 48, 6617-6627.
Garay et al., "Antibodies against polyethylene glycol in healthy subjects and in patients treated with PEG-conjugated agents," Expert Opinion. Drug Deliv. 9, Nov. 2012, 1319-1323.
Garay et al., "Therapeutic perspectives on uricases for gout," Joint Bone Spine, 2012, 79: 237-242.
Garcia Quiroz et al., "Syntax of Phase Transition Peptide Polymers with LCST and UCST Behavior," Jan. 1, 2013, Retrieved from the Internet: URL:https://dukespace.lib.duke.edu/dspace/bitstream/handle/10161/7256/GarciaQuirozduke0066D 11972.pdf?sequence=I&isAllowed=y.
Gauthier et al., "Peptide/protein-polymer conjugates: synthetic strategies and design concepts," Chem. Commun., Jul. 2008, 2591-2611.
Ge et al., "Self-Cleavable Stimulus Responsive Tags for Protein Purification without Chromatography" J. Am. Chem. Soc., 2005, 127: 11228-11229.
Genbank Accession NM_001182082.1 (Mar. 2017).
Geng et al., Shape effects of filaments versus spherical particles in flow and drug delivery, Nat Nanotechnol, Nature Research, Apr. 2007, 2(4):249-55.

Ghoorchian et al., "Molecular architecture influences the thermally induced aggregation behavior of elastin-like polypeptides," Biomacromolecules, Oct. 2011, 12, 4022-4029.
Gianni et al., "Nonlinear pharmacokinetics and metabolism of paclitaxel and its pharmacokinetic/pharmacodynamic relationships in humans," J. Clin. Oncol., 1995, 13 (1), 180-190.
Giberti et al., "Radical retropubic prostatectomy versus brachytherapy for low-risk prostatic cancer: a prospective study," World J Urol, Oct. 2009, 27, 607-612.
Gibson et al., "Enzymatic assembly of DNA molecules up to several hundred kilobases," Nat Methods, May 2009, 6, 343-345.
Gilbreth et al., "Structural insights for engineering binding proteins based on non-antibody scaffolds," Curr Opin Struct Biol, Elsevier, Jun. 2012, 22(4):413-20.
Gillies et al., "Dendrimers and dendritic polymers in drug delivery," Drug Discovery Today, 2005, 10(1):35-43.
Gilroy et al., "Fusion of fibroblast growth factor 21 to a thermally responsive biopolymer forms an injectable depot with sustained anti-diabetic action," J Control Release, May 2018, 277:154-164.
Glassman et al., "Toughening of Thermoresponsive Arrested Networks of Elastin-Like Polypeptides To Engineer Cytocompatible Tissue Scaffolds, " Biomacromolecules, Feb. 2016, 17, 415-426.
Gluck et al., "Single Vector System for Efficient N-myristoylation of Recombinant Proteins in *E. coli*," Plos One, Apr. 2010, 5(4) e100881.
Goke et al., "Exendin-4 is a high potency agonis and truncated exendin-(9-39)-amide an antagonist at the glucagon-like peptide 1-(7-36)-amide receptor of insulin-secreting b-cells," J. Biol. Chem. 268, 1993, 19650-19655.
Goldsmith et al., "Enzyme engineering: reaching the maximal catalytic efficiency peak," Curr Opin Struct Biol, Dec. 2017, 47:140-150.
Gordon et al., "Protein N-myristoylation," J. Biol. Chem., 1991, 266, 8647-8650.
Gosline et al., "Elastic proteins: biological roles and mechanical properties," Philos Trans R Soc Lond B Biol Sci, 2002, 357, 121-132.
Gottlieb et al., "NMR chemical shifts of common laboratory solvents as trace impurities," J. Org. Chem., 1997, 62, 7512-7515.
Goutelle et al., "The Hill equation: a review of its capabilities in pharmacological modelling. Fundam," Clin. Pharmacol. 22, Dec. 2008, 633-648.
Graff et al., "Theoretical analysis of antibody targeting of tumor spheroids: importance of dosage for penetration, and affinity for retention," Cancer Research, 2003, 63(6):1288-1296.
Gratton et al., "The effect of particle design on cellular internalization pathways," Proc Natl Acad Sci U S A, The National Academy of Sciences of the USA, Aug. 2008, 105(33):11613-8.
Greco et al., "The search for synergy: a critical review from a response surface perspective," Pharmacological Reviews, 1995, 24, 331-385.
Green et al., "Abraxane®, a novel Cremophor®-free, albumin-bound particle form of paclitaxel for the treatment of advanced non-small-cell lung cancer," Annals of Oncology, Aug. 2006, 17, 1263-1268.
Green et al., "Novel dipeptidyl peptidase IV resistant analogues of glucagon-like peptide-1(7-36) amide have preserved biological activities in vitro conferring improved glucose-lowering action in vivo" J. of Mol. Endocrin., 2003, 31(3): 529-540.
Greenfield, "Using circular dichroism spectra to estimate protein secondary structure," Nat. Protoc., Dec. 2006, 1(6):2876-90.
Griffin et al., "Accelerated wound healing by injectable microporous gel scaffolds assembled from annealed building blocks," Nat Mater, 2015, 14: 737-744.
Grimm et al., "Advances in Brachytherapy," Reviews in Urology, 2004, 6, S37-S48.
Grover et al., "Protein-Polymer Conjugates: Synthetic Approaches by Controlled Radical Polymerizations & Interesting Applications", Curr Opin Chem Bioi., Dec. 2010; 14(6): 818-827.
Gu et al., "Enzymatic Synthesis of Nucleobase-Modified Single-Stranded DNA Offers Turnable Resistance to Nuclease Degradation," Biomacromolecules, Jul. 2018, 19, 3525-3535.

(56) References Cited

OTHER PUBLICATIONS

Gu et al., "Photocontrolled micellar aggregation of amphiphilic DNA-azobenzene conjugates," Colloids Surfaces B: Biointerfaces, Nov. 2015, 135, 126-132.
Gu et al., "Precise engineering of targeted nanoparticles by using self-assembled biointegrated block copolymers," Proc Natl Acad Sci U S A, The National Academy of Sciences of the USA, Feb. 2008, 105(7):2586-91.
Güngör et al., "Pancreatic cancer," British Journal of Pharmacology, Jan. 2014, 171, 849-858.
Guo et al., "Nanoparticles escaping RES and endosome: challenges for siRNA delivery for cancer therapy," J. Nanomaterials, Aug. 2011, 2011: 1-12.
Gustafsson, "Nonlinear structured-illumination microscopy: wide-field fluorescence imaging with theoretically unlimited resolution," Proc Natl Acad Sci U S A, 2005, 102, 13081-13086.
Gustafsson, "Surpassing the lateral resolution limit by a factor of two using structured illumination microscopy," Short Communication. Journal of Microscopy, 2000, 198, 82-87.
Guzman et al., "Leiodermatolide, a novel marine natural product, has potent cytotoxic and antimitotic activity against cancer cells, appears to affect microtubule dynamics, and exhibits antitumor activity," Int. J. Cancer, Nov. 2016, 139, 2116-2126.
Gylbert, "Applanation tonometry for the evaluation of breast compressibility," Scand J Plast Reconstr Surg Hand Surg, 1989, 23: 223-229.
Ha et al., "Immunoglobulin Fc Heterodimer Platform Technology: From Design to Applications in Therapeutic Antibodies and Proteins," Front Immunol, Oct. 2016, 7(394) (in English).
Haider et al., "Genetically engineered polymers: Status and prospects for controlled release," J. Control. Release, 2004, 95, 1-26.
Halozyme Therapeutics, "PEGPH20 Plus Nab-Paclitaxel Plus Gemcitabine Compared With Nab-Paclitaxel Plus Gemcitabine in Subjects With Stage IV Untreated Pancreatic Cancer (HALO-109-202)," Clinical Trial NCT01839487 <https://clinicaltrials.gov/ct2/show/study/NCT01839487> Accessed May 29, 2018.
Hamada et al., "Novel therapeutic strategies targeting tumor-stromal interactions in pancreatic cancer," Frontiers in Physiology, Nov. 2013, vol. 4, Article 331, 7 pages.
Hamidi et al., "Pharmacokinetic Consequences of Pegylation," Drug Deliv., Dec. 2006, 13, 399-409.
Hamley, "Self-assembly of amphiphilic peptides," Soft Matter, Feb. 2011, 7, 4122.
Hampp et al., "Use of Antidiabetic Drugs in the U.S., 2003-2012," Diabetes Care, May 2014, 37: 1367-1374.
Han et al., "Survival of patients with advanced pancreatic cancer after iodine[125] seeds implantation brachytherapy: A meta-analysis," Medicine, Feb. 2017, 96, e5719.
Harmon et al., "A Model for Hysteresis Observed in Phase Transitions of Thermally Responsive Intrinsically Disordered Protein Polymers," Biophysical Journal, Feb. 2017, 112(3):207a.
Harries et al., "Nanoparticle Albumin-Bound Paclitaxel for Metastatic Breast Cancer," J. Clin. Oncol., 2005, 23(31):7768-7771.
Harris et al., "Effect of pegylation on pharmaceuticals," Nature Reviews Drug Discovery, 2003, 2: 214-221.
Harris et al., "Pegylation," Clinical Pharmacokinetics, 2001, 40(7):539-551.
Hart et al., "Attenuation of FGF signalling in mouse β-cells leads to diabetes," Nature, 2000, 408:864.
Hartgerink et al., "Self-assembly and mineralization of peptide-amphiphile nanofibers," Science, 2001, 294, 1684-8.
Hassouneh et al., "Elastin-like Polypeptide Diblock Copolymers Self-Assemble into Weak Micelles," Macromolecules, Jun. 2015, 48, 4183-4195.
Hassouneh et al., "Elastin-Like Polypeptides as a Purification Tag for Recombinant Proteins," Curr Protoc Protein Sci., Aug. 2010, Chapter 6. Unit 6.11. 10.1002/0471140864.ps0611s61.
Hassouneh et al., "Fusions of elastin-like polypeptides to pharmaceutical proteins," Methods Enzymol., Jan. 2012, 502, 215-37.

Hassouneh et al., "Unexpected Multivalent Display of Proteins by Temperature Triggered Self-assembly of Elastin-like Polypeptide Block Copolymers," Biomacromolecules, Apr. 2012, vol. 13, Issue 4, pp. 1598-1605.
Hathout et al., "Analysis of seed loss and pulmonary seed migration in patients treated with virtual needle guidance and robotic seed delivery," American journal of clinical oncology, Oct. 2011, 34, 449-453.
He et al., "Comparative genomics of elastin: Sequence analysis of a highly repetitive protein," Matrix Biology, Sep. 2007, 26:524-540.
He et al., "Improving protein resistance of α-Al2O3 membranes by modification with POEGMA brushes," Applied Surface Science, Nov. 2011, 258(3):1038-1044.
Heagerty et al., Biometrics, "Time-dependent ROC curves for censored survival data and a diagnostic marker," Jun. 2000, 56(2):337-44.
Heal et al., "N-Myristoyl transferase-mediated protein labelling in vivo," Org. Biomol. Chem., Aug. 2008, 6(13):2308-2315.
Heal et al., "Site-specific N-terminal labelling of proteins in vitro and in vivo using N-myristoyl transferase and bioorthogonal ligation chemistry," Chem. Commun., Jan. 2008, 3, 480-482.
Heggestad et al., "In Pursuit of Zero 2.0: Recent Developments in Nonfouling Polymer Brushes for Immunoassays," Adv Mater, 2020, 32: e1903285.
Heredia et al., "In Situ Preparation of Protein-"Smart" Polymer Conjugates with Retention of Bioactivity," J. Am. Chem. Soc. Jan. 2006, 127, 16955-16960.
Hermanson et al., "Peginesatide for the treatment of anemia due to chronic kidney disease—an unfulfilled promise," Expert Opin Drug Saf, 2016, 15(10): 1421-1426.
Herrero-Vanrell et al., "Self-assembled particles of an elastin-like polymer as vehicles for controlled drug release," J Control Release, 2005, 102, 113-122.
Hershfield et al., "Induced and pre-existing anti-polyethylene glycol antibody in a trial of every 3-week dosing of pegloticase for refractory gout, including in organ transplant recipients," Arthritis Res. Ther. 16, Mar. 2014, R63.
Hershfield et al., "Treating gout with pegloticase, a PEGylated urate oxidase, provides insight into the importance of uric acid as an antioxidant in vivo," Proc Natl Acad Sci U S A, 2010, 107(32): 14351-14356.
Hess et al., "Graphene Transistors for Multifunctional Polymer Brushes for Biosensing Applications," Applied Materials & Interfaces, 2014, 6: 9705-9710.
Hidalgo, "Pancreatic Cancer," N Engl J Med, Apr. 2010, 362, 1605-1617.
Hingorani et al., "Phase Ib Study of PEGylated Recombinant Human Hyaluronidase and Gemcitabine in Patients with Advanced Pancreatic Cancer," Clinical Cancer Research, Jun. 2016, 22, 2848-2854.
Ho et al., "Chemoenzymatic Labeling of Proteins for Imaging in Bacterial Cells," J. Am. Chem. Soc., Nov. 2016, 138(46):15098-15101.
Ho et al., "Internal radiation therapy for patients with primary or metastatic hepatic cancer: a review," Cancer, 1998, 83, 1894-1907.
Hober et al., "Protein A chromatography for antibody purification," Journal of Chromatography B 848, Mar. 2007, pp. 40-47.
Hochkoeppler, "Expanding the landscape of recombinant protein production in *Escherichia coli*," Biotechnol. Lett., Dec. 2013, 35, 1971-1981.
Hofmann et al., "A kinetic study on the enzymatic hydrolysis of fluoresceindiacetate and fluorescein-di-β-D-galactopyranoside," Analytical biochemistry, 1983, 131(1):180-186.
Holehouse et al., "CIDER: Classification of Intrinsically Disordered Ensemble Regions," Biophysical Journal, Feb. 2015, vol. 108, Issue 2, Supplement 1, p. 228a.
Holehouse et al.,"Functional Implications of Intracellular Phase Transitions," Biochemistry, May 2018, 57(17):2415-2423.
Holm et al., "Transperineal [125]iodine seed implantation in prostatic cancer guided by transrectal ultrasonography," The Journal of urology, 2002, 167, 985-988.

(56) References Cited

OTHER PUBLICATIONS

Hopp et al., "The effects of affinity and valency of an albumin-binding domain (ABD) on the half-life of a single-chain diabody-ABD fusion protein," Protein Engineering Design and Selection, Sep. 2010, 23(11): p. 827-834.
Hortobágyi, "Anthracyclines in the Treatment of Cancer," Drugs, 1997, vol. 54, No. 4, pp. 1-7.
Howell et al., "The MIRD Perspective 1999," J Nucl Med, 1999, 40, 3S-10S.
Hruby et al., "New bioerodable thermoresponsive polymers for possible radiotherapeutic applications," Journal of Controlled Release, May 2007, 119, 25-33.
Hruby et al., "Thermoresponsive polymeric radionuclide delivery system—an injectable brachytherapy," Eur J Pharm Sci., Feb. 2011, 42, 484-488.
Hrycushko et al., "Direct intratumoral infusion of liposome encapsulated rhenium radionuclides for cancer therapy: effects of nonuniform intratumoral dose distribution," Med Phys, Mar. 2011, 38, 1339-1347.
Hsu et al., "Fat grafting's past, present, and future: why adipose tissue is emerging as a critical link to the advancement of regenerative medicine," Aesthet Surg J, 2015, 32: 892-899.
Hu et al., "Design of tumor-homing and pH-responsive polypeptide-doxorubicin nanoparticles with enhanced anticancer efficacy and reduced side effects," Chemical Communications, Jun. 2015, 51, 11405-11408.
Hu et al., "Nanografting De Novo Proteins onto Gold Surfaces," Langmuir, 2005, vol. 21:9103-9109.
Huang et al., "Clinical features of patients infected with 2019 novel coronavirus in Wuhan," China. Lancet, 2020, 395: 497-506.
Huang et al., "Photodynamic Therapy Synergizes with Irinotecan to Overcome Compensatory Mechanisms and Improve Treatment Outcomes in Pancreatic Cancer," Cancer Research, Mar. 2016, 76, 1066-1077.
Huber et al., "Designer amphiphilic proteins as building blocks for the intracellular formation of organelle-like compartments," Nat Mater, Jan. 2015, 14(1):125-132.
Hucknall et al., "Simple Fabrication of Antibody Microarrays on Nonfouling Polymer Brushes with Femtomolar Sensitivity for Protein Analytes in Serum and Blood," Adv Mater, 2009, 21(19):1968-1971.
Huotari et al., "Endosome maturation," EMBO J, Aug. 2011, 30 (17), 3481-3500.
Hutter et al., "Calibration of atomic-force microscope tips," Review of Scientific Instruments, 1993, 64: 1868-1873.
Hwang et al., "Caprolactonic poloxamer analog: PEG-PCL-PEG," Biomacromolecules, 2005, 6, 885-890.
Hwang et al., "Differentially degradable janus particles for controlled release applications," Macromol Rapid Commun, 2012, 33: 1178-1183.
Hwang et al., "Gene therapy for primary and metastatic pancreatic cancer with intraperitoneal retroviral vector bearing the wild-type p53 gene," Surgery, 1998, 124, 143-151.
Hwang et al., "Synthesis and Characterization of Polystyrene Brushes for Organic Thin Film Transistors," Journal of Nanoscience and Nanotechnology, 2012, 12: 4137-4141.
Ibrahim et al., "Phase I and pharmacokinetic study of ABI-007, a Cremophor-free, protein-stabilized, nanoparticle formulation of paclitaxel," Clin. Cancer Res., 2002, 8 (5), 1038-1044.
Ilangovan et al., "Structure of sortase, the transpeptidase that anchors proteins to the cell wall of *Staphylococcus aureus*," Proc. Natl. Acad. Sci. 98, 2001, 6056-6061.
Inostroza-Brito et al., "Co-assembly, spatiotemporal control and morphogenesis of a hybrid protein-peptide system," Nat. Chem., Nov. 2015, 7, 1-8.
Ishida et al., "Accelerated blood clearance (ABC) phenomenon upon repeated injection of PEGylated liposomes," International Journal of Pharmaceutics, May 2008, 354(1-2):56-62.
Ito et al., "Impaired negative feedback suppression of bile acid synthesis in mice lacking βKlotho," J Clin Invest, 2005, 115(8):2202-2208.
Ito et al., "In vivo antitumor effect of the mTOR inhibitor CCI-779 and gemcitabine in xenograft models of human pancreatic cancer," International Journal of Cancer, May 2006, 118, 2337-2343.
Jacob et al., "Human phagocytes employ the myeloperoxidase-hydrogen peroxide system to synthesize dityrosine, trityrosine, pulcherosine, and isodityrosine by a tyrosyl radical-dependent pathway," J. Biol. Chem., 1996, 271, 19950-19956.
Jain, "Barriers to Drug-Delivery in Solid Tumors," Sci Am, 1994, 271, 58-65.
Jakubowski et al., "Activators regenerated by electron transfer for atom-transfer radical polymerization of (meth)acrylates and related block copolymers," Angew. Chem. Int. Ed., Jun. 2006, 4482-4486.
Janes et al., "Chitosan nanoparticles as delivery systems for doxorubicin," J. Control Release, 2001, 73, 255-267.
Jang et al., "Engineering Globular Protein Vesicles through Tunable Self-Assembly of Recombinant Fusion Proteins," Small, 2017, 13(36): 1700399.
Jenkins et al., In vivo monitoring of tumor relapse and metastasis using bioluminescent PC-3M-luc-C6 cells in murine models of human prostate cancer. Clinical & Experimental Metastasis, 2003, 20, 745-756.
Ji et al., "RGD-conjugated albumin nanoparticles as a novel delivery vehicle in pancreatic cancer therapy," Cancer Biology & Therapy, Feb. 2012, 13, 206-215.
Jia et al., "Preparation, physicochemical characterization and cytotoxicity in vitro of gemcitabine-loaded PEG-PDLLA nanovesicles," World J. Gastroenterol., Feb. 2010, 16(8):1008-1013.
Jiang et al., "Nanoparticle-mediated cellular response is size-dependent," Nat Nanotechnol, Nature Research, Mar. 2008, 3(3):145-50.
Jiang et al., "Neutralizing Antibodies against SARS-CoV-2 and Other Human Coronaviruses," Trends Immunol, 2020, 41(5): 355-359.
Jiang et al., "The internal structure of self-assembled peptide amphiphiles nanofibers," Soft Matter, Feb. 2007, 3, 454.
Jin et al., "Protein-resistant polyurethane prepared by surface-initiated atom transfer radical graft polymerization (ATRgP) of water-soluble polymers: effects of main chain and side chain lengths of grafts," Colloids and surfaces. B, Biointerfaces, Apr. 2009, 70 (1), 53-9.
Joh et al., "Architectural Modification of Conformal PEG-Bottlebrush Coatings Minimizes Anti-PEG Antigenicity While Preserving Stealth Properties," Advanced Healthcare Materials, 2019, 8(8): 1801177, 27 pages.
Joh et al., "Inkjet-printed point-of-care immunoassay on a nanoscale polymer brush enables subpicomolar detection of analytes in blood," Proc Natl Acad Sci U S A, 2017, 114: E7054-E7062.
Johansson et al., "Structure, Specificity, and Mode of Interaction for Bacterial Albumin-binding Modules," J. Biol. Chem. 2002, 277 (10), 8114-8120.
Johansson et al., "The GA module, a mobile albumin-binding bacterial domain, adopts a three-helix-bundle structure," FEBS Lett, 1995, 374(2): 257-261.
Johnson et al., "Fibroblast Growth Factor 21 Reduces the Severity of Cerulein-Induced Pancreatitis in Mice," Gastroenterology, Nov. 2009, 137(5):1795-1804.
Jokerst et al., "Nanoparticle PEGylation for imaging and therapy," Nanomedicine (Lond), Future Medicine, Jun. 2011, 6(4):715-28.
Jonsson et al., "Engineering of a femtomolar affinity binding protein to human serum albumin," Protein Engineering Design and Selection, Aug. 2008, 21(8): 515-527.
Junutula et al., "Site-specific conjugation of a cytotoxic drug to an antibody improves the therapeutic index," Nat Biotechnol, Aug. 2008, 26(8):925-932.
Jurney et al., "Unique size and shape-dependent uptake behaviors of non-spherical nanoparticles by endothelial cells due to a shearing flow," J Control Release, Jan. 2017, 245:170-176.
Kaighn et al., "Establishment and characterization of a human prostatic carcinoma cell line (PC-3)," Investigative urology, 1979, 17, 16-23.

(56) References Cited

OTHER PUBLICATIONS

Kaitin et al., "Pharmaceutical innovation in the 21st century: new drug approvals in the first decade, 2000-2009," Clin Pharmacol Ther, Feb. 2011, 89, 183-188.
Kamaly et al., "Targeted polymeric therapeutic nanoparticles: design, development and clinical translation," Chem Soc Rev, Royal Society of Chemistry, Apr. 2012, 41(7):2971-3010.
Kamisawa et al., "Pancreatic cancer," Lancet, Jul. 2016, 388, 73-85.
Kang et al., "Crystal structure of SARS-CoV-2 nucleocapsid protein RNA binding domain reveals potential unique drug targeting sites," Acta Pharm Sin B, 2020, 10(7): 1228-1238.
Kanoski et al., "The role of nausea in food intake and body weight suppression by peripheral GLP-1 receptor agonists, exendin-4 and liraglutide," Neuropharmacology 62, Apr. 2012, 1916-1927.
Kanyama et al., "Usefulness of Repeated Direct Intratumoral Gene Transfer Using Hemagglutinating Virus of Japan-Liposome Method for Cytosine Deaminase Suicide Gene Therapy," Cancer Research, 2001, 61, 14-18.
Karagoz et al., "Polymerization-Induced Self-Assembly (PISA)—control over the morphology of nanoparticles for drug delivery applications," Polym. Chem., Jan. 2014, 5(2):350-355.
Karamanolis et al., "Increased expression of VEGF and CD31 in postradiation rectal tissue: implications for radiation proctitis," Mediators Inflamm, May 2013, 515048.
Karperien, A. FracLac for Image J, version 2.5 <http://rsb.info.nih.gov/ij/plugins/fraclac/FLHelp/Introduction.htm> 1999-2012.
Kaspar et al., "Future directions for peptide therapeutics development," Drug Discovery Today, Sep. 2013, 18, 807-817.
Katakura, "Nuclear Data Sheets for A = 125," Nuclear Data Sheets, Mar. 2011, 112, 495-705.
Kataoka et al., "Block copolymer micelles for drug delivery: Design, characterization and biological significance," Advanced Drug Delivery Reviews, 2001, 47:113-131.
Kato et al., "Acidic extracellular microenvironment and cancer," Cancer Cell Int, Sep. 2013, 13, 89, 8 pages.
Katti et al., "Amino acid repeat patterns in protein sequences: Their diversity and structural- functional implications," Protein Science, 2000, 9: 1203-1209.
Keefe et al., "Poly(zwitterionic) protein conjugates offer increased stability without sacrificing binding affinity or bioactivity," Nat Chem, Jan. 2012, 4(1):59-63.
Keller et al., "Empirical Statistical Model To Estimate the Accuracy of Peptide Identifications Made by MS/MS and Database Search," Anal. Chem. 2002, 74, 5383-5392.
Kelly et al., "How to study proteins by circular dichroism," Biochim. Byophys. Acta—Proteins Proteomics, 2005, 1751(2):119-39.
Kelly et al., "Shape-specific, monodisperse nano-molding of protein particles," J Am Chem Soc, ACS Publications, Apr. 2008, 130(16):5438-9.
Kesharwani et al., "Dendrimer as nanocarrier for drug delivery," Progress in Polymer Science, Feb. 2014, 39(2):268-307.
Keten et al., "Nanoconfinement controls stiffness, strength and mechanical toughness of β-sheet crystals in silk," Nat Mater, Mar. 2010, 9, 359-367.
Khademhosseini et al., "Micromolding of photocrosslinkable hyaluronic acid for cell encapsulation and entrapment," J Biomed Mater Res A, 2006, 79: 522-532.
Khailany et al., "Genomic characterization of a novel SARS-CoV-2," Gene Rep, 2020, 9: 100682, 6 pages.
Khandare et al., "Polymer-drug conjugates: Progress in polymeric drugs," Prog. Polym. Sci., 2005, vol. 31, pp. 359-397.
Khanna et al., "The dog as a cancer model," Nat. Biotechnol., Sep. 2006, 24, 1065-1066.
Kharitonenkov et al., "FGF-21 as a novel metabolic regulator," J Clin Invest, 2005, 115(6):1627-1635.
Kharitonenkov et al., "FGF21 Revolutions: Recent Advances Illuminating FGF21 Biology and Medicinal Properties," Trends Endocrinol Metab, Nov. 2015, 26(11):608-617.
Kharitonenkov et al., "Fibroblast growth factor 21 night watch: advances and uncertainties in the field," J Intern Med, Nov. 2016, 281(3):233-246.
Kharitonenkov et al., "Inventing new medicines: The FGF21 story," Mol Metab, Jun. 2014, 3(3):221-229.
Khazov et al., "Nuclear Data Sheets for A = 131," Nuclear Data Sheets, 2006, 107, 2715-2930.
Khoo et al., "Activation of mitogen-activating protein kinase by glucose is not required for insulin secretion," Proc Natl Acad Sci USA, 1997, 94(11):5599-5604.
Khoo et al., "Regulation of Insulin Gene Transcription by ERK1 and ERK2 in Pancreatic β Cells," J Biol Chem, 2003, 278(35):32969-32977.
Kim et al., "Effects of Once-Weekly Dosing of a Long-Acting Release Formulation of Exenatide on Glucose Control and Body Weight in Subjects With Type 2 Diabetes," Diabetes Care, Jun. 2007, 30, 1487-93.
Kim et al., "Generation of core-shell microcapsules with three-dimensional focusing device for efficient formation of cell spheroid," Lab Chip, 2011, 11: 246-252.
Kim et al., "Recombinant elastin-mimetic biomaterials: Emerging applications in medicine," Adv Drug Deliv Rev, Dec. 2010, 62, 1468-1478.
Kim et al., "Site-Specific PEGylated Exendin-4 Modified with a High Molecular Weight Trimeric PEG Reduces Steric Hindrance and Increases Type 2 Antidiabetic Therapeutic Effects," Bioconjugate Chem., Nov. 2012, 23, 2214-2220.
Kim et al., "Ultrasensitive Carbon nanotube-based biosensors using antibody-binding fragments," Analytical Biochemistry, Jul. 2008, 381, 193-198.
Knop et al., "Poly(ethylene glycol) in Drug Delivery: Pros and Cons as Well as Potential Alternatives," Angewandte Chemie International Edition, Aug. 2010, 49(36):6288-6308.
Knudsen, "Glucagon-like Peptide-1: The Basis of a New Class of Treatment for Type 2 Diabetes" J. Med. Chem, 2004, 47: 4128-4134.
Kobashigawa et al., "Attachment Of An NMR-Invisible Solubility Enhancement Tag Using A Sortase-Mediated Protein Ligation Method," J Biomol NMR. Mar. 2009, vol. 43, No. 3; pp. 145-150.
Kobayashi et al., "Summary of recombinant human serum albumin development," Biologicals, Mar. 2006, 34(1): 55-59.
Koehler et al., "Albumin affinity tags increase peptide half-life In vivo," Bioorganic & Medicinal Chemistry Letters, 2002, 12(20): 2883-2886.
Kontos et al., "Drug development: longer-lived proteins," Chemical Society Reviews, Feb. 2012, 41(7):2686-2695.
Koong et al., "Phase II study to assess the efficacy of conventionally fractionated radiotherapy followed by a stereotactic radiosurgery boost in patients with locally advanced pancreatic cancer," Int J Radiation Oncol Biol Phys, 2005, 63, 320-323.
Kothare et al., "Pharmacokinetics, pharmacodynamics, tolerability, and safety of exenatide in Japanese patients with type 2 diabetes mellitus," J. Clin. Pharmacol. 48, Jan. 2009, 1389-1399.
Kowalczyk et al., "Elastin-like Polypeptides as a Promising Family of Genetically-Engineered Protein Based Polymers," World Journal of Microbiology and Biotechnology, Springer, Apr. 2014, 30(8):2141-2152.
Kozel et al., "Point-of-care testing for infectious diseases: past, present, and future," J Clin Microbiol, 2017, 55: 2313-2320.
Kozma et al., "Anti-PEG antibodies: Properties, formation, testing and role in adverse immune reactions to PEGylated nano-biopharmaceuticals, " Adv Drug Deliv Rev, 2020, 154-155, 163-175.
Kramer et al., "Quantitative Side-Chain Modifications of Methionine-Containing Elastin-Like Polypeptides as a Versatile Tool to Tune Their Properties," ACS Macro Lett., Nov. 2015, 4(11):1283-1286.
Krammer et al., "Serology assays to manage COVID-19," Science, 2020, 368: 1060-1061.
Kraulis et al., "The serum albumin-binding domain of streptococcal protein G is a three-helical bundle: a heteronuclear NMR study," FEBS letters, 1996, 378(2): p. 190-194.
Krause et al., "Structure and function of claudins," Biochmica et Biophysica Acta, Mar. 2008, 1778, 631-645.

(56) References Cited

OTHER PUBLICATIONS

Krempien et al., "Neoadjuvant chemoradiation in patients with pancreatic adenocarcinoma," HPB (Oxford), Feb. 2006, 8(1):22-28.
Kronowitz et al., "Delayed-Immediate Breast Reconstruction," Plastic and Reconstructive Surgery, 2004, 113: 1617-1628.
Kruger et al., "Analysis of the Substrate Specificity of the *Staphylococcus aureus* Sortase Transpeptidase SrtA†," Biochemistry, 2004, 43, 1541-1551.
Kulkarni et al., "Bioorthogonal Chemoenzymatic Functionalization of Calmodulin for Bioconjugation Applications," Bioconjug. Chem., Oct. 2015, 26(10):2153-2160.
Kulkarni et al., "Design of lipid nanoparticles for in vitro and in vivo delivery of plasmid DNA," Nanomedicine, May 2017, 13(4):1377-1387.
Kulkarni et al., "Selective functionalization of the protein N terminus with N-myristoyl transferase for bioconjugation in cell lysate," ChemBioChem, Oct. 2013, 14, 1958-1962.
Kumar et al., "N-Terminal Region of the Catalytic Domain of Human N-Myristoyltransferase 1 Acts as an Inhibitory Module," PLoS One, May 2015, 10(5):e0127661.
Kuo et al., "Global epidemiology of gout: prevalence, incidence and risk factors," Nature Reviews Rheumatology, 2015, 11: 649-662.
Kupelian et al., "Radical prostatectomy, external beam radiotherapy <72 Gy, external beam radiotherapy > or =72 Gy, permanent seed implantation, or combined seeds/external beam radiotherapy for stage T1-T2 prostate cancer," International journal of radiation oncology, biology, physics, 2004, 58, 25-33.
Kurosu et al., "Tissue-specific Expression of βKlotho and Fibroblast Growth Factor (FGF) Receptor Isoforms Determines Metabolic Activity of FGF19 and FGF21," J Biol Chem, Sep. 2007, 282(37):26687-26695.
Kyte et al., "A Simple Method for Displaying the Hydropathic Character of a Protein," J. Mol. Biol., 1982, 157:105-132.
Labelle et al., "Vascular endothelial cadherin promotes breast cancer progression via transforming growth factor β signaling," Cancer Res, Mar. 2008, 68, 1388-1397.
Lacroix et al., "Elucidating the folding problem of alpha-helices: local motifs, long-range electrostatics, ionic-strength dependence and prediction of NMR parameters," J Mol Biol, 1998, 284, 173-191.
Laing et al., "A dynamic COVID-19 immune signature includes associations with poor prognosis," Nat Med, 2020, 26:1623-1635.
Langer et al., "Designing materials for biology and medicine," Nature, 2004, 428, 487-92.
Laybutt et al., "Endoplasmic reticulum stress contributes to beta cell apoptosis in type 2 diabetes," Diabetologia, Apr. 2007, 50(4):752-763.
Le Droumaguet et al., "Recent advances in the design of bioconjugates from controlled/living radical polymerization," Polym. Chem. Jan. 2010, 1, 563-598.
Le Meins et al., "Hybrid polymer/lipid vesicles: State of the art and future perspectives," Mater. Today, Oct. 2013, 16, 397-402.
Leader et al., "Protein therapeutics: a summary and pharmacological classification," Nat. Rev. Drug Discov. 7, Jan. 2008, 21-39.
Lee et al., "Atomistic molecular dynamics simulations of peptide amphiphile self-assembly into cylindrical nanofibers," J. Am. Chem. Soc., Feb. 2011, 133, 3677-3683.
Lee et al., "Immunohistochemical analysis of claudin expression in pancreatic cystic tumors," Oncology Reports, Apr. 2011, 25(4): 971-978.
Lee et al., "In vivo bioluminescent imaging of irradiated orthotopic pancreatic cancer xenografts in nonobese diabetic-severe combined immunodeficient mice: a novel method for targeting and assaying efficacy of ionizing radiation," Transl. Oncol., Jun. 2010, 3, 153-159.
Lee et al., "Mechanical properties of cross-linked syntheti elastomeric polypentapeptides," Macromolecules, 2001, 34, 5968-5974.
Lee et al., "Nanoparticle-Delivered Chemotherapy: Old Drugs in New Packages." Oncology (Williston Park, NY) 31.3 (Mar. 2017): 198-208.

Lee et al., "Phase transition and elasticity of protein-based hydrogels," J. Biomater. Sci. Polymer Edn, 2001, 12, 229-242.
Lee et al., "Polymersomes for drug delivery: design, formation and characterization," J Control Release, Elsevier, Jul. 2012, 161(2):473-83.
Lee et al., "Structures of β-klotho reveal a 'zip code'-like mechanism for endocrine FGF signaling," Nature, Jan. 2018, 553:501-505.
Lee et al., "Theranostic nanoparticles with controlled release of gemcitabine for targeted therapy and MRI of pancreatic cancer," ACS Nano, Mar. 2013, 7(3):2078-2089.
Leibowitz et al., "Glucose-Regulated Proinsulin Gene Expression Is Required for Adequate Insulin Production during Chronic Glucose Exposure," Endocrinology, 2002, 143(9):3214-3220.
Lele et al., "Synthesis of uniform protein-polymer conjugates," Biomacromolecules 6, 2005, 3380-3387.
Lennen et al., "Membrane Stresses Induced by Overproduction of Free Fatty Acids in *Escherichia coli*," Appl Environ Microb., Nov. 2011, 77(22):8114-28.
Leung et al., "Bio-Click Chemistry: Enzymatic Functionalization of PEGylated Capsules for Targeting Applications**," Angew. Chem. Int. Ed. Jul. 2012, 51, 7132-7136.
Levine et al., "Thioflavine T interaction with synthetic Alzheimer's disease beta-amyloid peptides: detection of amyloid aggregation in solution," Protein Sci., 1993, 2, 404-10.
Levy et al., "Novel Exenatide Analogs with Peptidic Albumin Binding Domains: Potent Anti-Diabetic Agents with Extended Duration of Action," PLoS One, Feb. 2014, 9(2): e87704, 9 pages.
Lewis et al., "Use of digitized video microscopy with a fluorogenic enzyme substrate to demonstrate cell-and compartment-specific gene expression in *Salmonella enteritidis* and Bacillus subtilis," Molecular microbiology, 1994, 13:655-662.
Li et al., "Elastin is an essential determinant of arterial morphogenesis," Nature, 1998, 393, 276-280.
Li et al., "FGF21 Is Not a Major Mediator for Bone Homeostasis or Metabolic Actions of PPARα and PPARγ Agonists," J Bone Miner Res, Apr. 2017, 32(4):834-845.
Li et al., "Molecular description of the LCST behavior of an elastin-like polypeptide," Biomacromolecules, Aug. 2014, 15, 3522-3530.
Li et al., "Nanoparticles Evading The Reticuloendothelial System: Role of The Supported Bilayer," Biochim. Biophys. Acta, Oct. 2009, 1788 (10), 2259-2266.
Li et al., "Pancreatic cancer," Lancet, 2004, 363, 1049-1057.
Li et al., "Phase transitions in the assembly of multivalent signalling proteins," Nature, Nature Research, Mar. 2012, 483(7389):336-340.
Li et al., "Prediction of solvent-induced morphological changes of polyelectrolyte diblock copolymer micelles," Soft Matter, Nov. 2015, 11(42): 8236-45.
Li et al., "Protein adsorption on oligo(ethylene glycol)-terminated alkanethiolate self-assembled monolayers: The molecular basis for nonfouling behavior," The journal of physical chemistry. B, 2005, 109 (7), 2934-41.
Li et al., "Temperature-Triggered Phase Separation of a Hydrophilic Resilin-Like Polypeptide," Macramol. Rapid Commun., Jan. 2015, 36(1):90-95.
Li et al., "Tunable Assembly of Protein-Microdomains in Living Vertebrate Embryos," Advanced Biosystems, Oct. 2018, 2(10):1800112.
Liao et al., "Removal of N-terminal methionine from recombinant proteins by engineered *E. coli* methionine aminopeptidase," Prot. Sci. 13, 2004, 1802-1810.
Lieberman et al., "Comparison of Commercially Available and Laboratory-Developed Assays for In Vitro Detection of SARS-CoV-2 in Clinical Laboratories," J Clin Microbiol, 2020, 58(8):e00821-20.
Liechty et al., "Polymers for Drug Delivery Systems," Annual review of chemical and biomolecular engineering, Aug. 2010, 1:149-173.
Lillie et al., "The viscoelastic basis for the tensile strength of elastin," Int J Biol Macromol, 2002, 30, 119-127.
Lim et al., "Improved Non-Chromatographic Purification of a Recombinant Protein by Cationic Elastin-like Polypeptides" Biomacromolecules, May 2007, 8(5): 1417-1424.

(56) References Cited

OTHER PUBLICATIONS

Lim et al., "In situ cross-linking of elastin-like polypeptide block copolymers for tissue repair," Biomacromolecules, Feb. 2008, 9, 222-230.

Lim et al., "In vivo post-translational modifications of recombinant mussel adhesive protein in insect cells," Biotechnol. Prog., Sep.-Oct. 2011, 27(5):1390-1396.

Lin et al., "Adiponectin Mediates the Metabolic Effects of FGF21 on Glucose Homeostasis and Insulin Sensitivity in Mice," Cell Metab, May 2013, 17(5):779-789.

Lin et al., "Formation and Maturation of Phase-Separated Liquid Droplets by RNA-Binding Proteins," Mol Cell, Oct. 2015, 60(2):208-219.

Lin et al., "Functional expression of a biologically active fragment of soluble gp130 as an ELP-fusion protein in transgenic plants: purification via inverse transition cycling," Biochem J, Sep. 2006, 398(3):577-583.

Lin et al., "Intrinsically disordered sequences enable modulation of protein phase separation through distributed tyrosine motifs," J Biol Chem, Nov. 2017, 292(46):19110-19120.

Lin et al., "Phase Separation and Single-Chain Compactness of Charged Disordered Proteins Are Strongly Correlated," Biophys J, May 2017, 112(10):2043-2046.

Lin et al., "Sequence-Specific Polyampholyte Phase Separation in Membraneless Organelles," Phys Rev Lett, Oct. 2016, 117(17):178101.

Lin et al., "Statistical properties of the traditional algorithm-based designs for phase I cancer clinical trials," Biostatistics, 2001, 2(2):203-215.

Lin et al., "Utility of immunohistochemistry in the pancreatobiliary tract," Arch Pathol Lab Med, Jan. 2015, 139, 24-38.

Linder et al., "Lipid Modifications of G Protein Subunits," J. Biol. Chem., 1991, 266(7):4654-4659.

Ling et al., "Protein thioester synthesis enabled by sortase," J. Am Chem Soc, Jul. 2012, 134(26):10749-10752.

Liong et al., "Multifunctional inorganic nanoparticles for imaging, targeting, and drug delivery," ACS Nano, ACS Publications, May 2008, 2(5):889-96.

Lipsitch et al., "Antibody testing will enhance the power and accuracy of COVID-19-prevention trials," Nat Med, 2020, 26: 818-819.

Lipsky et al., "Pegloticase immunogenicity: the relationship between efficacy and antibody development in patients treated for refractory chronic gout," Arthritis Res Ther, 2014, 16: R60.

Lisboa Bastos et al., "Diagnostic accuracy of serological tests for covid-19: systematic review and meta-analysis," BMJ, 2020, 370: m2516.

Litiere et al., "Recist—learning from the past to build the future," Nat Rev Clin Oncol, Mar. 2017, 14, 187-192.

Liu et al., "Brachytherapy using injectable seeds that are self-assembled from genetically encoded polypeptides in situ," Cancer Res, Nov. 2012, 72, 5956-5965.

Liu et al., "High neutralizing antibody titer in intensive care unit patients with COVID-19," Emerg Microbes Infect, 2020, 9: 1664-1670.

Liu et al., "Hydrophobic modifications of cationic polymers for gene delivery," Prog. In Polym. Sci., Sep. 2010, 35, 1144-1162.

Liu et al., "In Situ Formation of Protein-Polymer Conjugates through Reversible Addition Fragmentation Chain Transfer Polymerization**," Angew. Chem. Int. Ed. Apr. 2007, 46, 3099-3103.

Liu et al., "Injectable intratumoral depot of thermally responsive polypeptide-radionuclide conjugates delays tumor progression in a mouse model," J. Control Release, May 2010, 144(1):2-9.

Liu et al., "Integrin $\alpha_v\beta_3$-Targeted Cancer Therapy," Drug Dev Res, Wiley, Sep. 2008, 69(6):329-339.

Liu et al., "Semi-permeable coatings fabricated from comb-polymers efficiently protect proteins in vivo," Nature Communications, 2014, 5: 5526.

Liu et al., "The experiences of health-care providers during the COVID-19 crisis in China: a qualitative study," Lancet Glob Health, 2020, 8: e790-e798.

Liu et al., "Tracking the in vivo fate of recombinant polypeptides by isotopic labeling," Journal of Controlled Release, Sep. 2006, 114, 184-192.

Liu et al., "Tumor accumulation, degradation and pharmacokinetics of elastin-like polypeptides in nude mice," Journal of Controlled Release, Nov. 2006, 116, 170-178.

Liu, L. et al., "Monodisperse core-shell chitosan microcapsules for pH-responsive burst release of hydrophobic drugs," Soft Matter, 2011, 7: 4821-4827.

Livingstone, "Theoretical property predictions. Curr Top Med Chem Field Full Journal Title: Current topics in medicinal chemistry," Curr. Top. Med. Chem. 2003, 3, 1171-1192.

Loh et al., "Utilising inorganic nanocarriers for gene delivery," Biomater Sci, Jan. 2016, 4(1):70-86.

LoPresti et al., "Polymersomes: nature inspired nanometer sized compartments," Journal of Materials Chemistry, RSC Publishing, Jun. 2009, 19(22):3576-3590.

Lovshin et al., "Incretin-based therapies for type 2 diabetes mellitus," Nat. Rev. Endocrinol. 5, Jun. 2009, 262-269.

Lu et al., "Genomic characterisation and epidemiology of 2019 novel coronavirus: implications for virus origins and receptor binding," Lancet, 2020, 395: 565-574.

Ludden, "Nonlinear pharmacokinetics: clinical Implications," Clin. Pharmacokinet., 1991, 20 (6), 429-446.

Luginbuhl et al., "One-week glucose control via zero-order release kinetics from an injectable depot of glucagon-like peptide-1 fused to a thermosensitive biopolymer," Nat. Biomed. Eng. 1, Jun. 2017, Article No. 0078.

Luginbuhl et al., "Recombinant Synthesis of Hybrid Lipid-Peptide Polymer Fusions that Self-Assemble and Encapsulate Hydrophobic Drugs," Angew Chem Int Ed Engl., Nov. 2017, 56(45):13979-13984.

Lukyanov et al., "Micelles From Lipid Derivatives of Water-Soluble Polymers as Delivery Systems for Poorly Soluble Drugs," Adv. Drug Deliver. Rev., 2004, 56(9):1273-1289.

Lukyanov et al., "Tumor-targeted liposomes: doxorubicin-loaded long-circulating liposomes modified with anti-cancer antibody," J Control Release, 2004, 100(1):135-44.

Lund et al., "Phase II study of gemcitabine (2',2'-difluorodeoxycytidine) in previously treated ovarian cancer patients," J. Natl. Cancer. Inst. 1994, 86(20):1530-1533.

Luo et al., "Noncovalent Modulation of the Inverse Temperature Transition and Self-Assembly of Elastin-b-Collagen-like Peptide Bioconjugates," J Am Chem Soc, Dec. 2015, 137, 15362-15365.

Lutz et al., "About the Phase Transitions in Aqueous Solutions of Thermoresponsive Copolymers and Hydrogels Based on 2-(2-methoxyethoxy)ethyl Methacrylate and Oligo(ethylene glycol) Methacrylate," Macromolecules, Mar. 2007, 40, 2503-2508.

Lutz et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, Jan. 2006, 39, 893-896.

Lyons et al., "Comparisons of Recombinant Resilin-like Proteins: Repetitive Domains Are Sufficient to Confer Resilin-like Properties," Biomacromolecules, ACS Publications, Oct. 2009, 10(11):3009-3014.

Lyons et al., "Design and facile production of recombinant resilin-like polypeptides: Gene construction and a rapid protein purification method," Protein Engineering Design & Selection, Oxford university Press, Jan. 2007, 20(1):25-32.

Ma et al., "Core-shell hydrogel microcapsules for improved islets encapsulation," Adv Healthc Mater, 2013, 2: 667-672.

Ma et al., "Non-fouling oligo(ethylene glycol)-functionalized polymer brushes synthesized by surface-initiated atom transfer radical polymerization," Advanced Materials 2004, 16 (4), 338.

Ma et al., "Protein-resistant polymer coatings on silicon oxide by surface-initiated atom transfer radical polymerization," Langmuir: the ACS journal of surfaces and colloids, Mar. 2006, 22 (8), 3751-6.

Ma et al., "Surface-Initiated Atom Transfer Radical Polymerization of Oligo(ethylene glycol) Methyl Methacrylate from a Mixed Self-Assembled Monolayer on Gold," Advanced Functional Materials, Mar. 2006, 16 (5), 640-648.

(56) References Cited

OTHER PUBLICATIONS

MacEwan et al., "Applications of elastin-like polypeptides in drug delivery," Journal of Controlled Release, Sep. 2014, 190: p. 314-330.

MacEwan et al., "Controlled apoptosis by a thermally toggled nanoscale amplifier of cellular uptake," Nano Letters, Apr. 2014, 14, 2058-2064.

MacEwan et al., "Digital switching of local arginine density in a genetically encoded self-assembled polypeptide nanoparticle controls cellular uptake," Nano Lett., Jun. 2012, 12, 3322-3328.

MacEwan et al., "Elastin-like polypeptides: Biomedical applications of tunable biopolymers," Biopolymers, Jan. 2010, 94, 60-77.

MacEwan et al., "Non-chromatographic Purification of Recombinant Elastin-like Polypeptides and their Fusions with Peptides and Proteins from *Escherichia coli*," Jun. 2014, 88, p. e51583.

MacEwan et al., "Phase Behavior and Self-Assembly of Perfectly Sequence-Defined and Monodisperse Multiblock Copolypeptides," Biomacromolecules, Jan. 2017, 18(2):599-609.

Mack et al., "Antiobesity action of peripheral exenatide (exendin-4) in rodents: effects on food intake, body weight, metabolic status and side-effect measures," Int. J. Obes. 30, Sep. 2006, 1332-1340.

MacKay et al., "Self-assembling chimeric polypeptide-doxorubicin conjugate nanoparticles the abolish tumors after single injection," Nat Mater, Dec. 2009, 8(12):993-999.

Maeda et al., "Tumor vascular permeability and the EPR effect in macromolecular therapeutics: a review," J. Control. Release, Mar. 2000, 65(1-2)271-284.

Maeda et al., "Tumoritropic and lymphotropic principles of macromolecular drugs," Critical reviews in therapeutic drug carrier systems, 1989, 6(3):193-210.

Maeda, "The enhanced permeability and retention (EPR) effect in tumor vasculature: the key role of tumor-selective macromolecular drug targeting," Advances in Enzyme Regulation, 2001, 41(1):189-207.

Magnusson et al., "In Situ Growth of Side-Chain PEG Polymers from Functionalized Human Growth Hormone—A New Technique for Preparation of Enhanced Protein-Polymer Conjugates," Bioconjugate Chem. 21, Mar. 2010, 671-678.

Magnusson et al., "Ion-Sensitive "Isothermal" Responsive Polymers Prepared in Water," Journal of the American Chemical Society, Aug. 2008, 130, 10852-10853.

Maitra et al., "Pancreatic Cancer," Annu Rev Pathol Mech Dis, Feb. 2008, 3, 157-188.

Malam et al., "Liposomes and nanoparticles: nanosized vehicles for drug delivery in cancer," Trends Pharmacol Sci, Cell Press, Nov. 2009, 30(11):592-9.

Malik et al., "Recent advances in protein and peptide drug delivery systems," Curr. Drug Deliv. 2, Apr. 2007, 141-151.

Manders et al., "Dynamics of three-dimensional replication patterns during the S-phase, analysed by double labelling of DNA and confocal microscopy," Journal of cell science, 1992, 103(Pt 3):857-862.

Mann et al., "Proteomic analysis of post-translational modifications," Nat. Biotechnol., 2003, 21, 255-61.

Manzoor et al., "Overcoming limitations in nanoparticle drug delivery: triggered, intravascular release to improve drug penetration into tumors," Cancer Res, Nov. 2012, 72, 5566-5575.

Mao et al., "DNA repair by nonhomologous end joining and homologous recombination during cell cycle in human cells," Cell cycle, Sep. 2008, 7, 2902-2906.

Mao et al., "Net charge per residue modulates conformational ensembles of intrinsically disordered proteins," Proc Natl Acad Sci U S A, 2010, 107(18):8183-8188.

Mao et al., "Sortase-mediated protein ligation: a new method for protein engineering," J. Am. Chem. Soc., 2004, 126(9):2670-2671.

Maraffini et al., "Sortases and the art of anchoring proteins to the envelopes of Gram-positive bacteria," Microbiol Mol Biol Rev, Mar. 2006, 70(1):192-221.

Mariam et al., "Albumin corona on nanoparticles—a strategic approach in drug delivery," Drug Deliv., Oct. 2016, 23 (8), 2668-2676.

Marr et al., "Effect of Temperature on the Composition of Fatty Acids in *Escherichia coli*," J Bacteriol., 1962, 84(6):1260-7.

Marten et al., "A randomized multicentre phase II trial comparing adjuvant therapy in patients with interferon alpha-2b and 5-FU alone or in combination with either external radiation treatment and cisplatin (CapRI) or radiation alone regarding event-free survival—CapRI-2," BMC Cancer, Feb. 2009, 9, 1-8.

Maskarinec et al., "Protein engineering approaches to biomaterials design," Curr. Opin. Biotechnol., 2005, 16, 422-426.

Masood, "Polymeric nanoparticles for targeted drug delivery system for cancer therapy," Mater Sci Eng C Mater Biol Appl, Mar. 2016, 60:569-578.

Massey et al., "Self-Assembly of a Novel Organometallic-Inorganic Block Copolymer in Solution and the Solid State: Nonintrusive Observation of Novel Wormlike Poly(ferrocenyldimethylsilane)-b-Poly(dimethylsiloxane) Micelles," J. Am. Chem. Soc. 1998, 120(37):9533-9540.

Mastria et al., "Doxorubicin-conjugated polypeptide nanoparticles inhibit metastasis in two murine models of carcinoma," J Control Release, Jun. 2015, 208:52-8.

Mastria et al., "Nanoparticle formulation improves doxorubicin efficacy by enhancing host antitumor immunity," J Control Release, Jan. 2018, 269:364-373.

Matsumura et al., "A new concept for macromolecular therapeutics in cancer chemotherapy: mechanism of tumoritropic accumulation of proteins and the antitumor agent smancs," Cancer Res. 1986, 46, 6387-6392.

Matsumura, "Cancer stromal targeting (CAST) therapy," Advanced Drug Delivery Reviews, Jun. 2012, 64, 710-719.

Matsunaga et al., "Molding cell beads for rapid construction of macroscopic 3D tissue architecture, " Adv Mater, 2011, 23: H90-94.

Matthews et al., "Pharmacodynamics, Pharmacokinetics, Safety, and Tolerability of Albiglutide, a Long-Acting Glucagon-Like Peptide-1 Mimetic, in Patients with Type 2 Diabetes," J Clin Endocrinol Metab, Dec. 2008, 93(12):4810-4817.

Matyjaszewski et al., "Atom transfer radical polymerization," Chem. Rev. 101, Sep. 2001, 2921-2990.

Matyjaszewski et al., "Macromolecular engineering by atom transfer radical polymerization," J. Am. Chem. Soc. 136, 2014, 6513-6533.

Maurer-Stroh et al., "N-terminal N-myristoylation of proteins: prediction of substrate proteins from amino acid sequence" J Mol Biol., 2002, 317(4):541-557.

Maurer-Stroh et al., "N-terminal N-myristoylation of proteins: Refinement of the sequence motif and its taxon-specific differences," J Mol Biol., 2002, 317(4):523-540.

Mayo et al., "Cell Adhesion Promoting Peptide GVKGDKGNPGWPGAP from the Collagen Type IV Triple Helix: Cis/Trans Proline-Induced Multiple 1H NMR Conformations and Evidence for a KG/PG Multiple Turn Repeat Motif in the All-Trans proline State," Biochemistry, 1991, 30: 8251- 8267.

McAndrews et al., "Heterogeneous antibodies against SARS-CoV-2 spike receptor binding domain and nucleocapsid with implications for COVID-19 immunity," JCI Insight, 2020, 5(18):e142386, 14 pages.

McConkey et al., "Molecular Characterization of Pancreatic Cancer Cell Lines," Pancreatic Cancer, Jan. 2010, 457-469.

McDaniel et al., "A unified model for de novo design of elastin-like polypeptides with tunable inverse transition temperatures," Biomacromolecules, Aug. 2013, 14(8):2866-2872.

McDaniel et al., "Actively targeting solid tumours with thermoresponsive drug delivery systems that respond to mild hyperthermia," Int J Hyperthermia, Aug. 2013, 29, 501-510.

McDaniel et al., "Doxorubicin-conjugated chimeric polypeptide nanoparticles that respond to mild hyperthermia," Control. Release, May 2012, 159 (3), 362-367.

McDaniel et al., "Drug delivery to solid tumors by elastin-like polypeptides," Adc. Drug Deliver. Rev., Dec. 2010, 62(15):1456-1467.

(56) References Cited

OTHER PUBLICATIONS

McDaniel et al., "Noncanonical Self-Assembly of Highly Asymmetric Genetically Encoded Polypeptide Amphiphiles into Cylindrical Micelles," Nano Lett., Sep. 2014, 14(11):6590-6598.
McDaniel et al., "Rational design of "heat seeking" drug loaded polypeptide nanoparticles that thermally target solid tumors," Nano Letters, Apr. 2014, 14, 2890-2895.
McDaniel et al., "Recursive Directional Ligation by Plasmid Reconstruction Allows Rapid and Seamless Cloning of Oligomeric Genes," Biomacromolecules, Feb. 2010, 11(4):944-952.
McDaniel et al., "Self-assembly of thermally responsive nanoparticles of a genetically encoded peptide polymer by drug conjugation," Chem. Int. Ed. Feb. 2013, 52, 1683-1687.
McDaniel, "Assembly of Highly Asymmetric Genetically-Encoded Amphiphiles for Thermally Targeted Delivery of Therapeutics," Dissertation, 2013, 295 pages, Published Mar. 1, 2014.
McElvaney et al., "A linear prognostic score based on the ratio of interleukin-6 to interleukin-10 predicts outcomes in COVID-19," EBioMedicine, 2020, 61: 103026, 8 pages.
McHale et al., "Synthesis and in vitro evaluation of enzymatically cross-linked elastin-like polypeptide gels for cartilaginous tissue repair," Tissue Eng., 2005, 11, 1768-1779.
McIlhinney et al., "Characterization of a polyhistidine-tagged form of human myristoyl-CoA: protein N-myristoyltransferase produced in *Escherichia coli*," European Journal of Biochemistry, 1994, 222(1):137-146.
McKenzie et al., "Multivalent Binding of a Ligand-Coated Particle: Role of Shape, Size, and Ligand Heterogeneity," Biophys J, Apr. 2018, 114(8):1830-1846.
Meier et al., "Determination of Optimal Sample Size for Quantification of β-Cell Area, Amyloid Area and β-Cell Apoptosis in Isolated Islets," J Histochem Cytochem, Aug. 2015, 63(8):663-673.
Mejía-Salazar et al., "Microfluidic Point-of-Care Devices: New Trends and Future Prospects for eHealth Diagnostics," Sensors, 2020, 20: 1951, 19 pages.
Mejuch et al., "Synthesis of lipidated proteins," Bioconjug. Chem. 27, Jul. 2016, 1771-1783.
Meng et al., "Stimuli-responsive polymersomes for programmed drug delivery," Biomacromolecules, ACS Publications, Feb. 2009, 10(2):197-209.
Merkel et al., "Using mechanobiological mimicry of red blood cells to extend circulation times of hydrogel microparticles, " Proc Natl Acad Sci U S A, The National Academy of Sciences of the USA, Jan. 2011, 108(2):586-91.
Mero et al., "Transglutaminase-mediated PEGylation of proteins: direct identification of the sites protein medification by mass spectrometry using a novel monodisperse PEG," Bioconjug Chem, Feb. 2009, 20(2):384-389.
Merriam Webster Dictionary, "Plurality," <https://www.merriam-webster.com/dictionary/plurality> webpage accessed Jun. 25, 2020.
Merrick et al., "Seed fixity in the prostate/periprostatic region following brachytherapy," International journal of radiation oncology, biology, physics, 2000, 46, 215-220.
Meyer et al., "Drug targeting using thermally responsive polymers and local hyperthermia," Journal of Controlled Release, 2001, 74, 213-224.
Meyer et al., "Genetically Encoded Synthesis of Protein-Based Polymers with Precisely Specified Molecular Weight and Sequence by Recursive Directional Ligation: Examples from the Elastin-like Polypeptide System," Biomacromolecules, 2002, 3:357-367.
Meyer et al., "Purification of recombinant proteins by fusion with thermally-responsive polypeptide," Nat. Biotechnol., 1999, 17(11):1112-1115.
Meyer et al., "Quantification of the effects of chain length and concentration on the thermal behavior of elastin-like polypeptides," Biomacromolecules, 2004, 5(3):846-51.
Meyer et al., "Targeting a Genetically Engineered Elastin-Like Polypeptide to Solid Tumors by Local Hyperthermia," Cancer Res., 2001, 61(4):1548-1554.

Miao et al., "Sequence and domain arrangements influence mechanical properties of elastin-like polymeric elastomers," Biopolymers, Jun. 2013, 99, 392-407.
Miao et al., "Structural determinants of cross-linking and hydrophobic domains for self-assembly of elastin-like polypeptides," Biochemistry, 2005, 44, 14367-14375.
Michl et al., "Current concepts and novel targets in advanced pancreatic cancer," Gut, Jan. 2013, 62, 317-326.
Micsonai et al. "Accurate secondary structure prediction and fold recognition for circular dichroism spectroscopy," Proc Natl Acad Sci U S A, Jun. 2015, 112, E3095-3103.
Milenic et al., "Antibody-targeted radiation cancer therapy," Nature Reviews Drug Discovery, 2004, 3, 488-498.
Miller et al., "Disease and healthcare burden of COVID-19 in the United States," Nat Med, 2020, 26: 1212-1217.
Miller et al., "Solubilized, Spaced Polyalanines: A Context-Free System for Determining Amino Acid α-Helix Propensities," Journal of the American Chemical Society, 2002, 124, 945-962.
Minteer et al., "Fat Grafting for Pedal Fat Pad Atrophy in a 2-Year, Prospective, Randomized, Crossover, Single-Center Clinical Trial," Plast Reconstr Surg, 2018, 142: 862e-871e.
Mitragotri et al., "Physical approaches to biomaterial design," J. Nat Mater, Nature Publishing Group, Jan. 2009, 8(1):15-23.
Miyata et al., "Polymeric micelles for nano-scale drug delivery," Reaction & Functional Polymers, Mar. 2011, 71, 227-234.
Mjelle et al., "Cell cycle regulation of human DNA repair and chromatin remodeling genes," DNA Repair, Jun. 2015, 30, 53-67.
Modery et al., "Heteromultivalent liposomal nanoconstructs for enhanced targeting and shear-stable binding to active platelets for site-selective vascular drug delivery," Biomaterials, Elsevier, Dec. 2011, 32(35):9504-9514.
Molliex et al., "Phase separation by low complexity domains promotes stress granule assembly and drives pathological fibrillization," Cell, Sep. 2015, 163(1):123-133.
Moosmann et al., "Alpha complementation of LacZ in mammalian cells," Nucleic Acids Res, 1996, 24(6):1171-1172.
Morgan et al., "The combination of epidermal growth factor receptor inhibitors with gemcitabine and radiation in pancreatic cancer," Clin Cancer Res, Aug. 2008, 14, 5142-5149.
Mosbach et al., "Formation of proinsulin by immobilized Bacillus subtilis," Nature, 1983, 302, 543-545.
Mozhdehi et al., "Genetically Encoded Cholesterol-Modified Polypeptides," Journal of the American Chemical Society, Jan. 2019, 141(2):945-951.
Mozhdehi et al., "Genetically encoded lipid-polypeptide hybrid biomaterials that exhibit temperature-triggered hierarchical self-assembly," Nature chemistry, May 2018, 10(5):496-505.
Mu et al., "FGF21 Analogs of Sustained Action Enabled by Orthogonal Biosynthesis Demonstrate Enhanced Antidiabetic Pharmacology in Rodents," Diabetes, Feb. 2012, 61(2):505-512.
Muiznieks et al., "Modulated growth, stability and interactions of liquid-like coacervate assemblies of elastin," Matrix Biology 36, Jun. 2014, pp. 39-50.
Muiznieks et al., "Proline periodicity modulates the self-assembly properties of elastin-like polypeptides," J Biol Chem, The American Society for Biochemistry and Molecular Biology, Inc, Dec. 2010, 285(51):39779-39789.
Muiznieks et al., "Structural changes and facilitated association of tropoelastin," Archives of Biochemistry and Biophysics, 2003, 410, 317-323.
Muñoz et al., "Elucidating the folding problem of helical peptides using empirical parameters," Nature Structural Biology, 1994, 1, 399-409.
Muñoz et al., "Elucidating the Folding Problem of Helical Peptides using Empirical Parameters. II†. Helix Macrodipole Effects and Rational Modification of the Helical Content of Natural Peptides," Journal of Molecular Biology, 1995, 245, 275-296.
Muñoz et al., "Elucidating the folding problem of helical peptides using empirical parameters. III. Temperature and pH dependence," J Mol Biol, 1995, 245, 297-308.
Muralidharan et al., "Protein Ligation: an Enabling Technology for the Biophysical Analysis of Proteins," Nature Methods, Jun. 2006, vol. 3, No. 6, pp. 429-438.

(56) References Cited

OTHER PUBLICATIONS

Muro, "Challenges in design and characterization of ligand-targeted drug delivery systems," J Control Release, Elsevier, Dec. 2012, 164(2):125-37.
Murphy et al., "A dosimetric model of duodenal toxicity after stereotactic body radiotherapy for pancreatic cancer," Int J Radiation Oncology Biol Phys, Dec. 2010, 78, 1420-1426.
Na et al., "Thermoresponsive pore structure of biopolymer microspheres for a smart drug carrier," Langmuir, Jun. 2010, 26, 11165-11169.
Nagarsekar et al., "Genetically Engineered Polymers for Drug Delivery," Journal of Drug Targeting, 1999, 7(1):11-32.
Nahire et al., "Multifunctional Polymersomes for Cytosolic Delivery of Gemcitabine and Doxorubicin to Cancer Cells," Biomaterials, Aug. 2014, 35(24):6482-6497.
Nairn et al., "A Synthetic Resilin Is Largely Unstructured," Biophysical Journal, Oct. 2008, vol. 95 3358-3365.
Nakaoka et al., "Prolongation of the serum half-life period of superoxide dismutase by poly(ethylene glycol) modification," Journal of Controlled Release, 1997, 46(3):253-261.
Nalla et al., "Comparative Performance of SARS-CoV-2 Detection Assays Using Seven Different Primer-Probe Sets and One Assay Kit," J Clin Microbiol, 2020, 58: e00557-20, 6 pages.
Nanoprecision Medical, "Pipeline, Type II Diabetes," <http://www.nanoprecisionmedical.com/pipeline/diabetes> webpage available as early as Aug. 2018.
Napier et al., "Nanoparticle drug delivery platform," Journal of Macromolecular Science, Part C: Polymer Reviews, Taylor & Francis Group, LLC, Aug. 2007, 47(3):321-327.
National Institute of Mental Health, "Methods and Welfare Considerations in Behavioral Research with Animals: Report of a National Institutes of Health Workshop," NIH Publication No. 02-54083, Washington, DC: U.S. Government Printing Office. (Mar. 2002).
Nauck "Glucagon-like Peptide 1 (GLP-1) in the Treatment of Diabetes," Horm Metab Res, 2004, 36(11/12):852-858 (in English).
Nayeem et al., "Engineering enzymes for improved catalytic efficiency: a computational study of site mutagenesis in epothilone-B hydroxylase," Protein Eng Des Sel, Oxford Academy, Apr. 2009, 22(4):257-266.
Neidigh et al., "Exendin-4 and glucagon-like-peptide-q: NMR structural comparisons in the solution and micelle-associated states," Biochemistry 40, 2001, 13188-13200.
Nettles et al., "Applications of elastin-like polypeptides in tissue engineering," Adv Drug Deliv Rev, Dec. 2010, 62, 1479-1485.
Nettles et al., "In situ crosslinking elastin-like polypeptide gels for application to articular cartilage repair in a goat osteochondral defect model," Tissue Eng Part A, Jul. 2008, 14, 1133-1140.
Newcomb et al., "Advances in cryogenic transmission electron microscopy for the characterization of dynamic self-assembling nanostructures," Current Opinion in Colloid and Interface Science, Dec. 2012, 17, 350-359.
Newton et al., "Commissioning a small-field biological irradiator using point, 2D, and 3D dosimetry techniques," Medical Physics, Dec. 2011, 38, 6754-6762.
Ni et al., "Engineering of inorganic nanoparticles as magnetic resonance imaging contrast agents," Chem Soc Rev, Nov. 2017, 46(23):7438-7468.
Nichols et al., "Claudin 4 protein expression in primary and metastatic pancreatic cancer," Am J Clin Pathol, 2004, 121, 226-230.
Nicolas et al., "Fluorescently tagged polymer bioconjugates from protein derived macroinitiators," Chem. Commun. Jan. 2007, 45, 4697-4699.
Nie, "Understanding and overcoming major barriers in cancer nanomedicine," Nanomedicine (Lond) Jun. 2010, 5 (4), 523-528.
Nielsen, "Incretin mimetics and DPP-IV inhibitors for the treatment of type 2 diabetes," Drug Discov. Today 10, 2005, 703-710.
Nies et al., "Fibroblast Growth Factor Signaling in Metabolic Regulation," Front Endocrinol, Jan. 2016, 6(193) (in English).

Nikolic et al., "Structural basis for the recognition of LDL-receptor family members by VSV glycoprotein," Nature Communications, 2018, 9: 1029, 12 pages.
Nilvebrant et al., "The albumin-binding domain as a scaffold for protein engineering," Computational and Structural Biotechnology Journal, Mar. 2013, 6: e201303009, 8 pages.
Niu et al., "The role of adhesion molecules, αvB3, αvB5 and their ligands in the tumor cell and endothelial cell adhesion," Eur J Cancer Prev, Wolters Kluwer, Dec. 2007, 16(6):517-27.
Norman et al., "Ultrasensitive high-resolution profiling of early seroconversion in patients with COVID-19," Nat Biomed Eng, 2020, 11 pages.
Nott et al., "Phase transition of a disordered nuage protein generates environmentally responsive membraneless organelles," Mol Cell, Mar. 2015, 57(5):936-947.
Nucci et al., "The therapeutic value of poly(ethylene glycol)-modified proteins," Adv. Drug Deliv. Rev., 1991, 6(2):133-151.
Nuhn et al., "Secondary structure formation and LCST behavior of short elastin-like peptides," Biomacromolecules, Sep. 2008, 9, 2755-2763.
Nunn et al., "Crystal Structure of Tobacco Etch Virus Protease Shows the Protein C Terminus Bound within the Active Site," Journal of Molecular Biology, 2005, 350: 145-155.
Nyborg et al., "A Therapeutic Uricase with Reduced Immunogenicity Risk and Improved Development Properties," PLoS One, 2016, 11(12): e0167935, 23 pages.
O'Day et al., "Therapeutic Protein-polymer Conjugates: Advancing beyond PEGylation," J. Am. Chem. Soc., Sep. 2014, vol. 136, pp. 14323-14332.
Ogawara et al., "Pre-coating with serum albumin reduces receptor-mediated hepatic disposition of polystyrene nanosphere: implications for rational design of nanoparticles," Journal of Controlled Release, 2004, 100(3): 451-455.
Oh et al., "The development of microgels/nanogels for drug delivery applications," Progress in Polymer Science, 2008, 33(4): 448-477.
Okba et al., "Severe Acute Respiratory Syndrome Coronavirus 2-Specific Antibody Responses in Coronavirus Disease Patients," Emerg Infect Dis, 2020, 26: 1478-1488.
Olafsen et al., "Covalent disulfide-linked anti-CEA diabody allows site-specific conjugation and radiolabeling for tumor targeting applications," Protein Engineering, Design & Selection, 2004, 17(1):21-27.
Ortega et al., "Hydrodynamic properties of rodlike and dislike particles in dilute solution," The Journal of Chemical Physics, 2003, 119(18):9914-9919.
Ortony et al., "Internal dynamics of a supramolecular nanofibre," Nat. Mater., Aug. 2014, 13, 1-5.
Ozer et al., "Effect of Molecular Architecture on Cell Interactions and Stealth Properties of PEG," Biomacromolecules, 2017, 18: 2699-2710.
Ozer et al., "Site-Specific and Stoichiometric Stealth Polymer Conjugates of Therapeutic Peptides and Proteins," Bioconjug Chem, Mar. 2017, 28(3):713-723.
Pace et al., "How to measure and predict the molar absorption coefficient of a protein" Protein Science 1995, 4: 2411-2423.
Pagani et al., "International guidelines for management of metastatic breast cancer: can metastatic breast cancer be cured?," Journal of the National Cancer Institute, Apr. 2010, 102, 456-463.
Pak et al., "Sequence Determinants of Intracellular Phase Separation by Complex Coacervation of a Disordered Protein," Mol Cell, Jul. 2016, 63(1):72-85.
Palmerston Mendes et al., "Dendrimers as Nanocarriers for Nucleic Acid and Drug Delivery in Cancer Therapy," Molecules, Aug. 2017, 22(9):1401.
Palta et al., "Interim Acute Toxicity Analysis and Surgical Outcomes of Neoadjuvant Gemcitabine/nab-Paclitaxel and Hypofractionated Image Guided Intensity Modulated Radiation Therapy in Resectable and Borderline Resectable Pancreatic Cancer (ANCHOR) Study," International Journal of Radiation Oncology • Biology • Physics, Oct. 2016, 96, S204-S205.
Palva et al., "Secretion of interferon by Bacillus subtilis," Gene, 1983, 22, 229-235.

(56) References Cited

OTHER PUBLICATIONS

Pan et al., "A Pig Model for the Histological Analysis of Adipocytes after Co-injections of Autologous Fat with Fillers," International Journal of Surgery & Surgical Techniques, 2016, 2: 7 pages.
Panda et al., "Stop-flow lithography to generate cell-laden microgel particles," Lab Chip, 2008, 8: 1056-1061.
Pang et al., "A Modular Method for the High-Yield Synthesis of Site-Specific Protein-Polymer Therapeutics," Angew Chem Int Ed Engl, Jul. 2016, 55, 10296-10300.
Paolino et al., "Folate-targeted supramolecular vesicular aggregates as a new frontier for effective anticancer treatment in in vivo model," Eur. J. Pharm. Biopharm., Jun. 2012, 82(1):94-102.
Paolino et al., "Gemcitabine-loaded PEGylated unilamellar liposomes vs GEMZAR: biodistribution, pharmacokinetic features and in vivo antitumor activity," J. Control. Release Jun. 2010, 144(2):144-150.
Paoloni et al., "Translation of new cancer treatments from pet dogs to humans," Nat. Rev. Cancer Feb. 2008, 8 (2), 147-156.
Papa et al., "PEGylated Liposomal Gemcitabine: Insights Into a Potential Breast Cancer Therapeutic," Cell Oncol. (Dordr), Oct. 2013, 36(6):449-457.
Paramonov et al., "Self-assembly of peptide-amphiphile nanofibers: The roles of hydrogen bonding and amphiphilic packing," J. Am. Chem. Soc., May 2006, 128, 7291-7298.
Pardridge, "The blood-brain barrier: bottleneck in brain drug development," NeuroRx, 2005, 2(1):3-14.
Park et al., "Exendin-4 and exercise improve hepatic glucose homeostasis by promoting insulin signaling in diabetic rats," Metabolism, Jan. 2010, 59, 123-133.
Park et al., "Formulation optimization and in vivo proof-of-concept study of thermosensitive liposomes balanced by phospholipid, elastin-like polypeptide, and cholesterol," PLoS One, Jul. 2014, 9: e103116, 13 pages.
Park et al., "Polymer Brush As a Facile Dielectric Surface Treatment for High-Performance, Stable, Soluble Acene-Based Transistors," Chemistry of Materials, 2010, 22: 5377-5382.
Park et al., "Protein stitchery: Design of a protein for selective binding to a specific DNA sequence," PNAS, 1992, vol. 89:9094-9096.
Parker et al., "Antibody mimics based on human fibronectin type three domain engineered for thermostability and high-affinity binding to vascular endothelial growth factor receptor two," Protein Eng Des Sel, 2005, 18(9):435-44.
Parkes et al. "Discovery and development of exenatide: the first antidiabetic agent to leverage the multiple benefits of the incretin hormone, GLP-1," Expert Opinion. Drug Deliv., Feb. 2013, 8(2):219-244.
Parveen et al., "Nanomedicine," Clinical Pharmacokinetics, Oct. 2006, 45(10):965-988.
Pastuszka et al., "A tunable and reversible platform for the intracellular formation of genetically engineered protein microdomains," Biomacromolecules, ACS Publications, Oct. 2012, 13(11):3439-3444.
Patil et al., "Cellular delivery of doxorubicin via pH-controlled hydrazone linkage using multifunctional nano vehicle based on poly(beta-I-malic acid)," Int J Mol Sci, Sep. 2012, 13, 11681-11693.
Paulsen et al., "Optofluidic fabrication for 3D-shaped particles," Nat Commun, 2015, 6: 6976.
Pecoraro et al., "A systematic evaluation of immunoassay point-of-care testing to define impact on patients' outcomes," Ann Clin Biochem, 2017, 54(4): 420-431.
Peeler et al., "Genetically encoded initiator for polymer growth from proteins," J. Am. Chem. Soc. 132, Oct. 2010, 13575-13577.
Peng et al., "Length-dependent prediction of protein intrinsic disorder," BMC Bioinformatics, Springer Nature, Apr. 2006, 7:208.
Peters, "Serum albumin," Adv. Protein Chem. 37, 1985, 161-245.
Petitdemange et al., "Tuning Thermoresponsive Properties of Cationic Elastin-like Polypeptides by Varying Counterions and Side-Chains," Bioconjug. Chem., May 2017, 28(5):1403-1412.

Petros et al., "Strategies in the design of nanoparticles for therapeutic applications," Nat Rev Drug Discov, Nature Research, Aug. 2010, 9(8):615-27.
Phan et al., "Temperature-responsive self-assembly of charged and uncharged hydroxyethylcellulose-graft-poly(N-isopropylacrylamide) copolymer in aqueous solution," Colloid Polym. Sci., Apr. 2011, 289 (9), 993-1003.
Pinkas et al., "Tunable, post-translational hydroxylation of collagen domains in *Escherichia coli*," ACS Chem. Biol., Apr. 2011, 6(4):320-324.
Pliarchopoulou et al., "Pancreatic cancer: Current and future treatment strategies," Cancer Treatment Reviews, Aug. 2009, 35, 431-436.
Poitout et al., "Glucolipotoxicity: Fuel Excess and β-Cell Dysfunction," Endocr Rev, May 2008, 29(3):351-366.
Pometun et al., "Quantitative observation of backbone disorder in native elastin," J Biol Chem, 2004, 279, 7982-7987.
Ponti et al., "Biomarkers associated with COVID-19 disease progression," Crit Rev Clin Lab Sci, 2020, 57, 11 pages.
Popp et al., "Site-specific labeling via sortase-mediated transpeptidation," Curr. Protoc. Protein Sci. 56, Apr. 2009, 15.13.1-15.13.9.
Popp et al., "Sortase-Catalyzed Transformations That Improve The Properties Of Cytokines," PNAS, Feb. 2011, vol. 108, No. 8, pp. 3169-3174.
Posthuma-Trumpie et al., "Lateral flow (immuno)assay: its strengths, weaknesses, opportunities and threats. A literature survey," Anal Bioanal Chem, 2009, 393: 569-582.
Potters et al., "12-year outcomes following permanent prostate brachytherapy in patients with clinically localized prostate cancer," The Journal of urology, 2005, 173, 1562-1566.
Potters et al., "Monotherapy for stage T1-T2 prostate cancer: radical prostatectomy, external beam radiotherapy, or permanent seed implantation," Radiotherapy and oncology: journal of the European Society for Therapeutic Radiology and Oncology, 2004, 71, 29-33.
Potters et al., "Potency after permanent prostate brachytherapy for localized prostate cancer," International journal of radiation oncology, biology, physics, 2001, 50(5): 1235-1242.
Potthoff et al., "Endocrine fibroblast growth factors 15/19 and 21: from feast to famine," Genes Dev, Feb. 2012, 26(4):312-324.
Prestwich et al., "Beta dose point kernels for radionuclides of potential use in radioimmunotherapy," J Nucl Med, 1989, 30, 1036-1046.
Privratsky et al., "PECAM-1: regulator of endothelial junctional integrity," Cell Tissue Res, Mar. 2014, 355, 607-619.
Prostate Seed Center, "Brachytherapy seed pre-plan rendering," <http://www.prostateseedcenter.com/dynamics-of-brachytherapy> webpage available as early as Aug. 30, 2012.
Provenzano et al., "Enzymatic targeting of the stroma ablates physical barriers to treatment of pancreatic ductal adenocarcinoma," Cancer cell, Mar. 2012, 21, 418-429.
Provenzano et al., "Hyaluronan, fluid pressure, and stromal resistance in pancreas cancer," Br J Cancer, Jan. 2013, 108, 1-8.
Pulaski et al., "Mouse 4T1 breast tumor model," Curr. Protoc. Immunol., 2001, Chapter 20, Unit 20.2.
Qamar et al., "FUS Phase Separation Is Modulated by a Molecular Chaperone and Methylation of Arginine Cation-pi Interactions," Cell, Apr. 2018, 173(3):720-734.e15.
Qi et al., "A brush-polymer conjugate of exendin-4 reduces blood glucose for up to five days and eliminates poly(ethylene glycol) antigenicity," Nat Biomed Eng, Nov. 2016, 1:0002.
Qi et al., Dataset for A brush-polymer conjugate of exendin-4 reduces blood glucose for up to five days and eliminates poly(ethylene glycol) antigenicity. Figshare, Nov. 2016, <http://dx.doi.org/10.6084/m9.figshare.3976761>.
Qi et al., "Growing polymers from peptides and proteins: a biomedical perspective," Polym. Chem., Jan. 2014, 5(2):266-276.
Qi et al., "Protein-polymer conjugation—moving beyond PEGylation," Curr. Opin. Chem. Biol. 28, Oct. 2015, 181-193.
Qi et al., "Sortase-catalyzed initiator attachment enables high yield growth of a stealth polymer from the C terminus of a protein," Macromol. Rapid Commun., Aug. 2013, 34(15):1256-1260.
Qiu et al., "Development of Orthotopic Pancreatic Tumor Mouse Models," Methods Mol Biol, Jan. 2013, 980: 215-223.

(56) References Cited

OTHER PUBLICATIONS

Qiu et al., "Polymer Architecture and Drug Delivery," Pharmaceutical Research, Feb. 2006, 23(1):1-30.
Quarmby et al., "Irradiation induces upregulation of CD31 in human endothelial cells," Arterioscler Thromb Vasc Biol, 1999, 19, 588-597.
Quarmby et al., "Radiation-induced normal tissue injury: role of adhesion molecules in leukocyte-endothelial cell interactions," Int J Cancer, 1999, 82, 385-395.
Quiroz et al., "Intrinsically disordered proteins access a range of hysteretic phase separation behaviors," Scientific advances, Oct. 2019, 5(10):eaax5177.
Quiroz et al., "Sequence heuristics to encode phase behaviour in intrinsically disordered protein polymers," Nat. Mater., Nov. 2015, 14(11):1164-1171.
Rabotyagova et al., "Protein-based block copolymers," Biomacromolecules, Feb. 2011, 12(2): 269-289.
Radivojac et al., "Intrinsic Disorder and Functional Proteomics," Biophysical Journal, Mar. 2007, vol. 92, Issue 5, pp. 1439-1456.
Radzicka et al., "Comparing the Polrities of the Amino Acids: Side-Chain Distribution Coefficients between the Vapor Phase, Cyclohexane, 1-Octanol, and Neutral Aqueous Solution," Biochemistry, 1988, 27: 1664-1670.
Ragupathi et al., "Abstract A73: Antitumor activity of MVT-5873, a monoclonal antibody targeting sialyl Lewisa, alone and in combination with gemcitabine/nab-paclitaxel in a BxPC3 human pancreatic cancer xenograft model," Cancer Research, Dec. 2016, 76.
Rankine et al., "Investigating end-to-end accuracy of image guided radiation treatment delivery using a micro-irradiator," Physics in Medicine and Biology, Nov. 2013, 58(21): 7791-7801.
Rao et al., "Synthetic nanoparticles camouflaged with biometric erythrocyte membranes for reduced reticuloendothelial system uptake," Nanotechnology, Jan. 2016, 27 (8), 85106, 9 pages.
Rapaka et al., "Coacervation of Sequential Polypeptide Models of Tropoelastin," Int J Peptide Protein Res, 1978, 11: 97-108.
Rasmussen et al., "A Novel Porcine Model for Future Studies of Cell-enriched Fat Grafting," Plast Reconstr Surg Glob Open, 2018, 6: e1735.
Ratner et al., "Radiation-grafted hydrogels for biomaterial applications as studied by the ESCA technique," Journal of Applied Polymer Science, 1978, 22, 643-664.
Ratner, "A pore way to heal and regenerate: 21st century thinking on biocompatibility," Regen Biomater, Feb. 2016, 3(2):107-110.
Rauscher et al. "Proline and Glycine Control Protein Self-Organization into Elastomeric or Amyloid Fibrils," Structure, Nov. 2006, 14(11):1667-1676.
Ravichandran et al., "Antibody signature induced by SARS-CoV-2 spike protein immunogens in rabbits," Sci Transl Med, 2020, 10.1126/scitranslmed.abc3539, 9 pages.
Ravikumar et al., "Mimicking adhesive functionalities of blood platelets using ligand-decorated liposomes," Bioconjugate chemistry, ACS Publications, May 2012, 23(6):1266-1275.
Ray et al., "Aptamer-mediated delivery of chemotherapy to pancreatic cancer cells." Nucleic acid therapeutics, Oct. 2012, 22(5): 295-305.
Regier et al., American Heart Association 2014 Scientific Sessions, May 2015, vol. 7, pp. 299-303.
Reguera et al., "Thermal Behavior and Kinetic Analysis of the Chain Unfolding and Refolding and of the Concomitant Nonpolar Solvation and Desolvation of Two Elastin-like Polymers," Macromolecules, 2003, 36, 8470-8476.
Ren et al., "Mesenchymal stem cell-mediated immunosuppression occurs via concerted action of chemokines and nitric oxide," Cell Stem Cell, Feb. 2008, 2(2): p. 141-150.
Resh, "Covalent Lipid Modifications of Proteins," Curr Biol., May 2013, 23(10): R431-R435.
Ribeiro et al., "Influence of the amino-acid sequence on the inverse temperature transition of elastin-like polypeptides," Biophysical Journal, Jul. 2009, 97(1):312-320.
Richards et al., "Engineered fibronectin type III domain with a RGDWE sequence binds with enhanced affinity and specificity to human avβ3 integrin," J Mol Biol, 2003, 326(5):1475-1488.
Richards et al., "Man's best friend: what can pet dogs teach us about non-Hodgkin lymphoma?" Inmunol Rev., Jan. 2015, 263 (1): 173-191.
Riddles et al., "Ellman's reagent: 5,5'-dithiobis(2-nitrobenzoic acid)—a reexamination," Anal Biochem. 1979, 94(1):75-81.
Riedel et al., "Engineered glucagon-like peptide-1-producing hepatocytes lower plasma glucose levels in mice," Am J Physiol Endocrinol Metab, Apr. 2009, 296(4):E936-E944.
Rincon et al., "Biocompatibility of elastin-like polymer poly(VPAVG) microparticles: in vitro and in vivo studies," Journal of Biomedical Materials Research, 2005, 78A, 343-351.
Rios-Doria et al., "Doxil synergizes with cancer immunotherapies to enhance antitumor responses in syngeneic mouse models," Neoplasia, Aug. 2015, 17(8):661-670.
Ritcher et al., "Antibodies against polyethylene glycol produced in animals by immunization with monomethoxy polyethylene glycol modified proteins," Int. Arch. Allergy Appl. Immunol. 70, 1983, 124-131.
Ritcher et al., "Polyethylene glycol reactive antibodies in man: titer distribution in allergic patients treated with monomethoxy polyethylene glycol modified allergens or placebo, and in healthy blood donors," Int. Arch. Allergy Appl. Immunol. 74, 1984, 36-39.
Rivory et al., "Effects of lipophilicity and protein binding on the hepatocellular uptake and hepatic disposition of two anthracyclines, doxorubicin and iododoxorubicin," Cancer Chemother Pharmacol, 1996, 38(5):439-445.
Roberts et al., "Elastin-like polypeptides as models of intrinsically disordered proteins," FEBS Lett., Sep. 2015, 589, 2477-2486.
Roberts et al., "Injectable tissue integrating networks from recombinant polypeptides with tunable order," Nature Materials, 2018, 17(12): 1154-1163.
Robinet et al. "Elastin-derived peptides enhance angiogenesis by promoting endothelial cell migration and tubulogenesis through upregulation of MT1-MMP," J. Cell Science, 2005, 118:343-356.
Roca et al., "Autologous Fat Grafting for Treatment of Breast Implant Capsular Contracture: A Study in Pigs," Aesthet Surg J, 2014, 34: 769-775.
Rodriguez-Cabello et al., "Elastin-like polypeptides in drug delivery," Adv Drug Deliv Rev, 2016, 97: 85-100.
Rodriguez-Diaz et al., "Alpha cells secrete acetylcholine as a non-neuronal paracrine signal priming beta cell function in humans," Nat Med, Jun. 2011, 17:888-892.
Rogers et al., "Isolation of potent SARS-CoV-2 neutralizing antibodies and protection from disease in a small animal model," Science, 2020, 369: 956-963.
Rolland et al., "Direct fabrication and harvesting of monodisperse, shape-specific nanobiomaterials," J Am Chem Soc, 2005, 127(28):10096-100.
Romer et al., "The elaborate structure of spider silk: structure and function of a natural high performance fiber," Prion, Nov. 2008, 2(4):154-161.
Roopenian et al., "FcRn: the neonatal Fc receptor comes of age," Nat. Rev. Immunol., Sep. 2007, vol. 7, No. 9, 715-725.
Rosadas et al., "Testing for responses to the wrong SARS-CoV-2 antigen," Lancet, 2020, 396: e23.
Rosenberg et al., "Present and future innovations in radiation oncology," Surg Oncol Clin N Am, Jul. 2013, 22(3):599-618.
Rosenholm et al., "Towards multifunctional, targeted drug delivery systems using mesoporous silica nanoparticles—opportunities & challenges," Nanoscale, Royal Society of Chemistry, Oct. 2010, 2(10):1870-83.
Rösler et al., "Advanced drug delivery devices via self-assembly of amphiphilic block copolymers," Advanced Drug Delivery Reviews, 2001, 53:95-108.
Rothe et al., "Transmission of 2019-nCoV Infection from an Asymptomatic Contact in Germany," N Engl J Med, 2020, 382: 10, 2 pages.

(56) References Cited

OTHER PUBLICATIONS

Rozak et al., "G148-GA3: a streptococcal virulence module with atypical thermodynamics of folding optimally binds human serum albumin at physiological temperatures," Biochim Biophys Acta, 2005, 1753(2): p. 226-33.

Ruiz van Haperen et al., "Regulation of phosphorylation of deoxycytidine and 2',2'-difluorodeoxycytidine (gemcitabine); effects of cytidine 5'-triphosphate and uridine 5'- triphosphate in relation to chemosensitivity for 2', 2'-difluorodeoxycytidine," Biochem. Pharmacol. 1996, 51(7):911-908.

Russo et al., "The role of neoadjuvant therapy in pancreatic cancer: a review," Future Oncol, Mar. 2016, 12(5):669-685.

Ryerson et al., "Annual report to the nation on the status of cancer, 1975-2012, featuring the Increasing incidence of liver cancer," Cancer, May 2016, 122(9): 1312-1337.

Ryu et al., "Elastin-like polypeptide for improved drug delivery for anticancer therapy: preclinical studies and future applications," Expert Opinion on Drug Delivery, Informa Healthcare, Oct. 2014, 12(4):653-667.

Saba et al., "A Comparative Oncology Study of Iniparib Defines Its Pharmacokinetic Profile and Biological Activity in a Naturally-Occurring Canine Cancer Model," PLoS One, Feb. 2016, 11(2): 1-11.

Safran et al., "Gemcitabine, paclitaxel, and radiation for locally advanced pancreatic cancer: A phase I trial," Int J Radiation Oncology Biol Phys, 2002, 54, 137-141.

Sagle et al., "Investigating the hydrogen-bonding model of urea denaturation," J Am Chem Soc, Jun. 2009, 131(26): 9304-9310.

Saifer et al., "Selectivity of binding of PEGs and PEG-like oligomers to anti-PEG antibodies induced by methoxyPEG-proteins," Molecular Immunology, Feb. 2014, 57(2):236-246.

Sandberg et al., "The Structure of the Elastic Fiber: An Overview," The Journal of Investigative Dermatology, 1982, 79(S1): 128s-132s.

Sandler et al., "Gemcitabine: Single-Agent and Combination Therapy in Non-Small Cell Lung Cancer," Oncologist 1999, 4(3)241-251.

Sanna et al., "Targeted therapy using nanotechnology: focus on cancer," Int J Nanomedicine, Jan. 2014, 9:467-83.

Schaal et al., "Biopolymer β-brachytherapy delivered with concomitant paclitaxel outperforms traditional x-ray radiation to include complete regression in multiple pancreatic tumor xenograft models through synergistic modulation of the tumor microenvironment," Poster #5831, 2018.

Schaal et al., "Injectable polypeptide micelles that form radiation crosslinked hydrogels in situ for intratumoral radiotherapy," Journal of Controlled Release, Apr. 2016, 228, 58-66.

Schellenberg et al., "Gemcitabine chemotherapy and single-fraction stereotactic body radiotherapy for locally advanced pancreatic cancer," Int J Radiation Oncol Biol Phys,Nov. 2008, 72(3): 678-686.

Schellenberg et al., "Single-fraction stereotactic body radiation therapy and sequential gemcitabine for the treatment of locally advanced pancreatic cancer," Int J Radiation Oncology Biol Phys, Sep. 2011, 81(1): 181-188.

Schellenberger et al., "A recombinant polypeptide extends the in vivo half-life of peptides and proteins in a tunable manner," Nat. Biotechnol., Dec. 2009, 27(12):1186-1188.

Schlaff et al., "Bringing the heavy: carbon ion therapy in the radiobiological clinical context," Radiation Oncology, Mar. 2014, 9, Article 88, 1-18.

Schneider et al., "NIH Image to ImageJ: 25 years of image analysis," Nature Methods, Jul. 2012, 9(7): 671-675.

Schnell et al., "Expression of integrin αvβ3 in gliomas correlates with tumor grade and is not restricted to tumor vasculature," Brain Pathol, International Society of Neuropathology, Aug. 2008, 18(3):378-86.

Schwendeman et al., "Injectable controlled release depots for large molecules," J Control Release, Sep. 2014, 190, 240-253.

Senin et al., "N-Myristoylation of recoverin enhances its efficiency as an inhibitor of rhodopsin kinase," Febs. Lett., 1995, 376, 87-90.

Senior et al., "Val-Gly-Val-Ala-Pro-Gly, a Repeating Peptide in Elastin, Is Chemotactic for Fibroblasts and Monocytes," The Journal of Cell Biology, 1984, 99: 870-874.

Seow et al., "Longitudinal evaluation and decline of antibody responses in SARS-CoV-2 infection," medRxiv, 2020, 24 pages.

Serrano et al., "An infrared spectroscopic study of the conformational transition of elastin-like polypeptides," Biophys. J., Oct. 2007, 93(7):2429-2435.

Shadwick, "Mechanical design in arteries," J Exp Biol, 1999, 202, 3305-3313.

Shang et al., "pH-Dependent Protein Conformational Changes in Albumin:Gold Nanoparticle Bioconjugates: A Spectroscopic Study," Langmuir, Feb. 2007, 23 (5), 2714-2721.

Shao et al., "Super-resolution 3D microscopy of live whole cells using structured illumination," Nat Methods, Oct. 2011, 8(12): 1044-1046.

Sharma et al., "Dendrimer nanoarchitectures for cancer diagnosis and anticancer drug delivery," Drug Discov Today, Feb. 2017, 22(2):314-326.

Sharma et al., "PLGA-based nanoparticles: A new paradigm in biomedical applications," TrAC Trends in Analytical Chemistry, Jun. 2016, 80:30-40.

Sharma et al., "Polymer particle shape independently influences binding and internalization by macrophages," Journal of Controlled Release, Elsevier, Nov. 2010, 147(3):408-412.

Shen et al., "Conjugation site modulates the in vivo stability and thearpeutic activity of antibody-drug conjugates," Nat Biotechnol, Jan. 2012, 30(2):184-189.

Sheparovych et al., "Stimuli-Responsive Properties of Peptide-Based Copolymers Studied via Directional Growth of Self-Assembled Patterns on Solid Substrate," Biomacromolecules, Jul. 2009, 10:1955-1961.

Sherman et al., "Next-Generation PEGylation Enables Reduced Immunoreactivity of PEG-Protein Conjugates," Drug and Development & Delivery, Jun. 2012, vol. 12, No. 5, 36-42.

Sherman et al., "Role of the Methoxy Group in Immune Responses to mPEG-Protein Conjugates," Bioconjugate Chemistry, Mar. 2012, 23(3): 485-499.

Shi et al., "Cell adhesion on a POEGMA-modified topographical surface," Langmuir: the ACS journal of surfaces and colloids, Dec. 2012, 28 (49), 17011-8.

Shi et al., "Triggered sorting and co-assembly of genetically engineered protein microdomains in the cytoplasm," Adv Mater, Wiley, Jan. 2014, 26(3):449-454.

Shimoboji et al., "Temperature-Induced Switching of Enzyme Activity with Smart Polymer-Enzyme Conjugates," Bioconjugate Chem. 2003, 14, 517-525.

Shin et al., "Liquid phase condensation in cell physiology and disease," Science, Sep. 2017, 357(6357):eaaf4382.

Shusharina et al., "Micelles of Diblock Copolymers with Charged and Neutral Blocks: Scaling and Mean-Field Lattice Approaches," Macromolecules, 2000, 33(10): 3892-3901.

Sickmeier et al., "DisProt: the Database of Disordered Proteins," Nucleic Acids Res, Oxford Academy, Jan. 2007, 35:D786-793.

Siegel et al., "Absorbed fractions for electrons and beta particles in spheres of various sizes," J Nucl Med, 1994, 35, 152-156.

Siegwart et al., "ATRP In The Design Of Functional Materials For Biomedical Applications," Prog Polymer Science, Jan. 2012, vol. 37, No. 1, pp. 18-37.

Silberstein et al., "The SNM Practice Guideline for Therapy of Thyroid Disease with $^{131}$I, 3.0," J Nucl Med, Jul. 2012, 53, 1-19.

Silva et al., "Selective differentiation of neural progenitor cells by high-epitope density nanofibers," Science, 2004, 303, 1352-5.

Simakova et al., "Aqueous ARGET ATRP," Macromolecules, Aug. 2012, 45(16):6371-6379.

Simnick et al., "In vivo tumor targeting by a NGR-decorated micelle of a recombinant diblock copolypeptide," J Control Release, Oct. 2011, 155(2): 144-151.

Simnick et al., "Morphing low-affinity ligands into high-avidity nanoparticles by thermally triggered self-assembly of a genetically encoded polymer," ACS Nano, Apr. 2010, 4(4):2217-2227.

Simon et al., "Engineered Ribonucleoprotein Granules Inhibit Translation in Protocells," Molecular cell, Jul. 2019, 75(1):66-75.

(56) References Cited

OTHER PUBLICATIONS

Simon et al., "Programming molecular self-assembly of intrinsically disordered proteins containing sequences of low complexity," Nat Chem, Jun. 2017, 9(6):509-515.
Simonacci et al., "Procedure, applications, and outcomes of autologous fat grafting," Ann Med Surg (Lond), 2017, 20: 49-60.
Singhal et al., "Fibroblast Growth Factor 21 (FGF21) Protects against High Fat Diet Induced Inflammation and Islet Hyperplasia in Pancreas," PLoS One, Feb. 2016, 11(2):e0148252.
Sisson et al., "Radiation safety in the treatment of patients with thyroid diseases by radioiodine 131I: practice recommendations of the American Thyroid Association," Thyroid, Apr. 2011, 21(4):335-346.
Skerra, "Alternative non-antibody scaffolds for molecular recognition," Curr Opin Biotechnol, Elsevier, Aug. 2007, 18(4):295-304.
Smith et al., "The Role of Beta Cell Glucagon-like Peptide-1 Signaling in Glucose Regulation and Response to Diabetes Drugs," Cell Metab, Jun. 2014, 19(6):1050-1057.
Smits et al., "Elastin-Like Polypeptide Based Nanoparticled: Design Rationale Toward Nanomedicine," Macromolecular Bioscience, Macromolecular Journals, Jan. 2015, 15(1):36-51.
Sonawane et al., "Hydrazo linkages in pH responsive drug delivery systems," European Journal Pharmaceutical Sciences, Mar. 2017, 99, 45-65.
Song et al., "Budding-like division of all-aqueous emulsion droplets modulated by networks of protein nanofibrils," Nat Commun, 2018, 9: 2110.
Sorkin et al., "Signal transduction and endocytosis: close encounters of many kinds," Nat Rev Mol Cell Biol, 2002, 3(8):600-614.
Sousa et al., "Production of a polar fish antimicrobial peptide in *Escherichia coli* using an ELP-intein tag," J Biotechnol, Sep. 2016, 234:83-89.
Srinivas et al., "Aptamer-functionalized microgel particles for protein detection," Anal Chem, 2011, 83: 9138-9145.
Sriraman et al., "Barriers to drug delivery in solid tumors, " Tissue Barriers, Jul. 2014, 2(3): 2-10.
Stanislaus et al., "A Novel Fc-FGF21 With Improved Resistance to Proteolysis, Increased Affinity Toward β-Klotho, and Enhanced Efficacy in Mice and Cynomolgus Monkeys," Endocrinology, May 2017, 158(5):1314-1327.
Stefl et al., "RNA sequence-and shape-dependent recognition by proteins in the ribonucleoprotein particle" EMBO reports (2005) 6(1):33-38.
Steichen et al., "A Review of Current Nanoparticle and Targeting Moieties for the Delivery of Cancer Therapeutics," Eur J Pharm Sci, Elsevier, Feb. 2013, 48(3):416-27.
Stock et al., "Penile erectile function after permanent raioactive seed implantation for treatment of prostate cancer," The Journal of urology, 2001, 165, 436-439.
Stork et al., "A novel tri-functional antibody fusion protein with improved pharmacokinetic properties generated by fusing a bispecific single-chain diabody with an albumin-binding domain from streptococcal protein G," Protein Engineering Design and Selection, Nov. 2007, 20(11): p. 569-576.
Strohmaier et al., "Comparison of $^{60}$Co and $^{192}$Ir sources in HDR brachytherapy," J Contemp Brachyther, Dec. 2011, 3(4): 199-208.
Strong et al., "The Current State of Fat Grafting: A Review of Harvesting, Processing, and Injection Techniques," Plast Reconstr Surg, 2015, 136: 897-912.
Strulson et al., "RNA catalysis through compartmentalization," Nat Chem, Nature Publishing Group, Nov. 2012, 4(11):941-946.
Stutz et al., "Seed loss through the urinary tract after prostate brachytherapy: examining the role of cystoscopy and urine straining post implant," Medical physics, 2003, 30, 2695-2698.
Sugyo et al., "Evaluation of efficacy of radioimmunotherapy with 90Y-labeled fully human anti-transferring receptor monoclonal antibody in pancreatic cancer mouse models," PLoS One, Apr. 2015, 10, 1-17.
Suk et al., "PEGylation as a Strategy for Improving Nanoparticle-Based Drug and Gene Delivery," Adv Drug Deliv Rev, Apr. 2016, 99(Pt A):28-51.
Sumerlin, "Proteins as Initiators of Controlled Radical Polymerization: Grafting-from via ATRP and RAFT," ACS Macro Lett. Jan. 2012, 1(1): 141-145.
Sun et al., "Autofluorescence Imaging of Living Pancreatic Islets Reveals Fibroblast Growth Factor-21 (FGF21)-Induced Metabolism," Biophys J, Dec. 2012, 103(11):2379-2388.
Sun et al., "Contributions of the extracellular and cytoplasmic domains of platelet-endothelial cell adhesion molecule-1 (PECAM-1/CD31) in regulating cell-cell localization," J. Cell Sci., 2000, 113, 1459-1469.
Sun et al., "Efficacy and safety of the hypoxia-activated prodrug TH-302 in combination with gemcitabine and nab-paclitaxel in human tumor xenograft models of pancreatic cancer," Cancer Biology & Therapy, Feb. 2015, 16(3): 438-449.
Sun et al., "EUS-guided interstitial brachytherapy of the pancreas: a feasibility study," Gastrointestinal Endoscopy, 2005, 62, 775-779.
Sun et al., "On the Thermally Reversible Dynamic Hydration Behavior of Oligo(ethylene glycol) Methacrylate-Based Polymers in Water," Macromolecules, Jan. 2013, 46(1): 236-246.
Sunamura et al., "Gene Therapy for Pancreatic Cancer Targeting the Genomic Alterations of Tumor Suppressor Genes using Replication-selective Oncolytic Adenovirus," Human Cell, 2002, 15, 138-150.
Sundy et al., "Efficacy and tolerability of pegloticase for the treatment of chronic gout in patients refractory to conventional treatment: two randomized controlled trials," Jama, 2011, 306(7): 711-720.
Sundy et al., "Pharmacokinetics and pharmacodynamics of intravenous PEGylated recombinant mammalian urate oxidase in patients with refractory gout," Arthritis Rheum, 2007, 56(3): 1021-1028.
Surwit et al., Diet-induced type II diabetes in C57BL/6J mice, Diabetes 37, 1988, 1163-1167.
Sussman et al., "Porous implants modulate healing and induce shifts in local macrophage polarization in the foreign body reaction," Ann Biomed Eng, Jul. 2014, 42(7): 1508-1516.
Swee et al., "Sortase-mediated modification of αDEC205 affords optimization of antigen presentation and immunization against a set of viral epitopes," Proc Natl Acad Sci USA, Jan. 2013, 110(4):1428-1433.
Swers et al., Multivalent Scaffold Proteins as Superagonists of TRAIL Receptor 2-Induced Apoptosis, Mol Cancer Ther, Jul. 2013, 12(7): 1235-1244.
Swider et al., "Customizing Poly(lactic-Co-Glycolic Acid) Particles for Biomedical Applications," Acta Biomater, Jun. 2018, 73:38-51.
Takalkar et al., "Radium-223 dichloride bone-targeted alpha particle therapy for hormone-refractory breast cancer metastatic to bone," Exp Hematol Oncol, Sep. 2014, 8, Article No. 23.
Talelli et al., "Core-Crosslinked Polymeric Micelles: Principles, Preparation, Biomedical Applications and Clinical Translation," Nano Today, Feb. 2015, 10(1):93-117.
Tallarida, "Quantitative methods for assessing drug synergism," Genes & Cancer, Nov. 2011, 2(11): 1003-1008.
Talukdar et al., "A Long-Acting FGF21 Molecule, PF-05231023, Decreases Body Weight and Improves Lipid Profile in Non-human Primates and Type 2 Diabetic Subjects," Cell Metab, Mar. 2016, 23(3):427-440.
Tamburro et al., "Dissection of human tropoelastin: exon-by-exon chemical synthesis and related conformational studies," Biochemistry, 2003, 42, 13347-13362.
Tamburro et al., "Fractal aspects of elastin supramolecular organization," J Biomol Struct Dyn, 1995, 12: 1161-1172.
Tamburro et al., "Localizing alpha-helices in human tropoelastin: assembly of the elastin "puzzle"," Biochemistry, Aug. 2006, 45(31): 9518-9530.
Tan et al., "Characterization of a new primary human pancreatic tumor line," Cancer investigation, 1986, 4, 15-23.
Tang et al., "Combinatorial codon scrambling enables scalable gene synthesis and amplification of repetitive proteins," Nature Mater., Apr. 2016, 15(4): 419-424.

(56) References Cited

OTHER PUBLICATIONS

Tang et al., "Enzymatic Polymerization of High Molecular Weight DNA Amphiphiles That Self-Assemble into Star-Like Micelles," Advanced Materials, Feb. 2014, 26(19): 3050-3054.

Tang et al., "High-Molecular-Weight Polynucleotides by Transferase-Catalyzed Living Chain-Growth Polycondensation," Angew. Chem., Jun. 2017, 56(24): 6778-6782.

Tang et al., "Identification of PECAM-1 in solid tumor cells and its potential involvement in tumor cell adhesion to endothelium," J. Biol. Chem., 1993, 268, 22883-22894.

Tang et al., "Laboratory Diagnosis of COVID-19: Current Issues and Challenges," J Clin Microbiol, 2020, 58: e00512-20, 9 pages.

Tantakitti et al., "Energy landscapes and functions of supramolecular systems," Nat. Mater., Apr. 2016, 15(4): 469-476.

Tedja et al., "Effect of TiO2 nanoparticle surface functionalization on protein adsorption, cellular uptake and cytotoxicity: the attachment of PEG comb polymers using catalytic chain transfer and thiol-ene chemistry," Polymer Chemistry, Oct. 2012, 3 (10), 2743-2751.

Teicher, "In vivo/ex vivo and in situ assays used in cancer research: a brief review," Toxicol. Pathol., Jan. 2009, 37 (1), 114-122.

Thakor et al., "Clinically Approved Nanoparticle Imaging Agents," J Nucl Med, Oct. 2016, 57(12):1833-1837.

Theillet et al., "The alphabet of intrinsic disorder: I. Act like a Pro: On the abundance and roles of proline residues in intrinsically disordered proteins," Intrinsically Disord Proteins, Taylor & Francis, Apr. 2013, 1(1):e24360.

Therasse et al., "New guidelines to evaluate the response to treatment in solid tumors," J Natl Cancer Inst, 2000, 92, 205-216.

Thorens et al., "Cloning and functional expression of the human islet GLP-1 receptor: demonstration that Exendin-4 Is an agonist and Exendin-(9-39) an antagonist of the receptor," Diabetes 42, 1993, 1678-1682.

Tomiyama et al., "Relevant use of Klotho in FGF19 subfamily signaling system in vivo," Proc Natl Acad Sci USA, Jan. 2010, 107(4):1666-71.

Tompa et al., "Fuzzy complexes: polymorphism and structural disorder in protein-protein interactions," Trends Biochem Sci, Jan. 2008, 33(1): 2-8.

Tong et al., "Protein Modification with Amphiphilic Block Copoly(2-oxazoline)s as a New Platform for Enhanced Cellular Delivery," Mol. Pharm., Aug. 2010, vol. 7, No. 4, pp. 984-992.

Ton-That et al., "Assembly of pili on the surface of Corynebacterium diptheriae," 2003, 50(4):1429-1438.

Ton-That et al., "Purification and characterization of sortase, the transpeptide that cleaves surface proteins of Staphylococcus aureus and the LPXTG motif," Proc Natl Acad Sci USA, 1999, 96(22):12424-12429.

Torchilin, "Recent advances with liposomes as pharmaceutical carriers," Nature Rev. Drug Discov. 2005, 4(2):145-160.

Toshima et al., "Three-dimensional architecture of elastin and collagen fiber networks in the human and rat lung," Arch Histol Cytol, 2004, 67: 31-40.

Towler et al., "Purification and Characterization of Yeast Myristoyl-Coa-Protein N-Myristoyltransferase," P Natl Acad Sci USA, 1987, 84(9):2708-12.

Trabbic-Carlson et al., "Effect of protein fusion on the transition temperature of an environmentally responsive elastin-like polypeptide: a role for surface hydrophobicity?," Protein Engineering Design and Selection, 2004, 17(1): 57-66.

Trabbic-Carlson et al., "Expression and purification of recombinant proteins from Escherichia coli: Comparison of an elastin-like polypeptide fusion with an oligohistidine fusion" Protein Science, 2004, 13: 3274-3284.

Trakul et al., "Stereotactic body radiotherapy in the treatment of pancreatic cancer," Semin Radiat Oncol, Apr. 2014, 24(2): 140-147.

Trieu et al., "P0157 Preclinical evaluation of NBN-paclitaxel in pancreatic cancer xenograft models," Eur J Cancer, May 2014, 50(4): e53.

Triola et al., "Chemical biology of lipidated proteins," ACS Chemical Biology, Jan. 2012, 7(1): 87-99.

Troyanskaya et al., "Nonparametric methods for identifying differentially expressed genes in microarray data," Bioinformatics, 2002, 18(11):1454-61.

Truong et al., "Polymeric filomicelles and nanoworms: two decades of synthesis and application," Polymer Chemistry, Jun. 2016, 7(26):4295-4312.

Truong et al., "The Importance of Nanoparticle Shape in Cancer Drug Delivery," Expert Opin Drug Deliv, Jan. 2015, 12(1):129-42.

Truong, et al., "The effect of hydration on molecular chain mobility and the viscoelastic behavior of resilin-mimetic protein-based hydrogels," Biomaterials, Elsevier, Nov. 2011, 32(33):8462-73.

Tsarevsky et al., "Deactivation efficiency and degree of control over polymerization in ATRP in protic solvents," Macromolecules 37, 2004, 9768-9778.

Tschöp et al., "Unimolecular Polypharmacy for Treatment of Diabetes and Obesity," Cell Metab, Jul. 2016, 24(1):51-62.

Tsuda et al., "Monodisperse cell-encapsulating peptide microgel beads for 3D cell culture," Langmuir, 2010, 26: 2645-2649.

Tsume et al., "The development of orally administrable gemcitabine prodrugs with D-enantiomer amino acids: Enhanced membrane permeability and enzymatic stability," Eur. J. Pharm. Biopharm., Apr. 2014, 86(3):514-523.

Tu et al., "Stages in tropoelastin coalescence during synthetic elastin hydrogel formation," Micron, Apr. 2010, 41(3): 268-272.

Turner et al., "Challenges and Opportunities for the Subcutaneous Delivery of Therapeutic Proteins," Journal of Pharmaceutical Sciences, 2018, 107(5): 1247-1260.

Turunen et al., "Paclitaxel Succinate Analogs: Anionic Introduction as a Strategy to Impart Blood Brain Barrier Permeability," Bioorg Med Chem Lett, Nov. 2008, 18(22):5971-5974.

Tward et al., "Survival of men with clinically localized prostate cancer treated with prostatectomy, brachytherapy, or No. definitive treatment: impact of age at diagnosis," Cancer, Oct. 2006, 107(10): 2392-2400.

U.S. FDA—Classify your medical devices. Updated as of: Feb. 7, 2020. Available at: <https://www.fda.gov/medical-devices/overview-device-regulation/classify-your-medical-device>.

U.S. FDA—In Vitro Diagnostics. Updated as of: Oct. 25, 2019. Available at: <https://www.fda.gov/medical-devices/products-and-medical-procedures/vitro-diagnostics>.

Uchida et al., "Potential of adenovirus-mediated REIC/Dkk-3 gene therapy for use in the treatment of pancreatic cancer," Journal of Gastroenterology and Hepatology, Apr. 2014, 29(5):973-983.

UniProtKB-P15214 (GST_PROMI) acessed online at <https://www.uniprot.org/uniprot/P152146/> on Jun. 8, 2021, 7 pages.

Urry et al., "Calculation of distorted circular dichroism curves for poly-L-glutamic acid suspensions," Arch Biochem Biophys, 1970, 137, 214-221.

Urry et al., "Coacervation of solubilized elastin effects a notable conformational change," Nature, 1969, 222, 795-796.

Urry et al., "Differential scatter of left and right circularly polarized light by optically active particulate systems," Proc Natl Acad Sci U S A, 1970, 65, 845-852.

Urry et al., "Distortions in circular dichroism patterns of particulate (or membranous) systems," Arch Biochem Biophys, 1968, 128, 802-807.

Urry et al., "Elastic protein-based polymers in soft tissue augmentation and generation," J. Biomater. Sci. Polym. Ed., 1998, 9, 1015-1048.

Urry et al., "Hydrophobicity Scale for Proteins Based on InverseTemperature Transitions," Biopolymers, 1992, 32:1243-1250.

Urry et al., "Physical chemistry of biological free energy transduction as demonstrated by elastic protein-based polymers," J. of Phys. Chem. B., 1997, 101, 11007-11028.

Urry et al., "Temperature dependence of length of elastin and its polypentapeptide," Biochem Biophys Res Commun, 1986, 141, 749-755.

Urry et al., "Temperature of polypeptide inverse temperature transition depends on mean residue hydrophobicity," J. Am. Chem. Soc., 1991, 113(11):4346-4348.

(56) References Cited

OTHER PUBLICATIONS

Urry, "Free energy transduction in polypeptides and proteins based on inverse temperature transitions," Prog Biophys Mol Biol, Jan. 1992, 57(1):23-57.
Urry, "Protein elasticity based on conformations of sequential polypeptides: The biological elastic fiber," J Protein Chemistry, 1984, 3, 403-436.
Utada et al., "Monodisperse double emulsions generated from a microcapillary device," Science, 2005, 308: 537-541.
Uversky et al., "Intrinsically disordered proteins as crucial constituents of cellular aqueous two phase systems and coacervates," FEBS Lett, Jan. 2015, 589(1):15-22.
Uversky et al., "Understanding protein non-folding," Biochim Biophys Acta, Elsevier, Jun. 2010, 1804(6):1231-1264.
Uversky, "Protein intrinsic disorder-based liquid-liquid phase transitions in biological systems: Complex coacervates and membrane-less organelles," Adv Colloid Interface Sci, 2017, 239: 97-114.
Valkenburg et al., "Targeting the tumour stroma to improve cancer therapy," Nature Reviews Clinical Oncology, Jun. 2018, 15, 366-381.
Van der Lee et al., "Classification of intrinsically disordered regions and proteins," Chem Rev, Jul. 2014, 114(13): 6589-6631.
Van Roey et al., "Short linear motifs: ubiquitous and functionally diverse protein interaction modules directing cell regulation, " Chem Rev, Jully 2014, 114(13): 6733-6778.
Van Roy, "Beyond E-cadherin: roles of other cadherin superfamily members in cancer," Nat Rev Cancer, Feb. 2014, 14(2): 121-134.
Vaninov, "In the eye of the COVID-19 cytokine storm," Nat Rev Immunol, 2020, 20: 277, 1 page.
Vasey et al., "Phase I clinical and Pharmacokinetic study of PK1 (N-(2-Hydroxypropyl)methacrylamide Copolymer Doxorubicin): First member of a New Class of Chemotherapeutic Agents-Drugs-Polymer Conjugates" Clinical Cancer Research, 1999, 5:83-94.
Vashist et al., "Emerging Technologies for Next-Generation Point-of-Care Testing," Trends Biotechnol, 2015, 33(11): 692-705.
Vazquez-Lombardi et al., "Challenges and Opportunities for Non-Antibody Scaffold Drugs," Drug Discov Today, Oct. 2015, 20(10):1271-83.
Vega et al., "Targeting Doxorubicin to Epidermal Growth Factor Receptors by Site-Specific Conjugation of C225 to Poly(L-Glutamic Acid) through a Polyethylene Glycol Spacer," Pharmaceutical Research, 2003, 20(5):826-832.
Venkataraman et al., "The Effects of Polymeric Nanostructure Shape on Drug Delivery," Adv Drug Deliv Rev, Elsevier, Nov. 2011, 63(14-15):1228-46.
Verhoef et al., "Potential induction of anti-PEG antibodies and complement activation toward PEGylated therapeutics," Drug Discov Today, 2014, 19(12): 1945-1952.
Verma et al., "Effect of surface properties on nanoparticle-cell interactions," Small, Wiley, Jan. 2010, 6(1):12-21.
Veronese et al., "PEGylation, successful approach to drug delivery," Drug Discovery Today, 2005, 10(21):1451-1458.
Veronese, "Peptide and protein PEGylation: a review of problems and solutions," Biomaterials 22, 2001, 405-417.
Vicini et al., "An interinstitutional and interspecialty comparison of treatment outcome data for patients with prostate carcinoma based on predefined prognostic categories and minimum follow-up," Cancer, 2002, 95, 2126-2135.
Viegas et al., "Polyoxazoline: Chemistry, properties and applications," Bioconjugate Chem., May 2011, 22(5): 976-986.
Vlieghe et al., "Synthetic therapeutic peptides: science and market," Drug Discovery Today, Jan. 2010, 15(1-2): 40-56.
Voelker et al., "Alteration of the specificity and regulation of fatty acid synthesis of *Escherichia coli* by expression of a plant medium-chain acyl-acyl carrier protein thioesterase," J Bacteriol., 1994, 176(23):7320-7.
Volkova et al., "Anthracycline Cardiotoxicity: Prevalence, Pathogenesis and Treatment," Curr. Cardiol. Rev., Nov. 2011, vol. 7, No. 4, pp. 214-220.

Volodkin et al., "One-Step Formulation of Protein Microparticles with Tailored Properties: Hard Templating at Soft Conditions," Advanced Functional Materials, 2012, 22: 1914-1922.
Von Roemeling et al., "Breaking Down the Barriers to Precision Cancer Nanomedicine," Trends Biotechnol, Feb. 2017, 35(2):159-171.
Vonarbourg et al., "Evaluation of pegylated lipid nanocapsules versus complement system activation and macrophage uptake," J Biomed Mater Res A, Wiley, Sep. 2006, 78(3):620-8.
Vrhovski et al., "Biochemistry of tropoelastin," Eur J Biochem, 1998, 258, 1-18.
Vrhovski et al., "Coacervation Characteristics of Recombinant Human Tropoelastin," European Journal of Biochemistry, 1997, 250(1):92-98.
Vrignaud et al., "Strategies for the nanoencapsulation of hydrophilic molecules in polymer-based nanoparticles," Biomaterials, Nov. 2011, 32(33):8593-8604.
Vugmeyster et al., "Pharmacokinetics and toxicology of therapeutic proteins: Advances and challenges," World J Biol Chem, 2012, 3(4): 73-92.
Walczak, "Death Receptor-Ligand Systems in Cancer, Cell Death, and Inflammation," Cold Spring Harb. Perspect. Biol., May 2013, 5(5): a008698.
Wali et al., "Measuring Death of Pancreatic Beta Cells in Response to Stress and Cytotoxic T Cells," Methods in Molecular Biology, Mar. 2015, 1292:165-176.
Walsh et al., "Post-translational modifications in the context of therapeutic proteins," Nat. Biotechnol., Oct. 2006, 24(10): 1241-1252.
Walsh et al., "Posttranslationale Proteinmodifikation: die Chemie der Proteomdiversifizierung," Angew Chem, 2005, 117, 7508-7539.
Walsh et al., "Protein posttranslational modifications: The chemistry of proteome diversifications," Angew. Chem. Int. Ed., 2005, 44, 7342-7372.
Wang et al., "A Molecular Grammar Governing the Driving Forces for Phase Separation of Prion-like RNA Binding Proteins," Cell, Jul. 2018, 174(3):688-699.e616.
Wang et al., "Enhanced Tumor Delivery of Gemcitabine via PEG-DSPE/TPGS Mixed Micelles," Mol. Pharm., Apr. 2014, 11(4): 1140-1150.
Wang et al., "Extending Half Life of H-Ferritin Nanoparticle by Fusing Albumin Binding Domain for Doxorubicin Encapsulation," Biomacromolecules, Mar. 2018, 19(3):773-781.
Wang et al., "Functional polymeric microparticles engineered from controllable microfluidic emulsions," Acc Chem Res, 2014, 47: 373-384.
Wang et al., "More effective nanomedicines through particle design," Small, Wiley, Jul. 2011, 7(14):1919-31.
Wang et al., "Nanoparticle delivery of cancer drugs," Annu Rev Med, Annual Reviews, Feb. 2012, 63:185-98.
Wang et al., "Pigs Can Be Used as a Large Animal Model for Autologous Fat Grafting," Ophthalmic Plast Reconstr Surg, 2016, 32: 73-74.
Wang et al., "Quantitative Mapping of the Spatial Distribution of Nanoparticles in Endo-Lysosomes by Local pH," Nano Lett., Feb. 2017, 17(2): 1226-1232.
Wang et al., "Size and dynamics of caveolae studied using nanoparticles in living endothelial cells," ACS nano, Dec. 2009, 3(12): p. 4110-4116.
Wang et al., "Stimuli-responsive Dendrimers in Drug Delivery," Biomater Sci, Mar. 2016, 4(3):375-90.
Wang et al., "The Weak Link: Optimization of the Ligand-Nanoparticle Interface To Enhance Cancer Cell Targeting by Polymer Micelles," Nano Lett Oct. 2017, 17(10):5995-6005.
Waterboer et al., "Suppression of non-specific binding in serological Luminex assays," J Immunol Methods, 2006, 309: 200-204.
Waterman et al., "Edema associated with I-125 or Pd-103 prostate brachytherapy and its impact on post-implant dosimetry: an analysis based on serial CT acquisition," International journal of radiation oncology, biology, physics, 1998, 41, 1069-1077.
Wechsel et al., "Renal Cell Carcinoma: Immunohistological Investigation of Expression of the Integrin αvβ3," Anticancer research, 1999, 19(2C):1529-1532.

(56) References Cited

OTHER PUBLICATIONS

Wei et al., "Anticancer drug nanomicelles formed by self-assembling amphiphilic dendrimer to combat cancer drug resistance," Proceedings of the National Academy of Sciences of the United States of America, Mar. 2015, 112(10): 2978-2983.
Wei et al., "Fibroblast growth factor 21 promotes bone loss by potentiating the effects of peroxisome proliferator-activated receptor γ," Proc Natl Acad Sci USA, Feb. 2012, 109(8):3143-3148.
Weinhandl et al., "Relative safety of peginesatide and epoetin alfa," Pharmacoepidemiology and Drug Safety, 2014, 23(10): 1003-1011.
Weis et al., "αV Integrins in Angiogenesis and Cancer," Cold Spring Harb Perspect Med, Cold Spring Harbor Laboratory Press, Sep. 2011, 1(1):a006478.
Weitzhandler et al., "Micellar Self-Assembly of Recombinant Resilin-/Elastin-Like Block Copolypeptides," Biomacromolecules, Aug. 2017, 18(8):2419-2426.
Wendt et al., "DNA-mediated Folding and Assembly of MyoD-E47 Heterodimers," Journal of Biol. Chem., 1998, 273(10):5735-5743.
Wente et al., "Fibroblast Growth Factor-21 Improves Pancreatic β-Cell Function and Survival by Activation of Extracellular Signal-Regulated Kinase ½ and Akt Signaling Pathways," Diabetes, Sep. 2006, 55(9):2470-2478.
Werle et al., "Strategies to improve plasma half life time of peptide and protein drugs," Amino Acids 30, Jun. 2006, 30(4):351-367.
Whitman et al., "Evaluation of SARS-CoV-2 serology assays reveals a range of test performance," Nat Biotechnol, 2020, 38: 1174-1183.
Wienkers et al., "Predicting in vivo drug interactions from in vitro drug discovery data," Nat. Rev. Drug. Discov. 2005, 4(10):825-833.
Wiersinga et al., "Pathophysiology, Transmission, Diagnosis, and Treatment of Coronavirus Disease 2019 (COVID-19): A Review," JAMA, 2020, 324(8): 782-793.
Wilkins et al., "Hydrodynamic Radii of Native and Denatured Proteins Measured by Pulse Field Gradient NMR Techniques," Biochemistry, 1999, 38(50):16424-16431.
Williams et al., "Targeted radionuclide therapy," Medical Physics, Jul. 2008, 35(7): 3062-3068.
Williamson et al., "Efficient N-terminal labeling of proteins by use of sortase," Angew Chem Int ed Engl, Sep. 2012, 51(37):9377-9380.
Wimley et al., "Experimentally determined hydrophobicity scale for proteins at membrane interfaces," Nature Structural & Molecular Biology, 1996, 3(10):842-848.
Winter et al., "The important role of serology for COVID-19 control," Lancet Infect Dis, 2020, 20: 758-759.
Winzell et al., "The high-fat diet-fed mouse: a model for studying mechanisms and treatment of impaired glucose tolerance and type 2 diabetes," Diabetes 53, 2004, S215-S219.
Wold, "In vivo chemical modification of proteins," Annu. Rev. Med., 1981, 50, 783-814.
Wölfel et al., "Virological assessment of hospitalized patients with COVID-2019," Nature, 2020, 581: 465-469.
Wood et al., "Experiences Using Chloramine-T and 1,3,4,6-Tetrachloro-3-Alpha,6-Alpha-Diphenylglycoluril (Iodogen) for Radioiodination of Materials for Radioimmunoassay," J Clin Chem Clin Bio, 1981, 19, 1051-1056.
Wright et al., "Intrinsically disordered proteins in cellular signalling and regulation," Nat Rev Mol Cell Biol, Jan. 2015, 16(1):18-29.
Wright et al., "Self-assembly of block copolymers derived from elastin-mimetic polypeptide sequences," Advanced Drug Delivery Reviews, 2002, 54, 1057-1073.
Wright et al., "Thermoplastic elastomer hydrogels via self-assembly of an elastin-mimetic triblock polypeptide," Advanced Functional Materials, 2002, 12, 149-154.
Wu et al., "An injectable adipose matrix for soft-tissue reconstruction," Plast Reconstr Surg, 2012, 129: 1247-1257.
Wu et al., "Site-specific chemical modification of recombinant proteins produced in mammalian cells by using the genetically encoded aldehyde tag," Proc Natl Acad Sci USA, Mar. 2009, 106(9):3000-3005.
Wu et al., "Sortase A-Catalyzed Transpeptidation of Glycosylphosphatidylinositol Derivatives for Chemoenzymatic Synthesis of GPI-Anchored Proteins," J. Am. Chem. Soc., Feb. 2010, 132(5): 1567-1571.
Wust et al., "Hyperthermia in combined treatment of cancer," The Lancet Oncology, 2002, 3, 487-497.
Xavier et al., "HPLC Method for the Dosage of Paclitaxel in Copaiba Oil: Development, Validation, Application to the Determination of the Solubility and Partition Coefficients," Chromatographia, Apr. 2016, 79(7-8): 405-412.
Xia et al., "Tunable self-assembly of genetically engineered silk-elastin-like protein polymers," Biomacromolecules, Nov. 2011, 12(11): 3844-3850.
Xie et al., "The Effect of Shape on Cellular Uptake of Gold Nanoparticles in the Forms of Stars, Rods, and Triangles," Sci Rep, Jun. 2017, 7(1):3827.
Xiong et al., "Engineering of amphiphilic block copolymers for polymeric micellar drug and gene delivery," J Control Release, Elsevier, Oct. 2011, 155(2):248-61.
Xu et al., "A quality by design (QbD) case study on liposomes containing hydrophilic API: II. Screening of critical variables, and establishment of design space at laboratory scale, " Int. J. Pharm., Feb. 2012, 423(2):543-553.
Xu et al., "Downregulation of GLP-1 and GIP Receptor Expression by Hyperglycemia," Diabetes, Jun. 2007, 56(6):1551-58.
Xu et al., "Exendin-4 stimulates both beta-cell replication and neogenesis, resulting in increased beta-cell mass and improved glucose tolerance in diabetic rats," Diabetes 48, 1999, 2270-2276.
Xu et al., "Fibroblast Growth Factor 21 Reverses Hepatic Steatosis, Increases Energy Expenditure, and Improves Insulin Sensitivity in Diet-Induced Obese Mice," Diabetes, Jan. 2009, 58(1):250-259.
Xu et al., "Genetically engineered block copolymers: influence of the length and structure of the coiled-coil blocks on hydrogel self-assembly," Pharm Res, Mar. 2008, 25, 674-682.
Xu et al., "Inorganic nanoparticles as carriers for efficient cellular delivery," Chemical Engineering Science, Elsevier, Feb. 2006, 61(3):1027-1040.
Xu et al., "Role of pancreatic stellate cells in pancreatic cancer metastasis," Am J of Pathology, Nov. 2010, 177(5): 2585-2596.
Xu et al., "Self-assembly behavior of peptide amphiphiles (PAs) with different length of hydrophobic alkyl tails," Colloids Surfaces B Biointerfaces, Nov. 2010, 81(1): 329-335.
Yamamoto et al., "ATRP Synthesis of Thermally Responsive Molecular Brushes from Oligo(ethylene oxide) Methacrylates," Macromolecules, Dec. 2007, 40(26): 9348-9353.
Yang et al., "Analysis of Pre-existing IgG and IgM Antibodies against Polyethylene Glycol (PEG) in the General Population," Analytical Chemistry, 2016, 88(23): 11804-11812.
Yang et al., "Anti-PEG immunity: emergence, characteristics, and unaddressed questions," Wiley Interdiscip Rev Nanomed Nanobiotechnol, 2015, 7(5): 655-677.
Yang et al., "Long Term Exendin-4 Treatment Reduces Food Intake and Body Weight and Alters Expression of Brain Homeostatic and Reward Markers," Endocrinology, Sep. 2014, 155(9): 3473-3483.
Yang et al., "Plasma IP-10 and MCP-3 levels are highly associated with disease severity and predict the progression of COVID-19," J Allergy Clin Immunol, 2020, 146: 119-127.
Yang et al., "Poly(carboxybetaine) nanomaterials enable long circulation and prevent polymer-specific antibody production," Nano Today, Feb. 2014, 9(1):10-16.
Yang et al., "Uricases as therapeutic agents to treat refractory gout: Current states and future directions," Drug Dev Res, 2012, 73(2): 66-72.
Yates et al., "Contemporary management of patients with high-risk non-muscle-invasive bladder cancer who fail intravesical BCG therapy," World journal of urology, May 2011, 29(4): 415-422.
Yeh et al., "Micromolding of shape-controlled, harvestable cell-laden hydrogels," Biomaterials, 2006, 27: 5391-5398.
Yeo et al., "Coacervation of tropoelastin," Adv Colloid Interface Sci, Sep. 2011, 167(1-2): 94-103.
Yokoe et al., "Albumin-conjugated PEG liposome enhances tumor distribution of liposomal doxorubicin in rats," International Journal of Pharmaceutics, May 2008, 353(1-2): 28-34.

(56) References Cited

OTHER PUBLICATIONS

Yong et al., "Connecting clusters of COVID-19: an epidemiological and serological investigation," Lancet Infect Dis, 2020, 20: 809-815.
Yoo et al., "A systemic Small RNA Signaling System in Plants" The Plant Cell (2004) vol. 16, pp. 1979-2000.
Yoo et al., "Biodegradable Nanoparticles Containing Doxorubicin-Plga Conjugate for Sustained Release," Pharm. Res., 1999, 16(7):1114-1118.
Youn et al., "Evaluation of therapeutic potentials of site-specific PEGylated glucagon-like peptide-1 isomers as a type 2 anti-diabetic treatment: Insulinotropic activity, glucose-stabilizing capability, and proteolytic stability" Biochem. Pharmacol, 2007, 73: 84-93.
Youn et al., "High-yield production of biologically active mono-PEGylated salmon calcitonin by site-specific PEGylation," J. Control. Release, Feb. 2007, 117(3):371-379.
Yousefpour et al., "Co-opting biology to deliver drugs," Biotechnol Bioeng, Sep. 2014, 111(9): p. 1699-1716.
Yousefpour et al., "Genetically Encoding Albumin Binding into Chemotherapeutic-loaded Polypeptide Nanoparticles Enhances Their Antitumor Efficacy," Nano Lett., Dec. 2018, 18(12): 7784-7793.
Yu et al., "Effectiveness and security of CT-guided percutaneous implantation of (125)I seeds in pancreatic carcinoma," The British journal of radiology, Jul. 2014, 87(1039): 20130642, 7 pages.
Yusta et al., "GLP-1 receptor activation improves β cell function and survival following induction of endoplasmic reticulum stress," Cell Metab, Nov. 2006, 4(5):391-406.
Zhang et al., "A self-assembly pathway to aligned monodomain gels," Nat. Mater., Jul. 2010, 9(7): 594-601.
Zhang et al., "Anti-PEG antibodies in the clinic: Current issues and beyond PEGylation," J Control Release, 2016, 244(Pt B): 184-193.
Zhang et al., "Impact of Large Aggregated Uricases and PEG Diol on Accelerated Blood Clearance of PEGylated Canine Uricase," PLoS One, 2012, 7(6): e39659.
Zhang et al., "In Depth Analysis on the Unusual Multistep Aggregation Process of Oligo(ethylene glycol) Methacrylate-Based Polymers in Water," Macromolecules, Jul. 2014, 47(14): 4728-4737.
Zhang et al., "Nanoparticles in medicine: therapeutic applications and developments," Clin. Pharmacol. Ther., May 2008, 83(5):761-769.
Zhang et al., "Novel agents for pancreatic ductal adenocarcinoma: emerging therapeutics and future directions," Jounral of Hematology & Oncology, Jan. 2018, 11:14, 17 pages.
Zhang et al., "Sensitive and Quantitative Detection of Anti-Poly(ethylene glycol) (PEG) Antibodies by Methoxy-PEG-Coated Surface Plasmon Resonance Sensors," Anal Chem, Aug. 2017, 89(16): 8217-8222.
Zhang et al., "Shape Effects of Nanoparticles Conjugated with Cell-Penetrating Peptides (HIV Tat PTD) on CHO Cell Uptake," Bioconjugate Chem, Sep. 2008, 19(9):1880-1887.
Zhao et al., "A new Bliss Independence model to analyze drug combination data," J Biomol Screen, Jun. 2014, 19(5): 817-821.
Zhao et al., "Antibody responses to SARS-CoV-2 in patients of novel coronavirus disease 2019," Clin Infect Dis, 2020, 22 pages.
Zhao et al., "Cellular uptake, intracellular trafficking, and cytotoxicity of nanomaterials," Small, Wiley, May 2011, 7(10):1322-37.
Zhao et al., "Fluorescence probe techniques used to study micelle formation in water-soluble block copolymers," Langmuir 1990, 6(2):514-516.
Zhao et al., "Tumor αvβ3 Integrin Is a Therapeutic Target for Breast Cancer Bone Metastases," Cancer Res, AACR Publications, Jun. 2007, 67(12):5821-30.
Zimm, "Apparatus and Methods for Measurement and Interpretation of the Angular Variation of Light Scattering; Preliminary Results on Polystyrene Solutions," J. Chem. Phys. 1948, 16, 1099-1116.
Zini et al., "Contemporary management of adrenocortical carcinoma," European urology, Nov. 2011, 60(5): 1055-1065.
Zong et al., "Crystal structures of *Staphylococcus aureus* sortase A and its substrate complex," J. Biol. Chem. 279, 2004, 31383-31389.
Zununi Vahed et al., "Targeted cancer drug delivery with aptamer-functionalized polymeric nanoparticles," Journal of drug targeting, Mar. 2019, 27(3):292-299.
International Search Report and Written Opinion for Application No. PCT/US2008/084159 dated Feb. 27, 2009 (8 pages).
International Search Report and Written Opinion for Application No. PCT/US2016/024202 dated Aug. 26, 2016 (9 pages).
International Search Report and Written Opinion for Application No. PCT/US2016/045655 dated Dec. 2, 2016 (13 pages).
International Search Report and Written Opinion for Application No. PCT/US2016/068141 dated Jul. 19, 2017 (12 pages).
International Search Report and Written Opinion for Application No. PCT/US2016/068142 dated Jul. 19, 2017 (12 pages).
International Search Report and Written Opinion for Application No. PCT/US2018/032785 dated Sep. 25, 2018 (16 pages).
International Search Report and Written Opinion for Application No. PCT/US2017/035530 dated Aug. 23, 2017 (13 pages).
International Search Report and Written Opinion for Application No. PCT/US2017/052887 dated Jan. 26, 2018 (20 pages).
International Search Report and Written Opinion for Application No. PCT/US2017/051661 dated Jan. 2, 2018 (12 pages).
International Search Report and Written Opinion for Application No. PCT/US2018/013611 dated May 30, 2018 (18 pages).
International Search Report and Written Opinion for Application No. PCT/US2018/040409 dated Nov. 5, 2018 (16 pages).
International Search Report and Written Opinion for Application No. PCT/US2019/015176 dated Jun. 3, 2019 (12 pages).
International Search Report and Written Opinion for Application No. PCT/US2019/023583 dated Jul. 5, 2019 (10 pages).
International Search Report and Written Opinion for Application No. PCT/US2019/030022 dated Jul. 25, 2019 (8 pages).
International Search Report and Written Opinion for Application No. PCT/US2019/044911 dated Dec. 10, 2019 (11 pages).
International Search Report and Written Opinion for Application No. PCT/US2019/050077 dated Jan. 27, 2020 (19 pages).
International Search Report and Written Opinion for Application No. PCT/US2019/061144 dated May 21, 2020 (15 pages).
International Search Report and Written Opinion for Application No. PCT/US2021/020589 dated Jul. 15, 2021 (21 pages).
International Search Report and Written Opinion for Application No. PCT/US2021/017809 dated Jul. 22, 2021 (20 pages).
International Search Report and Written Opinion for Application No. PCT/US2021/020591 dated Oct. 7, 2021 (14 pages).
International Search Report and Written Opinion for Application No. PCT/US2021/046833 dated Nov. 8, 2021 (13 pages).
International Search Report and Written Opinion for Application No. PCT/US2021/035823 dated Dec. 8, 2021 (16 pages).
Japanese Patent Office Action for Application No. 2019-515805 dated Aug. 2, 2021 (10 pages, English translation included).
European Patent Office Extended Search Report for Application No. 17853962.3 dated Mar. 3, 2020 (8 pages).
European Patent Office Action for Application No. 17853962.3 dated May 3, 2021 (4 pages).
United States Patent Office Action for U.S. Appl. No. 13/904,836 dated Mar. 27, 2014 (10 pages).
United States Patent Office Notice of Allowance for U.S. Appl. No. 13/904,836 dated Jul. 30, 2014 (6 pages).
United States Patent Office Action for U.S. Appl. No. 13/942,037 dated Jan. 15, 2016 (19 pages).
United States Patent Office Action for U.S. Appl. No. 13/942,037 dated Jun. 4, 2015 (33 pages).
United States Patent Office Action for U.S. Appl. No. 13/942,037 dated Nov. 28, 2016 (22 pages).
United States Patent Office Action for U.S. Appl. No. 13/942,037 dated Feb. 9, 2018 (29 pages).
United States Patent Office Notice of Allowance for U.S. Appl. No. 13/245,459 dated Feb. 27, 2013 (13 pages).
United States Patent Office Action for U.S. Appl. No. 14/572,391 dated Oct. 26, 2016 (11 pages).
United States Patent Office Notice of Allowance for U.S. Appl. No. 14/572,391 dated Jun. 16, 2017 (10 pages).
United States Patent Office Action for U.S. Appl. No. 15/387,536 dated Sep. 27, 2018 (11 pages).

(56) References Cited

OTHER PUBLICATIONS

United States Patent Office Action for U.S. Appl. No. 15/387,540 dated Sep. 27, 2018 (12 pages).
United States Patent Office Action for U.S. Appl. No. 15/561,799 dated Dec. 27, 2018 (8 pages).
United States Patent Office Notice of Allowance for U.S. Appl. No. 15/387,536 dated Mar. 13, 2019 (13 pages).
United States Patent Office Notice of Allowance for U.S. Appl. No. 15/561,799 dated Apr. 2, 2019 (6 pages).
United States Patent Office Notice of Allowance for U.S. Appl. No. 15/387,540 dated Apr. 17, 2019 (9 pages).
United States Patent Office Action for U.S. Appl. No. 16/058,924 dated Nov. 26, 2019 (23 pages).
United States Patent Office Action for U.S. Appl. No. 16/064,424 dated Apr. 22, 2020 (18 pages).
United States Patent Office Action for U.S. Appl. No. 16/064,425 dated Apr. 22, 2020 (18 pages).
United States Patent Office Action for U.S. Appl. No. 16/058,924 dated Jul. 6, 2020 (51 pages).
United States Patent Office Action for U.S. Appl. No. 15/749,797 dated May 11, 2020 (14 pages).
United States Patent Office Action for U.S. Appl. No. 15/749,797 dated Oct. 20, 2020 (16 pages).
United States Patent Office Action for U.S. Appl. No. 16/335,734 dated Nov. 20, 2020 (15 pages).
United States Patent Office Action for U.S. Appl. No. 16/525,374 dated Dec. 7, 2020 (9 pages).
United States Patent Office Action for U.S. Appl. No. 16/305,696 dated Jan. 28, 2021 (15 pages).
United States Patent Office Notice of Allowance for U.S. Appl. No. 16/332,865 dated Apr. 2, 2021 (10 pages).
United States Patent Office Action for U.S. Appl. No. 16/477,229 dated Apr. 12, 2021 (14 pages).
United States Patent Office Action for U.S. Appl. No. 15/749,797 dated May 12, 2021 (19 pages).
United States Patent Office Notice of Allowance for U.S. Appl. No. 16/332,865 dated May 17, 2021 (5 pages).
United States Patent Office Notice of Allowance for U.S. Appl. No. 16/335,734 dated Jun. 16, 2021 (9 pages).
United States Patent Office Action for U.S. Appl. No. 16/305,696 dated Jun. 22, 2021 (20 pages).
United States Patent Office Action for U.S. Appl. No. 16/614,282 dated Oct. 21, 2021 (14 pages).
United States Patent Office Action for U.S. Appl. No. 15/749,797 dated Nov. 29, 2021 (10 pages).
United States Patent Office Action for U.S. Appl. No. 16/477,229 dated Oct. 26, 2021 (10 pages).
Australian Patent Office Examination Report No. 1 for Application No. 2016301391 dated Nov. 5, 2021 (3 pages).
United States Patent Office Action for U.S. Appl. No. 17/265,165 dated Dec. 21, 2021 (11 pages).
United States Patent Office Action for U.S. Appl. No. 16/964,832 dated Jan. 19, 2022 (12 pages).
United States Patent Office Action for U.S. Appl. No. 16/625,899 dated Dec. 15, 2021 (12 pages).
United States Patent Office Action for U.S. Appl. No. 16/927,982 dated Jan. 6, 2022 (6 pages).
Da Pieve Chiara et al., "Modification of Thiol Functionalized Aptamers by Conjugation of Synthetic Polymers," Bioconjugate Chemistry, 2009, 1(1): 169-174.
International Search Report and Written Opinion for Application No. PCT2022/023158 dated Jun. 21, 2022 (7 pages).
International Search Report and Written Opinion for Application No. PCT/US2022/017349 dated Jun. 3, 2022 (20 pages).
United States Patent Office Action for U.S. Appl. No. 16/964,832 dated Jul. 14, 2022 (6 pages).
United States Patent Office Notice of Allowance for U.S. Appl. No. 16/927,982 dated Jul. 15, 2022 (8 pages).
United States Patent Office Notice of Allowance for U.S. Appl. No. 16/614,282 dated Aug. 23, 2022 (7 pages).
Ren et al., "Stimulus-Responsive Polymer Prodrugs," Progress in Chemistry, 2013, 25(5): 10 pages.
Japanese Patent Office Action for Application No. 2019-515805 dated May 23, 2022 (7 pages, English translation Included).
Chinese Patent Office Action for Application No. 201780065486.9 dated Jun. 9, 2022 (24 pages, English translation included).
United States Patent Office Action for U.S. Appl. No. 16/614,282 dated Apr. 27, 2022 (15 pages).
United States Patent Office Notice of Allowance for U.S. Appl. No. 16/305,696 dated May 23, 2022 (10 pages).
United States Patent Office Notice of Allowance for U.S. Appl. No. 16/305,696 dated Jun. 10, 2022 (4 pages).
United States Patent Office Notice of Allowance for U.S. Appl. No. 15/749,797 dated Jun. 2, 2022 (6 pages).
United States Patent Office Action for U.S. Appl. No. 16/477,229 dated Jun. 13, 2022 (11 pages).
Chan et al., "A randomized, repeat-dose, pharmacodynamic and safety study of an antidote-controlled factor IXa inhibitor," J Thromb Haemost, 2008, 6(5): 789-796.
Chan et al., "Phase 1b randomized study of antidote-controlled modulation of factor IXa activity in patients with stable coronary artery disease," Circulation, 2008, 117(22): 2865-2874.
Chappell et al., "Computational design of small transcription activating RNAs for versatile and dynamic gene regulation," Nat Commun, 2017, 8(1): 1051.
Chappell et al., "Creating small transcription activating RNAs," Nat Chem Biol, 2015, 11(3): 214-220.
Chase et al., "Single-Stranded DNA Binding Proteins Required for DNA Replication," Ann. Rev. Biochem., 1986, 55: 103-136.
Cohen et al., "First clinical application of an actively reversible direct factor IXa inhibitor as an anticoagulation strategy in patients undergoing percutaneous coronary intervention," Circulation, 2010, 122(6): 614-622.
Dale et al., "Direct covalent mercuration of nucleotides and polynucleotides," Biochemistry, 1975, 14(11): 2447-2457.
Davis et al., "Antibodies and the RNA World: A Role for Low-molecular-weight Effectors in Biochemical Evolution," RNA World, 1993, Chapter 8, p. 185-204.
Dyke et al., "First-in-human experience of an antidote-controlled anticoagulant using RNA aptamer technology: a phase 1a pharmacodynamic evaluation of a drug-antidote pair for the controlled regulation of factor IXa activity," Circulation, 2006, 114(23): 2490-2497.
Eichhorn et al., "Interactions of metal ions with polynucleotides and related compounds. XII. The relative effect of various metal ions on DNA helicity," J. Am. Chem. Soc, 1968, 90: 7323-7328.
Ganesan et al., "Lipid Nanoparticles: Different Preparation Techniques, Characterization, Hurdles, and Strategies for the Production of Solid Lipid Nanoparticles and Nanostructured Lipid Carriers for Oral Drug Delivery," Sustain. Chem. Pharm., 2017, 6: 37-56.
Gold et al., "Aptamers and the RNA World, Past and Present," Cold Spring Harbor Perspect. Biol., 2012, 4: a003582, 9 pages.
Heus, "RNA aptamers," Nat Struct Biol, 1997, 4(8): 597-600.
Hucknall et al., "Simple Fabrication of Antibody Microarrays on Nonfouling Polymer Brushes with Femtomolar Sensitivity for Protein Analytes in Serum and Blood," Adv Mater, 2009, 21: 1968-1971.
Hwang et al., "Inhibition of gene expression in human cells through small molecule-RNA interactions," Proc. Natl. Acad. Sci. USA, 1999, 96(23): 12997-13002.
Keefe et al., "Aptamers as therapeutics," Nature Reviews Drug Discovery, 2010, 9: 537-550.
Korte et al., "Short activated partial thromboplastin times are related to increased thrombin generation and an increased risk for thromboembolism," Am J Clin Pathol, 2000, 113(1): 123-127.
Li et al., "Ferric Chloride-induced Murine Thrombosis Models," J. Vis. Exp., 2016, 115: e54479, 12 pages.
Lincoff et al., "Effect of the REG1 anticoagulation system versus bivalirudin on outcomes after percutaneous coronary intervention (REGULATE-PCI): a randomised clinical trial," Lancet, 2016, 387(10016): 349-356.

(56) References Cited

OTHER PUBLICATIONS

Lippard et al., "Platinum complexes: probes of polynucleotide structure and antitumor drugs," Acc. Chem. Res., 1978, 11(5): 211-217.
Maier et al., "From selection hits to clinical leads: progress in aptamer discovery, " Mol. Ther. Methods Clin. Dev., 2016, 3: 16014, 10 pages.
Mcmanus et al., "Gene silencing in mammals by small interfering RNAs," Nat Rev Genet, 2002, 3(10): 737-747.
Moreno et al., "Anti-PEG Antibodies Inhibit the Anticoagulant Activity of PEGylated Aptamers," Cell Chem Biol, 2019, 26(5): 634-644.e3.
Nimjee et al., "Aptamers as Therapeutics," Annu Rev Pharmacol Toxicol, 2017, 57: 61-79.
Pisal et al., "Delivery of therapeutic proteins," Journal of Pharmaceutical Sciences, 2010, 99(6): 2557-2575.
Povsic et al., "A Phase 2, randomized, partially blinded, active-controlled study assessing the efficacy and safety of variable anticoagulation reversal using the REG1 system in patients with acute coronary syndromes: results of the RADAR trial," Eur Heart J, 2013, 34(31): 2481-2489.
Povsic et al., "Pre-existing anti-PEG antibodies are associated with severe immediate allergic reactions to pegnivacogin, a PEGylated aptamer," J Allergy Clin Immunol, 2016, 138(6): 1712-1715.
Purtell et al., "Isoelectric point of albumin: effect on renal handling of albumin," Kidney Int, 1979, 16(3): 366-376.
Richter et al., "Mechanistic determinants of biotherapeutics absorption following SC administration," AAPS J, 2012, 14(3): 559-570.
Rinaldi et al., "Antisense oligonucleotides: the next frontier for treatment of neurological disorders," Nat Rev Neurol, 2018, 14(1): 9-21.
Rusconi et al., "Antidote-mediated control of an anticoagulant aptamer in vivo," Nat Biotechnol, 2004, 22(11): 1423-1428.
Rusconi et al., "RNA aptamers as reversible antagonists of coagulation factor Ixa," Nature, 2002, 19(6902): 90-94.
Shu et al., "GISAID: Global initiative on sharing all influenza data—from vision to reality," Euro Surveill 22, 2017, 22(13): 30494, 3 pages.
Smith et al., "Coronaviruses lacking exoribonuclease activity are susceptible to lethal mutagenesis: evidence for proofreading and potential therapeutics," PLoS Pathog, 2013, 9: e1003565, 11 pages.
Tuerk et al., "Systematic evolution of ligands by exponential enrichment: RNA ligands to bacteriophage T4 DNA polymerase," Science, 1990, 249(4968): 505-510.
Werstuck et al., "Controlling gene expression in living cells through small molecule-RNA interactions," Science, 1998, 282(5387): 296-298.
Woodruff et al., "Modulation of the Coagulation Cascade Using Aptamers," Arterioscler Thromb Vasc Biol, 2015, 35(10): 2083-2091.
Yamaoka et al., "Distribution and tissue uptake of poly(ethylene glycol) with different molecular weights after intravenous administration to mice," Journal of Pharmaceutical Sciences, 1994, 83(4): 601-606.
Yizhi et al., "A brush-polymer/exendin-4 conjugate reduces blood glucose levels for up to five days and eliminates poly(ethylene glycol) antigenicity," Nature Biomedical Engineering, 2016, 1(1): 0002.
Zhou et al., "Aptamers as targeted therapeutics: current potential and challenges," Nat Rev Drug Discov, 2017, 16(3): 181-202.
Gilroy et al., "Sustained release of a GLP-1 and FGF21 dual agonist from an injectable depot protects mice from obesity and hyperglycemia," Science Advances, 2020, 6(35): eaaz9890, 12 pages.
United States Patent Office Action for U.S. Appl. No. 16/477,229 dated Mar. 3, 2022 (10 pages).
United States Patent Office Notice of Allowance for U.S. Appl. No. 15/749,797 dated Mar. 16, 2022 (6 pages).
U.S. Appl. No. 13/245,459, filed Sep. 26, 2011, U.S. Pat. No. 8,470,967, Jun. 25, 2013.
U.S. Appl. No. 13/904,836, filed May 29, 2013, U.S. Pat. No. 8,912,310, Dec. 16, 2014.
U.S. Appl. No. 14/572,391, filed Dec. 16, 2014, U.S. Pat. No. 9,771,396, Jun. 25, 2013.
U.S. Appl. No. 15/679,751, filed Aug. 17, 2017, 2018/0037609, Feb. 8, 2018.
U.S. Appl. No. 62/138,847, filed Mar. 26, 2015.
PCT/US2016/024202, Mar. 25, 2016, WO2016/154530, Sep. 26, 2016.
U.S. Appl. No. 15/561,799, filed Sep. 26, 2017 2019, U.S. Pat. No. 10,385,115, Aug. 20, 2019.
U.S. Appl. No. 16/525,374, filed Jul. 29, 2019, 2019/0345228, Nov. 14, 2019.
U.S. Appl. No. 62/399,123, filed Sep. 23, 2016.
PCT/US2017/052887, Sep. 22, 2017, WO2018/057847, Mar. 29, 2018.
U.S. Appl. No. 16/335,734, filed Mar. 22, 2019, 2020/0017557, Jan. 16, 2020.
U.S. Appl. No. 17/477,192, filed Sep. 16, 2021.
U.S. Appl. No. 13/942,037, filed Jul. 15, 2015, 2014/0024600, Jan. 23, 2014.
U.S. Appl. No. 16/058,924, filed Aug. 8, 2018, 2019/0023743, Jan. 24, 2019.
U.S. Appl. No. 62/270,401, filed Dec. 21, 2015.
U.S. Appl. No. 62/310,534, filed Mar. 18, 2016.
U.S. Appl. No. 62/329,800, filed Apr. 29, 2016.
U.S. Appl. No. 62/407,403, filed Oct. 12, 2016.
PCT/US2016/068141, Dec. 21, 2016, WO2017/112825, Jun. 29, 2017.
PCT/US2016/068142, Dec. 21, 2016, WO2017/112826, Jun. 29, 2017.
U.S. Appl. No. 15/387,536, filed Dec. 21, 2016, U.S. Pat. No. 10,364,451, Jul. 30, 2019.
U.S. Appl. No. 15/387,540, filed Dec. 21, 2016, U.S. Pat. No. 10,392,611, Aug. 27, 2019.
U.S. Appl. No. 16/064,424, filed Jun. 20, 2018, 2019/0015520, Jan. 17, 2019.
U.S. Appl. No. 16/064,425, filed Sep. 12, 2016, 2018/0369399, Dec. 27, 2018.
U.S. Appl. No. 62/506,593, filed May 15, 2017.
U.S. Appl. No. 62/534,442, filed Jul. 19, 2017.
U.S. Appl. No. 62/544,720, filed Aug. 11, 2017.
U.S. Appl. No. 62/545,313, filed Aug. 14, 2017.
PCT/US20168/032785, May 15, 2018, WO2018/213320, Nov. 22, 2018.
U.S. Appl. No. 16/614,282, filed Nov. 15, 2019, 2021/0154143, May 27, 2021.
U.S. Appl. No. 62/200,726, filed Aug. 4, 2015.
PCT/US2016/045655, Aug. 4, 2016, WO2017/024182, Feb. 9, 2017.
U.S. Appl. No. 15/749,797, filed Feb. 2, 2018, 2018/0228908, Aug. 16, 2018.
U.S. Appl. No. 62/394,662, filed Sep. 14, 2016.
PCT/US2017/051661, Sep. 14, 2017, WO2018/053201, Mar. 22, 2018.
U.S. Appl. No. 16/332,865, filed Mar. 13, 2019, U.S. Pat. No. 11,135,301, May 10, 2021.
U.S. Appl. No. 62/445,504, filed Jan. 12, 2017.
U.S. Appl. No. 62/479,977, filed Mar. 31, 2017.
PCT/US2018/013611, Jan. 12, 2018, WO2018/132732, Jul. 19, 2018.
U.S. Appl. No. 16/477,229, filed Jul. 11, 2019, 2019/0328662, Oct. 31, 2019.
U.S. Appl. No. 62/527,836, filed Jun. 30, 2017.
U.S. Appl. No. 62/534,019, filed Jul. 18, 2017.
PCT/US2018/040409, Jun. 29, 2018, WO2019/006374, Jan. 3, 2019.
U.S. Appl. No. 16/625,899, filed Dec. 23, 2019, 2020/0148724, May 14, 2020.
U.S. Appl. No. 62/343,926, filed Jun. 1, 2016.
U.S. Appl. No. 62/414,877, filed Oct. 31, 2016.
PCT/US2017/035530, Jun. 1, 2017, WO2017/210476, Dec. 7, 2018.

(56) References Cited

OTHER PUBLICATIONS

U.S. Appl. No. 16/305,696, filed Nov. 29, 2018, 2020/0378916, Dec. 3, 2020.
U.S. Appl. No. 62/728,582, filed Sep. 7, 2018.
PCT/US2019/050077, Sep. 6, 2019, WO2020/051541, Mar. 12, 2020.
U.S. Appl. No. 17/272,887, filed Mar. 2, 2021, 2021/0316007, Oct. 14, 201.
U.S. Appl. No. 62/767,736, filed Nov. 15, 2018.
PCT/US2019/061144, Nov. 13, 2019, WO2020/102324, May 22, 2020.
U.S. Appl. No. 17/294,368, filed May 14, 2021, 2022/0008567, Jan. 13, 2022.
U.S. Appl. No. 62/622,249, filed Jan. 26, 2018.
PCT/US2019/015176, Jan. 25, 2019, WO2019/147954, Aug. 1, 2019.
U.S. Appl. No. 16/964,832, filed Jul. 24, 2020, 2021/0060171, Mar. 4, 2021.
U.S. Appl. No. 62/647,199, filed Mar. 23, 2018.
PCT/US2019/023583, Mar. 22, 2019, WO2019/183476, Sep. 26, 2019.
U.S. Appl. No. 62/664,512, filed Apr. 30, 2018.
PCT/US2019/030022, Apr. 30, 2019, WO2019/213150, Nov. 7, 2019.
U.S. Appl. No. 17/051,202, filed Oct. 28, 2020.
U.S. Appl. No. 62/700,939, filed Jul. 20, 2018.
U.S. Appl. No. 62/873,306, filed Jul. 12, 2019.
U.S. Appl. No. 16/927,982, filed Jul. 13, 2020, 2021/0009999, Jan. 14, 2021.
U.S. Appl. No. 62/713,752, filed Aug. 2, 2018.
PCT/US2019/044911, Aug. 2, 2019, WO2020/028806, Feb. 6, 2020.
U.S. Appl. No. 17/265,165, filed Feb. 1, 2021, 2021/0309722, Oct. 7, 2021.
U.S. Appl. No. 62/985,174, filed Mar. 4, 2020.
PCT/US2021/020589, Mar. 3, 2021, WO2021/178481, Sep. 10, 2021.
U.S. Appl. No. 62/985,179, filed Mar. 4, 2020.
PCT/US2021/020591, Mar. 3, 2021, WO2021/178483, Sep. 10, 2021.
U.S. Appl. No. 62/898,353, filed Sep. 12, 2019.
U.S. Appl. No. 17/015,315, filed Sep. 9, 2020, 2021/0046188, Feb. 18, 2021.
U.S. Appl. No. 62/975,479, filed Feb. 12, 2020.
PCT/US2021/017809, Feb. 12, 2021, WO2021/163445, Aug. 19, 2021.
U.S. Appl. No. 63/035,173, filed Jun. 5, 2020.
PCT/US2021/035823, Jun. 4, 2021, WO2021/247952, Dec. 9, 2021.
U.S. Appl. No. 63/068,432, filed Aug. 21, 2020.
U.S. Appl. No. 63/116,511, filed Nov. 20, 2020.
PCT/US2021/046833, Aug. 20, 2021.
U.S. Appl. No. 63/236,064, filed Aug. 23, 2021.
Erbacher et al., "Transfection and Physical Properties of Various Saccharide, Poly(ethylene glycol), and Antibody-Derivatized Polyethylenimines (PEI)," The Journal of Gene Medicine, 1999, 1: 210-222.
Alves et al., "Influence of doxorubicin on model cell membrane properties: insight from in vitro and in silico studies," Sci Rep, 2017, 7(1): 6343.
International Search Report and Written Opinion for Application No. PCT/US2022/078659 dated Feb. 1, 2023 (17 pages).
Indian Patent Office Examination Report for Application No. 201917013513 dated Mar. 31, 2023 (8 pages).
United States Patent Office Action for U.S. Appl. No. 16/964,832 dated Apr. 17, 2023 (17 pages).
Ozer et al., "Injectable non-immunogenic PEG-like conjugate that forms a subcutaneous depot and enables sustained delivery of a peptide drug," Research Square, 2021, 38 pages.
Hu et al., "Site-specific in situ growth of a cyclized protein-polymer conjugate with improved stability and tumor retention," Biomaterials, 2015, 47:13-19.
International Search Report and Written Opinion for Application No. PCT/US2022/041241 dated Oct. 25, 2022 (10 pages).
European Patent Office Action for Application No. 17853962.3 dated Nov. 8, 2022 (5 pages).
Korean Patent Office Action for Application No. 10-2019-7011467 dated Oct. 21, 2022 (9 pages, English translation included).
United States Patent Office Action for U.S. Appl. No. 17/265,165 dated Sep. 2, 2022 (5 pages).
United States Patent Office Action for U.S. Appl. No. 17/015,315 dated Dec. 23, 2022 (10 pages).
United States Patent Office Notice of Allowance for U.S. Appl. No. 16/477,229 dated Jan. 6, 2023 (8 pages).
United States Patent Office Notice of Allowance for U.S. Appl. No. 17/265,165 dated Jan. 10, 2023 (7 pages).
United States Patent Office Notice of Allowance for U.S. Appl. No. 16/625,899 dated Jan. 18, 2023 (8 pages).
Cereghetti et al., "Reversible, functional amyloids: towards an understanding of their regulation in yeast and humans," Cell Cycle, 2018, 17(13): 1545-1558.
Uversky et al., "Life in Phases: Intra- and Inter-Molecular Phase Transitions in Protein Solutions," Biomolecules, 2019, 9(12): 842.
McPherson, "Product purification by reversible phase transition following Escherichia coli expression of genes encoding up to 251 repeats of the elastomeric pentapeptide GVGVP," Protein Expression and Purification, 1996, 7: 51-57.
Cascarina et al., "Generalizable Compositional Features Influencing the Proteostatic Fates of Polar Low-Complexity Domains," International Journal of Molecular Sciences, 2021, 22(16): 8944.
Krainer et al., "Reentrant liquid condensate phase of proteins is stabilized by hydrophobic and non-ionic interactions," Nature Communications, 2021, 12(1): 1085.
United States Patent Office Notice of Allowance for U.S. Appl. No. 18/051,487 dated Dec. 11, 2023 (5 pages).
United States Patent Office Action for U.S. Appl. No. 16/964,832 dated Jan. 19, 2024 (9 pages).
United States Patent Office Action for U.S. Appl. No. 17/051,202 dated Jan. 19, 2024 (5 pages).
European Patent Office Action for Application No. 17853962.3 dated Jul. 22, 2024 (3 pages).

```
                            SEQUENCE LISTING

<160> NUMBER OF SEQ ID NOS: 23

<210> SEQ ID NO 1
<211> LENGTH: 10
<212> TYPE: PRT
<213> ORGANISM: Homo sapien

<400> SEQUENCE: 1

Gly Ala Gly Val Pro Gly Val Gly Val Pro
1               5                   10

<210> SEQ ID NO 2
<211> LENGTH: 25
<212> TYPE: PRT
<213> ORGANISM: Homo sapien

<400> SEQUENCE: 2

Gly Val Gly Val Pro Gly Val Gly Val Pro Gly Ala Gly Val Pro Gly
1               5                   10                  15

Val Gly Val Pro Gly Val Gly Val Pro
            20                  25

<210> SEQ ID NO 3
<211> LENGTH: 200
<212> TYPE: PRT
<213> ORGANISM: Homo sapien

<400> SEQUENCE: 3

Gly Val Gly Val Pro Gly Val Gly Val Pro Gly Ala Gly Val Pro Gly
1               5                   10                  15

Val Gly Val Pro Gly Val Gly Val Pro Gly Val Gly Val Pro Gly Val
            20                  25                  30

Gly Val Pro Gly Ala Gly Val Pro Gly Val Gly Val Pro Gly Val Gly
        35                  40                  45

Val Pro Gly Val Gly Val Pro Gly Val Gly Val Pro Gly Ala Gly Val
    50                  55                  60

Pro Gly Val Gly Val Pro Gly Val Gly Val Pro Gly Val Gly Val Pro
65                  70                  75                  80

Gly Val Gly Val Pro Gly Ala Gly Val Pro Gly Val Gly Val Pro Gly
                85                  90                  95

Val Gly Val Pro Gly Val Gly Val Pro Gly Val Gly Val Pro Gly Ala
            100                 105                 110

Gly Val Pro Gly Val Gly Val Pro Gly Val Gly Val Pro Gly Val Gly
        115                 120                 125

Val Pro Gly Val Gly Val Pro Gly Ala Gly Val Pro Gly Val Gly Val
    130                 135                 140

Pro Gly Val Gly Val Pro Gly Val Gly Val Pro Gly Val Gly Val Pro
145                 150                 155                 160
```

```
Gly Ala Gly Val Pro Gly Val Gly Val Pro Gly Val Gly Val Pro Gly
                165                 170                 175

Val Gly Val Pro Gly Val Gly Val Pro Gly Ala Gly Val Pro Gly Val
            180                 185                 190

Gly Val Pro Gly Val Gly Val Pro
        195                 200

<210> SEQ ID NO 4
<211> LENGTH: 200
<212> TYPE: PRT
<213> ORGANISM: Homo sapien

<400> SEQUENCE: 4

Gly Ala Gly Val Pro Gly Val Gly Val Pro Gly Ala Gly Val Pro Gly
1               5                   10                  15

Val Gly Val Pro Gly Ala Gly Val Pro Gly Val Gly Val Pro Gly Ala
            20                  25                  30

Gly Val Pro Gly Val Gly Val Pro Gly Ala Gly Val Pro Gly Val Gly
        35                  40                  45

Val Pro Gly Ala Gly Val Pro Gly Val Gly Val Pro Gly Ala Gly Val
    50                  55                  60

Pro Gly Val Gly Val Pro Gly Ala Gly Val Pro Gly Val Gly Val Pro
65                  70                  75                  80

Gly Ala Gly Val Pro Gly Val Gly Val Pro Gly Ala Gly Val Pro Gly
                85                  90                  95

Val Gly Val Pro Gly Ala Gly Val Pro Gly Val Gly Val Pro Gly Ala
            100                 105                 110

Gly Val Pro Gly Val Gly Val Pro Gly Ala Gly Val Pro Gly Val Gly
        115                 120                 125

Val Pro Gly Ala Gly Val Pro Gly Val Gly Val Pro Gly Ala Gly Val
    130                 135                 140

Pro Gly Val Gly Val Pro Gly Ala Gly Val Pro Gly Val Gly Val Pro
145                 150                 155                 160

Gly Ala Gly Val Pro Gly Val Gly Val Pro Gly Ala Gly Val Pro Gly
                165                 170                 175

Val Gly Val Pro Gly Ala Gly Val Pro Gly Val Gly Val Pro Gly Ala
            180                 185                 190

Gly Val Pro Gly Val Gly Val Pro
        195                 200

<210> SEQ ID NO 5
<211> LENGTH: 400
<212> TYPE: PRT
<213> ORGANISM: Homo sapien

<400> SEQUENCE: 5

Gly Val Gly Val Pro Gly Val Gly Val Pro Gly Ala Gly Val Pro Gly
1               5                   10                  15

Val Gly Val Pro Gly Val Gly Val Pro Gly Val Gly Val Pro Gly Val
            20                  25                  30

Gly Val Pro Gly Ala Gly Val Pro Gly Val Gly Val Pro Gly Val Gly
        35                  40                  45

Val Pro Gly Val Gly Val Pro Gly Val Gly Val Pro Gly Ala Gly Val
    50                  55                  60

Pro Gly Val Gly Val Pro Gly Val Gly Val Pro Gly Val Gly Val Pro
65                  70                  75                  80
```

Gly Val Gly Val Pro Gly Ala Gly Val Pro Gly Val Gly Val Pro Gly
                85                  90                  95

Val Gly Val Pro Gly Val Gly Val Pro Gly Val Gly Val Pro Gly Ala
                100                 105                 110

Gly Val Pro Gly Val Gly Val Pro Gly Val Gly Val Pro Gly Val Gly
            115                 120                 125

Val Pro Gly Val Gly Val Pro Gly Ala Gly Val Pro Gly Val Gly Val
    130                 135                 140

Pro Gly Val Gly Val Pro Gly Val Gly Val Pro Gly Val Gly Val Pro
145                 150                 155                 160

Gly Ala Gly Val Pro Gly Val Gly Val Pro Gly Val Gly Val Pro Gly
            165                 170                 175

Val Gly Val Pro Gly Val Gly Val Pro Gly Ala Gly Val Pro Gly Val
                180                 185                 190

Gly Val Pro Gly Val Gly Val Pro Gly Val Gly Val Pro Gly Val Gly
            195                 200                 205

Val Pro Gly Ala Gly Val Pro Gly Val Gly Val Pro Gly Val Gly Val
    210                 215                 220

Pro Gly Val Gly Val Pro Gly Val Gly Val Pro Gly Ala Gly Val Pro
225                 230                 235                 240

Gly Val Gly Val Pro Gly Val Gly Val Pro Gly Val Gly Val Pro Gly
            245                 250                 255

Val Gly Val Pro Gly Ala Gly Val Pro Gly Val Gly Val Pro Gly Val
                260                 265                 270

Gly Val Pro Gly Val Gly Val Pro Gly Val Gly Val Pro Gly Ala Gly
            275                 280                 285

Val Pro Gly Val Gly Val Pro Gly Val Gly Val Pro Gly Val Gly Val
    290                 295                 300

Pro Gly Val Gly Val Pro Gly Ala Gly Val Pro Gly Val Gly Val Pro
305                 310                 315                 320

Gly Val Gly Val Pro Gly Val Gly Val Pro Gly Val Gly Val Pro Gly
            325                 330                 335

Ala Gly Val Pro Gly Val Gly Val Pro Gly Val Gly Val Pro Gly Val
            340                 345                 350

Gly Val Pro Gly Val Gly Val Pro Gly Ala Gly Val Pro Gly Val Gly
            355                 360                 365

Val Pro Gly Val Gly Val Pro Gly Val Gly Val Pro Gly Val Gly Val
    370                 375                 380

Pro Gly Ala Gly Val Pro Gly Val Gly Val Pro Gly Val Gly Val Pro
385                 390                 395                 400

<210> SEQ ID NO 6
<211> LENGTH: 400
<212> TYPE: PRT
<213> ORGANISM: Homo sapien

<400> SEQUENCE: 6

Gly Ala Gly Val Pro Gly Val Gly Val Pro Gly Ala Gly Val Pro Gly
1               5                   10                  15

Val Gly Val Pro Gly Ala Gly Val Pro Gly Val Gly Val Pro Gly Ala
                20                  25                  30

Gly Val Pro Gly Val Gly Val Pro Gly Ala Gly Val Pro Gly Val Gly
            35                  40                  45

Val Pro Gly Ala Gly Val Pro Gly Val Gly Val Pro Gly Ala Gly Val
    50                  55                  60

-continued

Pro Gly Val Gly Val Pro Ala Gly Val Pro Val Gly Val Pro
65                  70                  75                  80

Gly Ala Gly Val Pro Gly Val Gly Val Pro Ala Gly Val Pro Gly
                85                  90                  95

Val Gly Val Pro Gly Ala Gly Val Pro Gly Val Gly Val Pro Gly Ala
                100                 105                 110

Gly Val Pro Gly Val Gly Val Pro Ala Gly Val Pro Gly Val Gly
            115                 120                 125

Val Pro Gly Ala Gly Val Pro Gly Val Gly Val Pro Gly Ala Gly Val
        130                 135                 140

Pro Gly Val Gly Val Pro Gly Ala Gly Val Pro Gly Val Gly Val Pro
145                 150                 155                 160

Gly Ala Gly Val Pro Gly Val Gly Val Pro Gly Ala Gly Val Pro Gly
                165                 170                 175

Val Gly Val Pro Gly Ala Gly Val Pro Gly Val Gly Val Pro Gly Ala
                180                 185                 190

Gly Val Pro Gly Val Gly Val Pro Gly Ala Gly Val Pro Gly Val Gly
            195                 200                 205

Val Pro Gly Ala Gly Val Pro Gly Val Gly Val Pro Gly Ala Gly Val
        210                 215                 220

Pro Gly Val Gly Val Pro Gly Ala Gly Val Pro Gly Val Gly Val Pro
225                 230                 235                 240

Gly Ala Gly Val Pro Gly Val Gly Val Pro Gly Ala Gly Val Pro Gly
                245                 250                 255

Val Gly Val Pro Gly Ala Gly Val Pro Gly Val Gly Val Pro Gly Ala
                260                 265                 270

Gly Val Pro Gly Val Gly Val Pro Gly Ala Gly Val Pro Gly Val Gly
            275                 280                 285

Val Pro Gly Ala Gly Val Pro Gly Val Gly Val Pro Gly Ala Gly Val
        290                 295                 300

Pro Gly Val Gly Val Pro Gly Ala Gly Val Pro Gly Val Gly Val Pro
305                 310                 315                 320

Gly Ala Gly Val Pro Gly Val Gly Val Pro Gly Ala Gly Val Pro Gly
                325                 330                 335

Val Gly Val Pro Gly Ala Gly Val Pro Gly Val Gly Val Pro Gly Ala
                340                 345                 350

Gly Val Pro Gly Val Gly Val Pro Gly Ala Gly Val Pro Gly Val Gly
            355                 360                 365

Val Pro Gly Ala Gly Val Pro Gly Val Gly Val Pro Gly Ala Gly Val
        370                 375                 380

Pro Gly Val Gly Val Pro Gly Ala Gly Val Pro Gly Val Gly Val Pro
385                 390                 395                 400

<210> SEQ ID NO 7
<211> LENGTH: 200
<212> TYPE: PRT
<213> ORGANISM: Artificial sequence
<220> FEATURE:
<223> OTHER INFORMATION: Synthetic

<400> SEQUENCE: 7

Pro Gly Gly Gly Val Pro Gly Gly Val Pro Gly Ala Val Pro Gly Val
1               5                   10                  15

Pro Gly Ala Val Val Pro Val Val Gly Gly Val Pro Gly Val Val Gly
                20                  25                  30

Val Pro Gly Gly Val Pro Val Gly Val Val Pro Gly Val Pro
        35                  40                  45

Val Gly Val Pro Gly Val Pro Val Val Gly Gly Val Pro Ala Gly
 50                  55                  60

Gly Val Val Pro Gly Gly Gly Pro Val Gly Gly Val Val Pro
 65                  70                  75                  80

Gly Val Gly Val Val Pro Gly Gly Val Pro Val Val Gly Gly Gly
                     85                  90                  95

Val Gly Val Pro Gly Val Val Pro Gly Val Pro Gly Val Gly Val Pro
                    100                 105                 110

Val Gly Gly Val Pro Gly Gly Val Val Pro Gly Gly Val Gly
                    115                 120                 125

Val Pro Val Val Gly Val Val Pro Gly Ala Pro Gly Val Pro Gly Val
                    130                 135                 140

Pro Gly Gly Val Gly Gly Val Pro Val Gly Val Gly Val Pro Gly Gly
145                 150                 155                 160

Gly Ala Pro Gly Val Val Pro Gly Gly Ala Val Pro Gly Gly Ala Pro
                    165                 170                 175

Val Gly Gly Val Gly Gly Val Pro Gly Val Gly Gly Val Pro Gly
                    180                 185                 190

Ala Pro Gly Gly Val Pro Gly Gly
        195                 200

<210> SEQ ID NO 8
<211> LENGTH: 200
<212> TYPE: PRT
<213> ORGANISM: Artificial sequence
<220> FEATURE:
<223> OTHER INFORMATION: Synthetic

<400> SEQUENCE: 8

Pro Gly Gly Val Pro Gly Val Pro Ala Gly Gly Gly Ala Gly Val Pro
 1               5                  10                  15

Gly Val Pro Gly Ala Pro Ala Gly Gly Gly Ala Pro Gly Val Ala Pro
                20                  25                  30

Gly Gly Val Val Pro Gly Val Pro Gly Val Ala Pro Val Val Gly Gly
                35                  40                  45

Gly Ala Pro Gly Gly Val Pro Gly Ala Val Pro Gly Val Pro Gly Gly
                50                  55                  60

Val Pro Gly Gly Val Val Pro Gly Gly Val Gly Ala Pro Gly
 65                  70                  75                  80

Gly Val Ala Pro Val Gly Gly Gly Val Pro Val Val Gly Gly Val Pro
                85                  90                  95

Val Gly Gly Val Ala Pro Gly Val Pro Val Gly Val Pro Gly Val Gly
                100                 105                 110

Val Gly Val Gly Val Pro Val Gly Gly Val Gly Gly Val Pro Gly
                115                 120                 125

Val Val Pro Ala Gly Val Pro Gly Gly Val Ala Gly Val Val Pro
                130                 135                 140

Val Gly Gly Val Pro Val Val Gly Ala Pro Gly Gly Gly Val Gly
145                 150                 155                 160

Val Pro Gly Ala Pro Gly Ala Gly Gly Val Pro Gly Gly Ala Pro Gly
                165                 170                 175

Ala Pro Gly Val Val Ala Pro Gly Gly Val Pro Gly Val Val Val
                180                 185                 190

Pro Gly Val Val Pro Gly Gly Gly
        195             200

<210> SEQ ID NO 9
<211> LENGTH: 400
<212> TYPE: PRT
<213> ORGANISM: Artificial sequence
<220> FEATURE:
<223> OTHER INFORMATION: Synthetic

<400> SEQUENCE: 9

Pro Gly Gly Val Pro Gly Val Gly Gly Val Pro Gly Val Pro Gly
1               5                   10                  15

Ala Pro Gly Val Val Pro Gly Val Val Pro Gly Gly Val Val Pro
            20                  25                  30

Val Gly Gly Val Pro Gly Val Pro Val Val Gly Gly Val Pro Val
            35                  40                  45

Gly Gly Gly Val Gly Gly Val Pro Gly Ala Pro Gly Gly Val Pro
        50                  55                  60

Gly Ala Pro Val Gly Gly Val Pro Val Gly Gly Val Val Pro Gly Val
65                  70                  75                  80

Gly Val Pro Gly Ala Gly Gly Val Pro Gly Val Gly Val Val
                85                  90                  95

Pro Val Gly Gly Gly Ala Pro Gly Gly Val Pro Gly Val Val Pro Gly
                100                 105                 110

Val Pro Val Gly Gly Val Pro Ala Gly Val Val Pro Gly Gly Val Gly
            115                 120                 125

Val Gly Gly Gly Val Val Pro Gly Val Val Gly Val Pro Gly Gly Gly
    130                 135                 140

Val Gly Gly Gly Val Gly Val Pro Gly Gly Ala Pro Gly Gly Gly Val
145                 150                 155                 160

Val Gly Gly Gly Val Pro Gly Gly Val Val Pro Val Pro Val Gly Gly
                165                 170                 175

Val Pro Gly Ala Val Pro Gly Val Pro Gly Val Val Val Pro Val Gly
            180                 185                 190

Gly Gly Val Val Pro Gly Val Pro Gly Gly Val Val Pro Gly
        195                 200                 205

Val Pro Gly Gly Val Val Gly Val Pro Val Val Gly Val Pro Gly Val
    210                 215                 220

Gly Val Val Pro Gly Val Pro Gly Val Pro Val Gly Val Gly Val Val
225                 230                 235                 240

Val Pro Gly Val Val Pro Val Gly Val Gly Val Pro Gly Val Pro Gly
                245                 250                 255

Gly Gly Val Pro Gly Val Gly Val Pro Val Gly Gly Ala Pro Gly Val
            260                 265                 270

Pro Gly Val Pro Gly Val Ala Val Pro Gly Val Val Pro Gly Gly Ala
        275                 280                 285

Pro Gly Val Pro Val Gly Val Val Pro Val Gly Val Val Pro Gly Gly
    290                 295                 300

Gly Val Gly Val Val Pro Gly Gly Val Pro Gly Gly Val Pro Gly Val
305                 310                 315                 320

Pro Ala Gly Val Pro Val Gly Val Pro Val Gly Gly Val Gly Gly Val
                325                 330                 335

Val Pro Gly Gly Gly Ala Pro Gly Val Gly Val Gly Val Pro Ala Gly
            340                 345                 350

Val Pro Gly Gly Val Pro Val Gly Val Gly Val Pro Gly Gly Val
            355                 360                 365

Val Pro Gly Val Pro Ala Gly Gly Val Pro Val Gly Val Pro Gly
            370                 375                 380

Val Gly Gly Val Pro Val Gly Ala Pro Gly Val Pro Gly Gly Val
385                 390                 395                 400

<210> SEQ ID NO 10
<211> LENGTH: 400
<212> TYPE: PRT
<213> ORGANISM: Artificial sequence
<220> FEATURE:
<223> OTHER INFORMATION: Synthetic

<400> SEQUENCE: 10

Pro Ala Gly Ala Val Pro Gly Gly Val Pro Val Ala Gly Gly Val Pro
1               5                   10                  15

Val Gly Ala Gly Val Val Ala Pro Gly Ala Pro Val Gly Gly Ala Pro
            20                  25                  30

Gly Val Val Gly Val Pro Gly Gly Val Pro Gly Val Pro Val Val
            35                  40                  45

Gly Val Gly Val Gly Val Pro Val Gly Gly Val Gly Val Val Pro
    50                  55                  60

Ala Gly Gly Ala Pro Gly Val Gly Val Val Pro Gly Val
65                  70                  75                  80

Val Pro Gly Ala Pro Ala Gly Val Pro Gly Val Ala Pro Gly Gly
                85                  90                  95

Val Gly Gly Val Pro Gly Val Pro Gly Gly Val Val Pro Gly
            100                 105                 110

Val Ala Pro Gly Val Pro Gly Val Pro Gly Gly Val Pro Val Gly Val
            115                 120                 125

Pro Val Gly Ala Ala Pro Gly Gly Val Pro Ala Val Gly Val Pro
130                 135                 140

Gly Val Gly Gly Val Pro Val Val Gly Ala Gly Ala Pro Gly Gly
145                 150                 155                 160

Val Pro Gly Val Ala Val Pro Gly Ala Pro Gly Gly Val Pro Val Gly
                165                 170                 175

Gly Val Pro Gly Gly Val Gly Gly Val Pro Gly Gly Val Pro
            180                 185                 190

Gly Ala Pro Val Gly Val Val Pro Gly Val Val Pro Gly Val
            195                 200                 205

Pro Ala Gly Val Gly Val Pro Gly Ala Pro Gly Ala Pro Gly Gly Gly
210                 215                 220

Val Pro Gly Gly Gly Ala Pro Val Gly Gly Ala Gly Val Pro Gly
225                 230                 235                 240

Gly Val Pro Gly Val Pro Gly Ala Pro Gly Val Gly Val Pro Gly Val
                245                 250                 255

Gly Val Pro Val Gly Val Pro Gly Val Pro Gly Val Pro Val Gly Gly
            260                 265                 270

Gly Ala Gly Val Pro Gly Gly Val Ala Pro Gly Val Ala Val Pro
            275                 280                 285

Gly Val Gly Val Pro Val Val Gly Gly Val Pro Gly Ala Val Pro Gly
            290                 295                 300

Val Pro Gly Val Gly Gly Ala Pro Gly Val Pro Gly Gly Gly Val Val
305                 310                 315                 320

```
Gly Val Gly Val Pro Gly Val Val Pro Gly Val Pro Gly Ala Gly
            325                 330                 335

Ala Pro Gly Gly Gly Ala Pro Gly Ala Pro Val Gly Val Pro Gly Gly
            340                 345                 350

Ala Pro Gly Val Pro Gly Val Gly Gly Val Pro Gly Ala Gly Gly
            355                 360                 365

Gly Val Val Gly Gly Val Val Pro Val Gly Gly Val Val Pro
            370                 375                 380

Gly Ala Pro Gly Gly Ala Pro Val Gly Val Val Gly Gly Val Pro
385                 390                 395                 400

<210> SEQ ID NO 11
<211> LENGTH: 240
<212> TYPE: PRT
<213> ORGANISM: Artificial sequence
<220> FEATURE:
<223> OTHER INFORMATION: Synthetic

<400> SEQUENCE: 11

Pro Val Gly Val Pro Gly Val Gly Gly Ala Pro Val Val Gly Gly
1               5                   10                  15

Ala Pro Val Gly Val Gly Gly Ala Gly Gly Val Val Pro Gly Ala Pro
            20                  25                  30

Val Gly Ala Val Ala Gly Val Gly Ala Pro Gly Gly Ala Val Pro Ala
            35                  40                  45

Gly Gly Ala Pro Gly Val Gly Ala Pro Gly Val Pro Gly Ala Val
            50                  55                  60

Pro Gly Val Gly Val Gly Val Gly Gly Val Val Pro Val
65                  70                  75                  80

Val Val Gly Val Gly Gly Val Pro Ala Gly Ala Val Pro Val Gly Gly
            85                  90                  95

Val Ala Pro Val Gly Val Pro Val Gly Ala Gly Gly Ala Pro Ala
            100                 105                 110

Gly Gly Val Pro Val Ala Val Gly Val Pro Val Gly Gly Gly Val
            115                 120                 125

Pro Gly Val Gly Val Val Gly Val Ala Pro Gly Ala Pro Gly Ala Gly
            130                 135                 140

Val Gly Val Val Ala Gly Ala Gly Ala Ala Val Ala Pro Val Gly
145                 150                 155                 160

Val Ala Pro Gly Val Pro Gly Val Pro Gly Ala Val Val Gly Val Pro
            165                 170                 175

Gly Gly Val Ala Pro Ala Val Val Gly Ala Val Pro Gly Val Val
            180                 185                 190

Gly Val Val Pro Val Gly Ala Pro Val Val Ala Gly Gly Val Ala Val
            195                 200                 205

Ala Pro Val Gly Gly Ala Val Pro Gly Val Pro Gly Gly Val Pro Gly
            210                 215                 220

Gly Gly Ala Pro Gly Ala Pro Val Gly Val Pro Val Gly Val Pro
225                 230                 235                 240

<210> SEQ ID NO 12
<211> LENGTH: 240
<212> TYPE: PRT
<213> ORGANISM: Artificial sequence
<220> FEATURE:
<223> OTHER INFORMATION: Synthetic
```

```
<400> SEQUENCE: 12

Pro Val Gly Ser Pro Gly Ser Val Pro Gly Val Val Pro Val Ser Gly
1               5                   10                  15

Val Val Val Gly Gly Ser Val Pro Gly Ser Ser Pro Val Val Gly
            20                  25                  30

Val Pro Ser Gly Val Pro Val Gly Ser Pro Val Val Gly Gly Val
            35                  40                  45

Ser Pro Gly Val Gly Val Pro Gly Val Val Pro Gly Val Pro Val
    50                  55                  60

Gly Gly Gly Val Gly Val Pro Gly Gly Val Val Gly Gly Val Pro
65                  70                  75                  80

Val Val Val Gly Val Ser Val Pro Ser Gly Val Ser Pro Gly Gly
                85                  90                  95

Val Val Val Pro Val Gly Ser Val Ser Ser Gly Val Pro Val Val Ser
            100                 105                 110

Val Val Gly Val Ser Val Pro Gly Ser Val Pro Val Gly Ser Pro
            115                 120                 125

Ser Ser Gly Val Pro Gly Val Val Pro Gly Ser Pro Gly Gly Val Val
    130                 135                 140

Gly Ser Ser Val Pro Ser Gly Ser Gly Gly Val Ser Val Pro Val Gly
145                 150                 155                 160

Val Gly Gly Ser Gly Val Pro Gly Val Pro Gly Ser Gly Ser Val Val
                165                 170                 175

Pro Val Gly Val Ser Pro Val Gly Gly Gly Ser Gly Ser Val Gly
            180                 185                 190

Ser Gly Ser Pro Gly Gly Ser Val Pro Gly Gly Ser Pro Gly Val Val
    195                 200                 205

Pro Val Gly Ser Pro Gly Val Gly Gly Val Pro Gly Val Val Gly Gly
    210                 215                 220

Ser Gly Ser Pro Gly Val Pro Gly Gly Val Gly Val Pro Gly
225                 230                 235                 240

<210> SEQ ID NO 13
<211> LENGTH: 240
<212> TYPE: PRT
<213> ORGANISM: Artificial sequence
<220> FEATURE:
<223> OTHER INFORMATION: Synthetic

<400> SEQUENCE: 13

Pro Val Gly Thr Pro Gly Thr Val Pro Gly Gly Val Val Pro Val Gly
1               5                   10                  15

Val Thr Pro Val Gly Gly Gly Thr Gly Thr Pro Thr Thr Val Thr Val
            20                  25                  30

Val Gly Gly Val Val Val Pro Gly Val Pro Gly Gly Thr Pro Gly
            35                  40                  45

Val Pro Val Gly Thr Pro Val Val Gly Val Gly Val Gly Thr Gly
    50                  55                  60

Thr Pro Gly Gly Thr Val Pro Gly Gly Thr Pro Gly Val Val Pro Gly
65                  70                  75                  80

Thr Pro Gly Gly Val Val Pro Gly Thr Thr Val Pro Thr Gly Thr Gly
                85                  90                  95

Thr Thr Pro Val Val Gly Val Pro Thr Val Gly Gly Val Thr Pro Gly
            100                 105                 110

Val Gly Gly Val Pro Val Val Val Gly Thr Gly Val Pro Gly Val Pro
```

```
            115                 120                 125
Val Gly Gly Gly Val Gly Val Gly Val Val Pro Gly Thr Val
        130                 135                 140
Pro Val Gly Val Pro Gly Val Gly Thr Val Pro Val Gly Thr
145                 150                 155                 160
Pro Thr Thr Gly Val Pro Gly Val Val Pro Thr Gly Val Thr Pro Gly
                165                 170                 175
Gly Val Gly Val Pro Gly Gly Val Val Gly Gly Val Pro Gly
            180                 185                 190
Val Thr Val Pro Val Gly Thr Val Thr Thr Gly Val Pro Val Val Thr
        195                 200                 205
Val Gly Val Val Val Pro Val Gly Thr Val Gly Gly Val Val Gly
        210                 215                 220
Gly Gly Thr Thr Pro Gly Gly Val Pro Gly Thr Pro Gly Val Gly Gly
225                 230                 235                 240

<210> SEQ ID NO 14
<211> LENGTH: 240
<212> TYPE: PRT
<213> ORGANISM: Artificial sequence
<220> FEATURE:
<223> OTHER INFORMATION: Synthetic

<400> SEQUENCE: 14

Gly Ala Val Val Val Pro Gly Gly Ala Val Gly Val Pro Ala Gly Ala
1               5                   10                  15
Val Gly Gly Val Gly Gly Val Leu Val Pro Ala Val Gly Ala Val Pro
            20                  25                  30
Gly Gly Gly Val Pro Ala Val Gly Val Pro Val Ala Gly Val Val Pro
        35                  40                  45
Gly Gly Leu Pro Gly Gly Ala Gly Val Gly Ala Leu Gly Ala Ala Ala
    50                  55                  60
Pro Gly Gly Val Pro Val Gly Ala Ala Leu Pro Gly Val Ala Gly Val
65                  70                  75                  80
Ala Pro Gly Gly Gly Leu Pro Gly Leu Gly Ala Gly Ala Gly Leu Gly
                85                  90                  95
Leu Ala Gly Ala Leu Val Leu Pro Gly Leu Gly Gly Val Pro Gly Val
            100                 105                 110
Pro Gly Gly Gly Leu Leu Pro Gly Gly Val Pro Leu Leu Gly Leu Pro
        115                 120                 125
Gly Val Pro Ala Gly Leu Pro Gly Val Leu Pro Val Gly Leu Leu Leu
    130                 135                 140
Pro Gly Ala Pro Gly Val Pro Ala Leu Gly Val Pro Leu Gly Val Pro
145                 150                 155                 160
Gly Val Ala Pro Gly Leu Pro Gly Ala Gly Gly Leu Pro Gly Val Gly
                165                 170                 175
Ala Pro Gly Leu Leu Pro Val Gly Gly Ala Pro Ala Ala Leu Gly Gly
            180                 185                 190
Leu Gly Leu Pro Gly Gly Gly Ala Leu Gly Leu Leu Ala Pro Gly Gly
        195                 200                 205
Ala Leu Val Pro Gly Val Gly Gly Val Ala Pro Val Ala Ala Gly Ala
    210                 215                 220
Leu Leu Pro Gly Gly Ala Pro Leu Gly Val Pro Ala Leu Leu Ala Leu
225                 230                 235                 240
```

<210> SEQ ID NO 15
<211> LENGTH: 240
<212> TYPE: PRT
<213> ORGANISM: Artificial sequence
<220> FEATURE:
<223> OTHER INFORMATION: Synthetic

<400> SEQUENCE: 15

```
Ser Gly Ser Ser Gly Ser Gly Phe Phe Ser Gly Val Pro Ser
1               5                   10                  15

Gly Gly Gly Val Val Phe Val Pro Ser Phe Phe Gly Phe Phe Pro Ser
                20                  25                  30

Gly Ser Gly Gly Val Val Pro Gly Val Pro Gly Gly Gly Val Gly Val
            35                  40                  45

Pro Gly Phe Val Gly Val Pro Val Gly Gly Phe Pro Val Gly Val Pro
    50                  55                  60

Gly Val Phe Val Pro Ser Val Val Gly Val Pro Gly Phe Phe Val Phe
65                  70                  75                  80

Pro Gly Val Pro Gly Gly Ser Ser Ser Pro Gly Ser Pro Phe Gly Val
                85                  90                  95

Phe Gly Gly Gly Ser Ser Gly Gly Phe Pro Phe Gly Ser Ser Pro
                100                 105                 110

Gly Val Val Val Ser Pro Gly Phe Gly Phe Gly Val Pro Phe Gly Val
            115                 120                 125

Pro Val Gly Gly Ser Val Phe Phe Pro Phe Gly Gly Phe Pro
    130                 135                 140

Gly Gly Phe Pro Ser Gly Ser Gly Phe Gly Val Pro Gly Gly Phe Val
145                 150                 155                 160

Val Pro Phe Gly Val Ser Pro Gly Ser Pro Gly Phe Val Pro Ser Phe
                165                 170                 175

Gly Ser Pro Gly Gly Phe Gly Gly Phe Ser Pro Phe Ser Ser Gly Val
            180                 185                 190

Gly Ser Pro Gly Gly Val Pro Gly Val Gly Val Val Ser Pro Gly Phe
            195                 200                 205

Pro Gly Gly Ser Pro Phe Gly Phe Pro Gly Ser Pro Gly Gly Ser Phe
    210                 215                 220

Gly Gly Ser Pro Ser Val Phe Gly Ser Gly Ser Pro Gly Ser Phe Pro
225                 230                 235                 240
```

<210> SEQ ID NO 16
<211> LENGTH: 240
<212> TYPE: PRT
<213> ORGANISM: Artificial sequence
<220> FEATURE:
<223> OTHER INFORMATION: Synthetic

<400> SEQUENCE: 16

```
Ala Ala Gly Gly Thr Gly Phe Phe Thr Gly Gly Ala Pro Gly Gly Thr
1               5                   10                  15

Pro Thr Ala Phe Gly Gly Phe Thr Pro Phe Thr Phe Ala Gly Gly Gly
                20                  25                  30

Ala Pro Gly Phe Phe Ala Phe Pro Gly Ala Pro Gly Thr Phe Pro Thr
            35                  40                  45

Phe Gly Ala Pro Gly Ala Ala Pro Gly Thr Thr Pro Gly Thr Phe
    50                  55                  60

Phe Gly Phe Pro Gly Gly Thr Pro Gly Thr Pro Gly Ala Ala Thr Pro
65                  70                  75                  80
```

Gly Phe Phe Gly Ala Phe Gly Phe Pro Gly Ala Phe Ala Thr Phe Gly
            85                  90                  95

Phe Pro Gly Gly Ala Gly Ala Ala Pro Ala Gly Thr Pro Gly Ala
        100                 105                 110

Pro Thr Ala Ala Gly Ala Thr Thr Pro Gly Ala Gly Gly Thr Thr Gly
        115                 120                 125

Gly Ala Pro Thr Gly Gly Phe Ala Pro Thr Phe Phe Gly Phe Phe
        130                 135                 140

Pro Thr Gly Thr Gly Gly Ala Ala Pro Gly Ala Pro Gly Gly Gly Thr
145                 150                 155                 160

Thr Thr Phe Pro Gly Ala Thr Pro Phe Gly Phe Pro Gly Thr Gly Thr
                    165                 170                 175

Pro Gly Thr Phe Gly Ala Pro Gly Gly Gly Phe Phe Pro Gly Ala Gly
                    180                 185                 190

Phe Gly Gly Ala Pro Gly Ala Pro Ala Ala Ala Gly Gly Gly Thr
            195                 200                 205

Pro Gly Thr Ala Thr Pro Gly Thr Phe Pro Thr Gly Ala Gly Thr Phe
            210                 215                 220

Pro Gly Thr Phe Pro Phe Gly Gly Phe Pro Gly Gly Phe Pro Thr
225                 230                 235                 240

<210> SEQ ID NO 17
<211> LENGTH: 240
<212> TYPE: PRT
<213> ORGANISM: Artificial sequence
<220> FEATURE:
<223> OTHER INFORMATION: Synthetic

<400> SEQUENCE: 17

Thr Ile Leu Pro Gly Ile Gly Leu Pro Gly Gly Leu Pro Leu Thr Ile
1               5                   10                  15

Gly Gly Ile Leu Pro Ile Leu Leu Gly Thr Thr Ile Gly Gly Ile Pro
                20                  25                  30

Gly Gly Gly Ile Ile Pro Gly Ile Gly Gly Ile Pro Ile Leu Thr
            35                  40                  45

Leu Leu Ile Leu Pro Thr Gly Leu Pro Gly Thr Pro Leu Thr Thr Gly
    50                  55                  60

Thr Pro Gly Ile Thr Gly Leu Gly Thr Pro Leu Gly Ile Gly Leu Ile
65                  70                  75                  80

Gly Thr Gly Ile Pro Gly Gly Gly Thr Gly Ile Pro Thr Gly Ile Pro
                85                  90                  95

Gly Thr Thr Leu Pro Gly Ile Pro Thr Leu Gly Gly Gly Ile Pro Leu
                100                 105                 110

Ile Gly Thr Pro Gly Gly Ile Gly Thr Ile Gly Ile Pro Gly Thr Gly
                115                 120                 125

Thr Ile Ile Gly Ile Pro Gly Gly Leu Leu Leu Ile Pro Gly Ile
        130                 135                 140

Thr Pro Leu Ile Gly Leu Pro Gly Gly Thr Pro Gly Thr Pro Gly Gly
145                 150                 155                 160

Gly Thr Gly Thr Thr Pro Thr Gly Leu Pro Gly Ile Leu Leu Pro Gly
                    165                 170                 175

Gly Leu Pro Gly Ile Pro Thr Gly Thr Pro Gly Thr Gly Thr Pro Ile
                    180                 185                 190

Gly Gly Leu Leu Ile Leu Leu Thr Leu Pro Gly Leu Pro Gly Leu Gly
            195                 200                 205

Leu Pro Gly Leu Ile Pro Leu Gly Thr Gly Leu Thr Gly Gly Thr Pro
210                 215                 220

Thr Gly Gly Ile Pro Gly Gly Ile Gly Ile Pro Gly Ile Leu Thr Thr
225                 230                 235                 240

<210> SEQ ID NO 18
<211> LENGTH: 240
<212> TYPE: PRT
<213> ORGANISM: Artificial sequence
<220> FEATURE:
<223> OTHER INFORMATION: Synthetic

<400> SEQUENCE: 18

Pro Gly Thr Tyr Pro Gly Tyr Gly Tyr Val Tyr Pro Thr Thr Gly Gly
1               5                   10                  15

Ile Pro Gly Gly Val Val Pro Gly Gly Thr Lys Leu Val Pro Gly
                20                  25                  30

Lys Gly Lys Gly Gly Ala Lys Ala Pro Gly Thr Val Pro Val Gly Ala
            35                  40                  45

Gly Gly Gly Lys Ile Val Pro Ile Tyr Gly Ile Ala Pro Gly Lys Tyr
        50                  55                  60

Gly Tyr Pro Gly Gly Gly Ile Val Pro Gly Ile Thr Thr Pro Gly Leu
65                  70                  75                  80

Pro Thr Gly Lys Lys Pro Tyr Gly Gly Val Pro Val Leu Tyr Gly Lys
                85                  90                  95

Leu Pro Gly Ala Pro Gly Ile Pro Thr Ala Gly Ala Pro Gly Tyr Ile
            100                 105                 110

Ala Pro Gly Val Pro Gly Gly Leu Val Lys Gly Thr Gly Ile Ala
        115                 120                 125

Pro Leu Gly Val Ile Leu Val Tyr Ile Gly Val Gly Gly Ile Lys Gly
    130                 135                 140

Gly Ala Leu Pro Thr Gly Gly Leu Tyr Pro Gly Ala Gly Thr Pro Gly
145                 150                 155                 160

Tyr Pro Val Gly Gly Gly Ala Pro Ala Gly Ile Ala Leu Lys Pro
                165                 170                 175

Gly Ile Thr Pro Gly Thr Ala Ala Pro Gly Leu Pro Gly Lys Gly Gly
            180                 185                 190

Lys Tyr Thr Tyr Pro Gly Gly Ala Pro Gly Gly Thr Gly Gly Val Pro
        195                 200                 205

Gly Tyr Pro Gly Leu Ala Leu Lys Leu Gly Ile Pro Thr Lys Gly Gly
    210                 215                 220

Gly Ile Gly Leu Pro Tyr Ile Gly Leu Leu Pro Gly Lys Pro Gly Gly
225                 230                 235                 240

<210> SEQ ID NO 19
<211> LENGTH: 6
<212> TYPE: PRT
<213> ORGANISM: Artificial sequence
<220> FEATURE:
<223> OTHER INFORMATION: Synthetic

<400> SEQUENCE: 19

Met Ser Lys Gly Pro Gly
1               5

<210> SEQ ID NO 20
<211> LENGTH: 3
<212> TYPE: PRT
<213> ORGANISM: Artificial sequence

```
<220> FEATURE:
<223> OTHER INFORMATION: Synthetic

<400> SEQUENCE: 20

Gly Trp Pro
1

<210> SEQ ID NO 21
<211> LENGTH: 15
<212> TYPE: PRT
<213> ORGANISM: Artificial sequence
<220> FEATURE:
<223> OTHER INFORMATION: Synthetic

<400> SEQUENCE: 21

Gly Gly Gly Gly Ser Gly Gly Gly Gly Ser Gly Gly Gly Gly Ser
1               5                   10                  15

<210> SEQ ID NO 22
<211> LENGTH: 19
<212> TYPE: PRT
<213> ORGANISM: Artificial sequence
<220> FEATURE:
<223> OTHER INFORMATION: Synthetic

<400> SEQUENCE: 22

Pro Gln Pro Gln Pro Lys Pro Gln Pro Lys Pro Glu Pro Glu Pro Gln
1               5                   10                  15

Pro Gln Gly

<210> SEQ ID NO 23
<211> LENGTH: 5
<212> TYPE: PRT
<213> ORGANISM: Artificial sequence
<220> FEATURE:
<223> OTHER INFORMATION: Synthetic
<220> FEATURE:
<221> NAME/KEY: Xaa
<222> LOCATION: (4)..(4)
<223> OTHER INFORMATION: any amino acid except proline

<400> SEQUENCE: 23

Val Pro Gly Xaa Gly
1               5
```

UNSTRUCTURED NON-REPETITIVE POLYPEPTIDES HAVING LCST BEHAVIOR

CROSS-REFERENCE TO RELATED APPLICATIONS

This application is a continuation of U.S. patent application Ser. No. 16/335,734, filed Mar. 22, 2019, which is the U.S. national stage entry, under 35 U.S.C. § 371, of International Application Number PCT/US2017/052887, filed Sep. 22, 2017, which claims priority to U.S. Provisional Application No. 62/399,123, filed Sep. 23, 2016, the entire contents of each of which are hereby incorporated by reference.

STATEMENT REGARDING FEDERALLY SPONSORED RESEARCH

This invention was made with government support under grant GM061232, awarded by the National Institutes of Health. The government has certain rights in the invention.

SEQUENCE LISTING

This instant application includes a Sequence Listing which has been submitted electronically in ASCII format and is hereby incorporated by reference in its entirety. Said ASCII copy created on Sep. 21, 2017, is named "028193-9228-WO01_As_Filed_Sequence_Listing.txt" and is 39986 bytes in size.

BACKGROUND

Proteins can be useful therapeutic agents when engineered for specificity, and selectivity for a clinical target. Their complexity, versatility, tolerability, and diversity often make them superior alternatives to small molecule drugs, and the long half-life, specificity, and selectivity can make them attractive for therapies. Although protein engineering allows for the development of potent therapeutics targeted toward a protein or receptor of interest, the body has many mechanisms with which to clear such protein therapies. Accordingly, there exists a need for reliable and broadly applicable protein delivery solutions.

SUMMARY

In one aspect, disclosed are unstructured polypeptides having no discernible repeat motif, wherein the polypeptide is soluble below the lower critical solution temperature (LCST), soluble above the upper critical solution temperature (UCST), or a combination thereof, wherein the LCST and UCST are each independently from about 0° C. to about 100° C.

In another aspect, disclosed are fusion proteins comprising at least one binding polypeptide and at least one of the disclosed unstructured polypeptides.

In another aspect, disclosed are methods for treating a disease in a subject in need thereof, the methods comprising administering to the subject an effective amount of a disclosed fusion protein.

In another aspect, disclosed are methods of diagnosing a disease in a subject, the methods comprising contacting a sample from the subject with a disclosed fusion protein; and detecting binding of the fusion protein to a target to determine presence of the target in the sample, wherein the presence of the target in the sample indicates the disease in the subject.

In another aspect, disclosed are methods of determining the presence of a target in a sample, the methods comprising contacting the sample with a disclosed fusion protein under conditions to allow a complex to form between the fusion protein and the target in the sample; and detecting the presence of the complex, wherein presence of the complex is indicative of the target in the sample.

In another aspect, disclosed are methods of determining the effectiveness of a treatment for a disease in a subject in need thereof, the methods comprising contacting a sample from the subject with a disclosed fusion protein under conditions to allow a complex to form between the fusion protein and a target in the sample; determining the level of the complex in the sample, wherein the level of the complex is indicative of the level of the target in the sample; and comparing the level of the target in the sample to a control level of the target, wherein if the level of the target is different from the control level, then the treatment is determined to be effective or ineffective in treating the disease.

In another aspect, disclosed are methods of diagnosing a disease in a subject, the methods comprising contacting a sample from the subject with a disclosed fusion protein; determining the level of a target in the sample; and comparing the level of the target in the sample to a control level of the target, wherein a level of the target different from the control level indicates disease in the subject.

BRIEF DESCRIPTION OF THE DRAWINGS

FIG. 3(A) is a graph showing repetitive and exemplary non-repetitive polypeptides comprising 200 amino acids. FIG. 3(B) is a graph showing repetitive and exemplary non-repetitive polypeptides comprising 400 amino acids.

FIG. 4(A) is a graph showing transition temperature characterization of exemplary non-repetitive unstructured polypeptides at 25 μM in PBS. FIG. 4(B) is a graph showing transition temperature characterization of exemplary non-repetitive unstructured polypeptides in PBS at various concentrations of urea.

DETAILED DESCRIPTION

Figure 1:
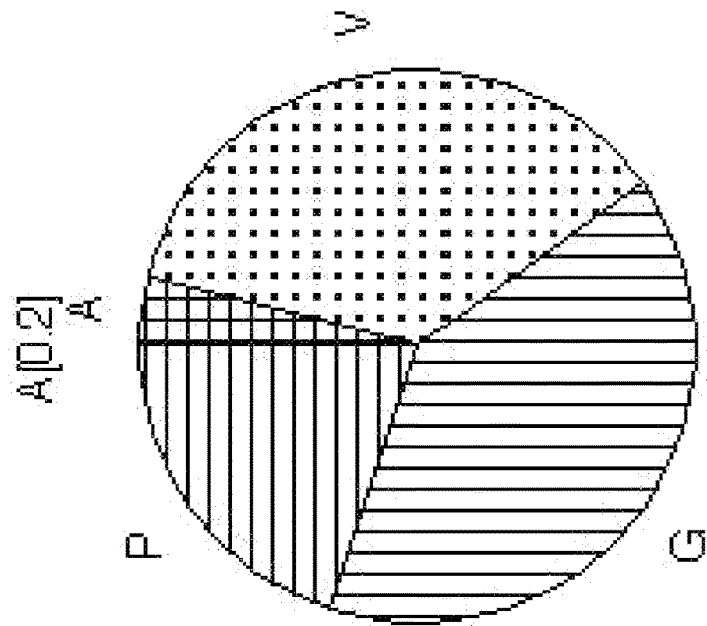
FIG. 1 is a diagram showing the amino acid compositions of the A[0.5] and A[0.2] sequences (SEQ ID NO: 1 and SEQ ID NO: 2). Correspondingly, the diagram also shows the amino acid compositions of polypeptides of SEQ ID NOs: 4, 6, 8, and 10 and SEQ ID NOs: 3, 5, 7, and 9, respectively.
Figure 1:
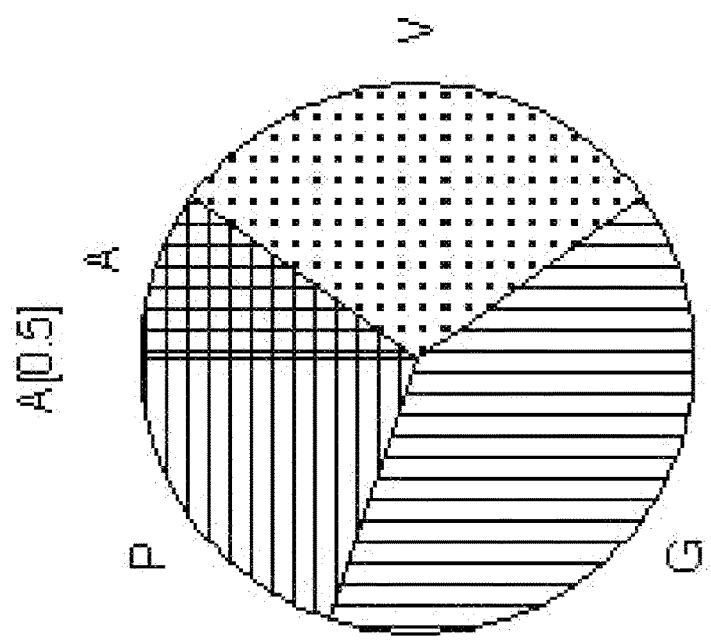

Elastin-like polypeptides (ELPs) are repetitive polypeptides. "ELP" refers to a polypeptide comprising the pentapeptide repeat sequence (VPGXG)$_n$, wherein X is any amino acid except proline and n is an integer greater than or equal to 1 (SEQ ID NO: 23). ELPs have been examined and characterized as having lower critical solution temperature (LCST) behavior. ELPs may include, for example, repeating subsequences of GAGVPGVGVP (SEQ ID NO: 1) or GVGVPGVGVPGAGVPGVGVPGVGVP (SEQ ID NO: 2), herein referred to as A[0.5] and A[0.2] respectively (see McDaniel, J. R et al. (2013) *Biomacromolecules*, which is incorporated by reference herein in its entirety). For example, A[0.2] rep-200 (SEQ ID NO: 3, (GVGVPGVGVPGAGVPGVGVPGVGVP)$_8$) includes the A[0.2] subsequence repeated 8 times for a total of 200 amino acids. A[0.5] rep-200 (SEQ ID NO: 4, (GAGVPGVGVP)$_{20}$) includes the A[0.5] subsequence repeated 20 times for a total of 200 amino acids. A[0.2] rep-400 (SEQ ID NO: 5, (GVGVPGVGVPGAGVPGVGVPGVGVP)$_{15}$) includes the A[0.2] subsequence repeated 16 times for a total of 400 amino acids. A[0.5] rep-400 (SEQ ID NO: 6, (GAGVPGVGVP)$_{40}$) includes the A[0.5] subsequence repeated 40 times for a total of 400 amino acids. The amino acid compositions of these sequences are depicted in FIG. 1.

Disclosed herein are unstructured, non-repetitive polypeptides that lack the requisite pentapeptide sequence of ELPs, yet unexpectedly still have LCST behavior. Accordingly, the disclosed unstructured polypeptides lack secondary structure (according to CD) and are thermally responsive, all without having a discernable repetitive sequence within the polypeptide.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

As used herein, the term "affinity" refers to the binding strength of a binding polypeptide to its target (i.e., binding partner).

As used herein, the term "agonist" refers to an entity that binds to a receptor and activates the receptor to produce a biological response. An "antagonist" blocks or inhibits the action or signaling of the agonist. An "inverse agonist" causes an action opposite to that of the agonist. The activities of agonists, antagonists, and inverse agonists may be determined in vitro, in situ, in vivo, or a combination thereof.

As used herein, the term "biomarker" refers to a naturally occurring biological molecule present in a subject at varying concentrations that is useful in identifying and/or classifying a disease or a condition. The biomarker can include genes, proteins, polynucleotides, nucleic acids, ribonucleic acids, polypeptides, or other biological molecules used as an indicator or marker for disease. In some embodiments, the biomarker comprises a disease marker. For example, the biomarker can be a gene that is upregulated or downregulated in a subject that has a disease. As another example, the biomarker can be a polypeptide whose level is increased or decreased in a subject that has a disease or risk of developing a disease. In some embodiments, the biomarker comprises a small molecule. In some embodiments, the biomarker comprises a polypeptide.

As used herein, the terms "control," "reference level," and "reference" are used interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, TX; SAS Institute Inc., Cary, NC.). The healthy or normal levels or ranges for a target or for a protein activity may be defined in accordance with standard practice.

As used herein, the term "expression vector" indicates a plasmid, a virus or another medium, known in the art, into which a nucleic acid sequence for encoding a desired protein can be inserted or introduced.

As used herein, the term "host cell" is a cell that is susceptible to transformation, transfection, transduction, conjugation, and the like with a nucleic acid construct or expression vector. Host cells can be derived from plants, bacteria, yeast, fungi, insects, animals, etc. In some embodiments, the host cell includes *Escherichia coli*.

As used herein, the term "reporter," "reporter group," "label," and "detectable label" are used interchangeably herein. The reporter is capable of generating a detectable signal. The label can produce a signal that is detectable by visual or instrumental means. A variety of reporter groups can be used, differing in the physical nature of signal transduction (e.g., fluorescence, electrochemical, nuclear magnetic resonance (NMR), and electron paramagnetic resonance (EPR)) and in the chemical nature of the reporter group. Various reporters include signal-producing substances, such as chromagens, fluorescent compounds, chemiluminescent compounds, radioactive compounds, and the like. In some embodiments, the reporter comprises a radiolabel. Reporters may include moieties that produce light, e.g., acridinium compounds, and moieties that produce fluorescence, e.g., fluorescein. In some embodiments, the signal from the reporter is a fluorescent signal. The reporter may comprise a fluorophore. Examples of fluorophores include, but are not limited to, acrylodan (6-acryloyl-2-dimethylaminonaphthalene), badan (6-bromo-acetyl-2-dimethylamino-naphthalene), rhodamine, naphthalene, danzyl aziridine, 4-[N-[(2-iodoacetoxy)ethyl]-N-methylamino]-7-nitrobenz-2-oxa-1,3-diazole ester (IANBDE), 4-[N-[(2-iodoacetoxy)ethyl]-N-methylamino-7-nitrobenz-2-oxa-1,3-diazole (IANBDA), fluorescein, dipyrromethene boron difluoride (BODIPY), 4-nitrobenzo[c][1,2,5]oxadiazole (NBD), Alexa fluorescent dyes, and derivatives thereof. Fluorescein derivatives may include, for example, 5-fluorescein, 6-carboxyfluorescein, 3'6-carboxyfluorescein, 5(6)-carboxyfluorescein, 6-hexachlorofluorescein, 6-tetrachlorofluorescein, fluorescein, and isothiocyanate.

As used herein, the term "sample" or "test sample" can mean any sample in which the presence and/or level of a target is to be detected or determined. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

As used herein, the term "subject" as used herein can mean a mammal that wants or is in need of the herein described fusion proteins. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant.

As used herein, the term "transition" or "phase transition" refers to the aggregation of thermally responsive polypeptides. Phase transition occurs sharply and reversibly at a specific temperature called the LCST or the inverse transition temperature $T_t$. Below the transition temperature (LCST or $T_t$), a thermally responsive polypeptide is highly soluble. Upon heating above the transition temperature, a thermally responsive polypeptide may hydrophobically collapse and aggregate, forming a separate, gel-like phase. Phase transition behavior may be used to form drug depots within a tissue of a subject for controlled and/or slow release of the polypeptide. "Inverse transition cycling" refers to a protein purification method for thermally responsive polypeptides. The protein purification method may involve the use of thermally responsive polypeptide's reversible phase transition behavior to cycle the solution through soluble and insoluble phases, thereby removing contaminants and eliminating the need for chromatography.

As used herein, the term "subsequence" refers to a sequence of contiguous amino acids that occurs within another sequence of contiguous amino acids. A subsequence includes at least two amino acids. In some embodiments, a subsequence is 2 to 50, 2 to 20, 2 to 15, or 2 to 10 sequential amino acids in length. In some embodiments, a subsequence includes 3, 4, 5, 6, 7, 8, 9, or 10 sequential amino acids.

As used herein, the term "substantially identical" can mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, or 1100 amino acids.

As used herein, the term "treatment" or "treating," when referring to protection of a subject from a disease, means preventing, suppressing, repressing, ameliorating, or completely eliminating the disease. Preventing the disease involves administering a composition of the present invention to a subject prior to onset of the disease. Suppressing the disease involves administering a composition of the present disclosure to a subject after induction of the disease but before its clinical appearance. Repressing or ameliorating the disease involves administering a composition of the present disclosure to a subject after clinical appearance of the disease.

As used herein, the term "valency" refers to the potential binding units or binding sites. The term "multivalent" refers to multiple potential binding units. The terms "multimeric" and "multivalent" are used interchangeably herein.

As used herein, the term "variant" with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequences substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of 2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

2. Unstructured Polypeptides

Disclosed herein are unstructured polypeptides. The unstructured polypeptide may comprise any suitable polypeptide lacking secondary structure as observed by CD, and which lacks any discernable repetitive sequences. In addition, the unstructured polypeptide may be soluble below its LCST and/or above its UCST at a given concentration, thereby conferring a phase transition characteristic to the polypeptide such that it may be referred to as a "thermally responsive polypeptide." LCST is the temperature below which the polypeptide is miscible. UCST is the temperature above which the polypeptide is miscible. The LCST is a separate and distinct temperature relative to the UCST. In some embodiments, the unstructured polypeptide may have only UCST behavior. In some embodiments, the unstructured polypeptide may have only LCST behavior. In some embodiments, the unstructured polypeptide may have both UCST and LCST behavior. In such embodiments, the UCST is higher than the LCST. The unstructured polypeptide may have a LCST of about 0° C. to about 100° C., such as about 10° C. to about 50° C., or about 20° C. to about 42° C. The unstructured polypeptide may have a UCST of about 0° C. to about 100° C., such as about 10° C. to about 50° C., or about 20° C. to about 42° C. In some embodiments, the unstructured polypeptide may have a transition temperature(s) (LCST and/or UCST) between room temperature (about 25° C.) and body temperature (about 37° C.). The unstructured polypeptide may have its LCST and/or UCST below body temperature or above body temperature at the concentration at which the unstructured polypeptide is administered to a subject. Thermally responsive unstructured polypeptides can phase transition at varying temperatures and concentrations. Thermally responsive unstructured polypeptides may not affect the binding or potency of a second polypeptide to which it is conjugated. In addition, thermally responsive unstructured polypeptides may be tuned to any number of desired transition temperatures, molecular weights, and formats.

The unstructured polypeptide may include varying amounts and types of amino acids. For example, the unstructured polypeptide may include a sequence of at least 50 amino acids, wherein at least 10% of the amino acids are proline (P), and at least 20% of the amino acids are glycine (G). In some embodiments, the unstructured polypeptide may include a sequence wherein at least 40% of the amino acids are selected from the group consisting of valine (V), alanine (A), leucine (L), lysine (K), threonine (T), isoleucine (I), tyrosine (Y), serine (S), and phenylalanine (F). In some embodiments, the unstructured polypeptide may include a sequence that does not contain three contiguous identical amino acids, wherein any 5-10 amino acid subsequence does not occur more than once in the unstructured polypeptide, and wherein when the unstructured polypeptide comprises a subsequence starting and ending with proline (P), the subsequence further includes at least one glycine (G).

In some embodiments, the unstructured polypeptide may include a sequence of at least 50 amino acids, wherein at least 10% of the amino acids are proline (P); wherein at least 20% of the amino acids are glycine (G); wherein at least 40% of the amino acids are selected from the group consisting of valine (V), alanine (A), leucine (L), lysine (K), threonine (T), isoleucine (I), tyrosine (Y), serine (S), and phenylalanine (F); wherein the sequence does not contain three contiguous identical amino acids; wherein any 5-10 amino acid subsequence does not occur more than once in the unstructured polypeptide; and wherein when the unstructured polypeptide comprises a subsequence starting and ending with proline (P), the subsequence further comprising at least one glycine (G).

Shorter subsequences of any of the non-repetitive sequences identified by the computer algorithm (as discussed below in the Examples) can maintain thermo-responsive behavior. Unstructured polypeptides comprising subsequences as short as 50 amino acids can satisfy the requirements of the algorithm, with similar composition as the full length sequence being sufficiently non-repetitive, because they are constrained by the same aforementioned sequence rules. Previous work has shown that intrinsic disorder can be encoded by unstructured peptides of less than 50 amino acids in length (see Radivojac et al. (2007) Biophys J., which is incorporated by reference herein in its entirety). Furthermore, ELPs as short as 50 amino acids can exhibit thermo-responsive LCST behavior, with measured transition temperatures within the range of 0 to 100° C. (see Aladini et al. (2016) J Pept Sci., which is incorporated by reference herein in its entirety). Accordingly in some embodiments, the unstructured polypeptide may comprise a 50 amino acid subsequence of any of SEQ ID NO: 7-18.

As mentioned above, the unstructured polypeptide may lack any discernable repeat motif of amino acids. The repetitiveness of the unstructured polypeptides may be characterized by its linguistic complexity score. Linguistic complexity score is defined by the total number of unique subsequences in a given sequence divided by the total number of unique subsequences possible for the same alphabet and window length (see Troyanskaya et al. (2002) Bioinformatics, which is incorporated by reference herein in its entirety). Further detail of linguistic complexity score can be found in Example 1 below. The unstructured polypeptide may have a linguistic complexity score of greater than 15, greater than 16, greater than 17, greater than 18, greater than 19, or greater than 20.

In some embodiments, the unstructured polypeptide may comprise an amino acid sequence selected from the group consisting of SEQ ID Nos. 7-18.

3. Fusion Proteins

Also disclosed herein are fusion proteins that can include at least one of the unstructured polypeptides, as described above. The fusion protein may further include at least one binding polypeptide and at least one linker.

In some embodiments, the fusion protein may include more than one binding polypeptide. The fusion protein may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 binding polypeptides. The fusion protein may include less than 30, less than 25, or less than 20 binding polypeptides. The fusion protein may include 1 to 30, such as 1 to 20, or 1 to 10 binding polypeptides. In such embodiments, the binding polypeptides may be the same or different from one another. In some embodiments, the fusion protein may include more than one binding polypeptide positioned in tandem to one another. In some embodiments, the fusion protein may include 2 to 6 binding polypeptides. For example, the fusion protein may include two binding polypeptides, three binding polypeptides, four binding polypeptides, five binding polypeptides, or six binding polypeptides.

In some embodiments, the fusion protein may include more than one unstructured polypeptide. The fusion protein may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 unstructured polypeptides. The fusion protein may include less than 30, less than 25, or less than 20 unstructured polypeptides. The fusion protein may include 1 to 30, such as 1 to 20, or 1 to 10 unstructured polypeptides. In such embodiments, the unstructured polypeptides may be the same or different from one another. In some embodiments, the fusion protein may include more than one unstructured polypeptide positioned in tandem to one another.

In some embodiments, the fusion protein may be arranged as a modular linear polypeptide. For example, the modular linear polypeptide may be arranged in one of the following structures: [binding polypeptide]$_m$-[linker]$_k$-[unstructured polypeptide]; [unstructured polypeptide]-[linker]$_k$-[binding polypeptide]$_m$; [binding polypeptide]$_m$-[linker]$_k$-[unstructured polypeptide]-[binding polypeptide]$_m$-[linker]$_k$-[unstructured polypeptide]; or [unstructured polypeptide]-[binding polypeptide]$_m$-[linker]$_k$-[unstructured polypeptide]-[binding polypeptide]$_m$, in which k and m are each independently an integer greater than or equal to 1. In some embodiments, m may be an integer less than or equal to 20. In some embodiments, m may be an integer equal to 1, 2, 3, 4, 5, 6, 7, 8, 9, 10, 11, 12, 13, 14, 15, 16, 17, 18, 19, or 20. In some embodiments, k may be an integer less than or equal to 10. In some embodiments, k may be an integer equal to 1, 2, 3, 4, 5, 6, 7, 8, 9, or 10. In some embodiments, the at least one binding polypeptide may be positioned N-terminal to the at least one unstructured polypeptide. In some embodiments, the at least one binding polypeptide may be positioned C-terminal to the at least one unstructured polypeptide.

In some embodiments, a fusion protein comprising one or more thermally responsive polypeptides may have a transition temperature between room temperature (about 25° C.) and body temperature (about 37° C.). The thermally responsive, unstructured polypeptide may have its LCST or UCST below body temperature or above body temperature at the concentration at which the fusion protein is administered to a subject.

The fusion protein may be expressed recombinantly in a host cell according to methods known within the art. The fusion protein may be purified by any suitable means known within the art. For example, the fusion protein may be purified using chromatography, such as liquid chromatography, size exclusion chromatography, or affinity chromatography, or through ultracentrifugation techniques. In some embodiments, the fusion protein may be purified without chromatography. In some embodiments, the fusion protein may be purified using inverse transition cycling.

a. Binding Polypeptide

The binding polypeptide may comprise any polypeptide that is capable of binding at least one target. The binding polypeptide may bind at least one target. "Target" may be an entity capable of being bound by the binding polypeptide. Targets may include, for example, another polypeptide, a cell surface receptor, a carbohydrate, an antibody, a small molecule, or a combination thereof. The target may be a biomarker. The target may be activated through agonism or blocked through antagonism. The binding polypeptide may specifically bind the target. By binding a target, the binding polypeptide may act as a targeting moiety, an agonist, an antagonist, or a combination thereof.

The binding polypeptide may be a monomer that binds to a target. The monomer may bind one or more targets. The binding polypeptide may form an oligomer. The binding polypeptide may form an oligomer with the same or different binding polypeptides. The oligomer may bind to a target. The oligomer may bind one or more targets. One or more monomers within an oligomer may bind one or more targets. In some embodiments, the fusion protein may be multivalent. In some embodiments, the fusion protein may bind multiple targets. In some embodiments, the activity of the binding polypeptide alone may be the same as the activity of the binding protein when part of a fusion protein.

In some embodiments, the binding polypeptide may comprise one or more scaffold proteins. As used herein, "scaffold protein" refers to one or more polypeptide domains with relatively stable and defined three-dimensional structures. Scaffold proteins may further have the capacity for affinity engineering. In some embodiments, the scaffold protein may be engineered to bind a particular target. In embodiments where the binding polypeptide comprises more than 1 scaffold protein, the scaffold proteins may be the same or different.

In some embodiments, the binding polypeptide may comprise Protein A. Protein A is a 42 kD protein originally derived from *Staphylococcus aureus*. It can exhibit high binding affinity to the constant region (Fc) of immunoglobulin G antibodies. Protein A includes 5 linked domains that are all able to bind antibody Fc. Immobilized protein A can be used for the purification of a variety of antibodies (see, e.g., Hober et al. (2006) J. Chromatogr. B, which is incorporated by reference herein in its entirety).

b. Linker

As mentioned above, the fusion protein may further include at least one linker. In some embodiments, the fusion protein may include more than one linker. In such embodiments, the linkers may be the same or different from one another. The fusion protein may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 55, at least 60, at least 65, at least 70, at least 75, at least 80, at least 85, at least 90, at least 95, or at least 100 linkers. The fusion protein may include less than 500, less than 400, less than 300, or less than 200 linkers. The fusion protein may include 1 to 1000 linkers, such as 10 to 900, 10 to 800, or 5 to 500 linkers.

The linker may be positioned in between a binding polypeptide and an unstructured polypeptide, in between binding polypeptides, in between unstructured polypeptides, or a combination thereof. Multiple linkers may be positioned adjacent to one another. Multiple linkers may be positioned adjacent to one another and in between the binding polypeptide and the unstructured polypeptide.

The linker may be a polypeptide of any suitable amino acid sequence and length. The linker may act as a spacer peptide. The linker may occur between polypeptide domains. The linker may sufficiently separate the binding domains of the binding polypeptide while preserving the activity of the binding domains. In some embodiments, the linker may comprise charged amino acids. In some embodiments, the linker may be flexible. In some embodiments, the linker may comprise at least one glycine and at least one serine. In some embodiments, the linker may comprise an amino acid sequence consisting of $(Gly_4Ser)_3$ (SEQ ID NO: 21). In some embodiments, the linker may comprise at least one proline. In some embodiments, the linker may comprise an amino acid sequence consisting of SEQ ID NO:22.

c. Polynucleotides

Further disclosed are polynucleotides encoding the fusion proteins detailed herein. A vector may include the polynucleotide encoding the fusion proteins detailed herein. To obtain expression of a polypeptide, one typically subclones the polynucleotide encoding the polypeptide into an expression vector that contains a promoter to direct transcription, a transcription/translation terminator, and if for a nucleic acid encoding a protein, a ribosome binding site for translational initiation. An example of a vector is pet24. Suitable bacterial promoters are well known in the art. Further disclosed is a host cell transformed or transfected with an expression vector comprising a polynucleotide encoding a fusion protein as detailed herein. Bacterial expression systems for expressing the protein are available in, e.g., *E. coli, Bacillus* sp., and *Salmonella* (Paiva et al., Gene 1983, 22, 229-235; Mosbach et al., Nature 1983, 302, 543-545, which are both incorporated by reference herein in their entirety). Kits for such expression systems are commercially available. Eukaryotic expression systems for mammalian cells, yeast, and insect cells are well known in the art and are also commercially available. Retroviral expression systems may also be used.

4. Administration

The fusion proteins as detailed above can be formulated in accordance with standard techniques known to those skilled in the pharmaceutical art. Such compositions comprising a fusion protein can be administered in dosages and by techniques known to those skilled in the medical arts taking into consideration such factors as the age, sex, weight, and condition of the particular subject, and the route of administration.

The fusion protein can be administered prophylactically or therapeutically. In prophylactic administration, the fusion protein can be administered in an amount sufficient to induce a response. In therapeutic applications, the fusion proteins can be administered to a subject in need thereof in an amount sufficient to elicit a therapeutic effect. An amount adequate to accomplish this is defined as "therapeutically effective dose." Amounts effective for this use will depend on, e.g., the particular composition of the fusion protein regimen administered, the manner of administration, the stage and severity of the disease, the general state of health of the patient, and the judgment of the prescribing physician.

The fusion protein can be administered by methods known in the art as described in Donnelly et al. (*Ann. Rev. Immunol.* 1997, 15, 617-648); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The fusion protein can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The fusion proteins can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the fusion protein can be administered intravenously, intraarterially, or intraperitoneally to the subject.

The fusion protein can be a liquid preparation such as a suspension, syrup, or elixir. The fusion protein can be incorporated into liposomes, microspheres, or other polymer matrices (such as by a method described in Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The fusion protein may be used as a vaccine. The vaccine can be administered via electroporation, such as by a method described in U.S. Pat. No. 7,664,545, the contents of which are incorporated herein by reference in its entirety. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation can be carried out via a minimally invasive device.

In some embodiments, the fusion protein can be administered in a controlled release formulation. In some embodiments, the fusion protein may comprise one or more thermally responsive polypeptides, the thermally responsive polypeptide having a transition temperature such that the fusion protein remains soluble prior to administration and such that the fusion protein transitions upon administration to a gel-like depot in the subject. In some embodiments, the fusion protein may comprise one or more thermally responsive polypeptides, the thermally responsive polypeptide having a transition temperature such that the fusion protein remains soluble at room temperature and such that the fusion protein transitions upon administration to a gel-like depot in the subject. For example, in some embodiments, the fusion protein may comprise one or more thermally responsive polypeptides, the thermally responsive polypeptide having a transition temperature between room temperature (about 25° C.) and body temperature (about 37° C.), whereby the fusion protein can be administered to form a depot. As used herein, "depot" refers to a gel-like composition comprising a fusion protein that releases the fusion protein over time. In some embodiments, the fusion protein can be injected subcutaneously or intratumorally to form a depot (coacervate). The depot may provide controlled and/or slow release of the fusion protein. The depot may provide slow release of the fusion protein into the circulation or the tumor, for example. In some embodiments, the fusion protein may be released from the depot over a period of at least 1 day, at least 2 days, at least 3 days, at least 4 days, at least 5 days, at least 6 days, at least 7 days, at least 1 week, at least 1.5 weeks, at least 2 weeks, at least 2.5 weeks, at least 3.5 weeks, at least 4 weeks, or at least 1 month.

5. Detection

As used herein, the term "detect" or "determine the presence of" refers to the qualitative measurement of undetectable, low, normal, or high concentrations of one or more fusion proteins, targets, or fusion proteins bound to target. Detection may include in vitro, ex vivo, or in vivo detection. Detection may include detecting the presence of one or more fusion proteins or targets versus the absence of the one or more fusion proteins or targets. Detection may also include quantification of the level of one or more fusion proteins or targets. The term "quantify" or "quantification" may be used interchangeably, and may refer to a process of determining the quantity or abundance of a substance (e.g., fusion protein or target), whether relative or absolute. Any suitable method of detection falls within the general scope of the present disclosure. In some embodiments, the fusion protein may comprise a reporter attached thereto for detection. In some embodiments, the fusion protein may be labeled with a reporter. In some embodiments, detection of fusion protein bound to target may be determined by methods including but not limited to, band intensity on a Western blot, flow cytometry, radiolabel imaging, cell binding assays, activity assays, surface plasmon resonance (SPR), immunoassay, or by various other methods known in the art.

In some embodiments, including those wherein the fusion protein is an antibody mimic for binding and/or detecting a target, any immunoassay may be utilized. The immunoassay may be an enzyme-linked immunoassay (ELISA), radioimmunoassay (RIA), a competitive inhibition assay, such as forward or reverse competitive inhibition assays, a fluorescence polarization assay, or a competitive binding assay, for example. The ELISA may be a sandwich ELISA. Specific immunological binding of the fusion protein to the target can be detected via direct labels, attached to the fusion protein or via indirect labels, such as alkaline phosphatase or horseradish peroxidase. The use of immobilized fusion proteins may be incorporated into the immunoassay. The fusion proteins may be immobilized onto a variety of supports, such as magnetic or chromatographic matrix particles, the surface of an assay plate (such as microtiter wells), pieces of a solid substrate material, and the like. An assay strip can be prepared by coating the fusion protein or plurality of fusion proteins in an array on a solid support. This strip can then be dipped into the test biological sample and then processed quickly through washes and detection steps to generate a measurable signal, such as a colored spot.

6. Methods a. Methods of Treating a Disease

In another aspect, disclosed are methods of treating a disease in a subject in need thereof. The method may comprise administering to the subject an effective amount of the fusion protein as described herein. The disease may be selected from cancer, metabolic disease, autoimmune disease, cardiovascular disease, and orthopedic disorders. In some embodiments, the disease may be a disease associated with a target of the at least one binding polypeptide.

Metabolic disease may occur when abnormal chemical reactions in the body alter the normal metabolic process. Metabolic diseases may include, for example, insulin resistance, non-alcoholic fatty liver diseases, type 2 diabetes, insulin resistance diseases, cardiovascular diseases, arteriosclerosis, lipid-related metabolic disorders, hyperglycemia, hyperinsulinemia, hyperlipidemia, and glucose metabolic disorders.

Autoimmune diseases may arise from an abnormal immune response of the body against substances and tissues normally present in the body. Autoimmune diseases may include, but are not limited to, lupus, rheumatoid arthritis, multiple sclerosis, insulin dependent diabetes mellitis, myasthenia gravis, Grave's disease, autoimmune hemolytic anemia, autoimmune thrombocytopenia purpura, Goodpasture's syndrome, pemphigus vulgaris, acute rheumatic fever, post-streptococcal glomerulonephritis, polyarteritis *nodosa*, myocarditis, psoriasis, Celiac disease, Crohn's disease, ulcerative colitis, and fibromyalgia.

Cardiovascular disease is a class of diseases that involve the heart or blood vessels. Cardiovascular diseases may include, for example, coronary artery diseases (CAD) such as angina and myocardial infarction (heart attack), stroke, hypertensive heart disease, rheumatic heart disease, cardiomyopathy, heart arrhythmia, congenital heart disease, valvular heart disease, carditis, aortic aneurysms, peripheral artery disease, and venous thrombosis.

Orthopedic disorders or musculoskeletal disorders are injuries or pain in the body's joints, ligaments, muscles, nerves, tendons, and structures that support limbs, neck, and back. Orthopedic disorders may include degenerative diseases and inflammatory conditions that cause pain and impair normal activities. Orthopedic disorders may include, for example, carpal tunnel syndrome, epicondylitis, and tendinitis.

Cancers may include, but are not limited to, breast cancer, colorectal cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancers, carcinomas, sarcomas, and soft tissue cancers. In some embodiments, the cancer may be colorectal cancer. In some embodiments, the cancer may be colorectal adenocarcinoma.

In some embodiments, the present disclosure provides a method for using scaffold proteins in developing antibody mimetics for oncological targets of interest. With the emergence of scaffold protein engineering come the possibilities for designing potent protein drugs that are unhindered by steric and architectural limitations. Although potent protein drugs can be useful for diagnostics or treatments, successful delivery to the target region can pose a great challenge.

b. Methods of Diagnosing a Disease

In another aspect, disclosed are methods of diagnosing a disease. The methods may include administering to the subject a fusion protein as described herein, and detecting binding of the fusion protein to a target to determine presence of the target in the subject. The presence of the target may indicate the disease in the subject. In some embodiments, the methods may include contacting a sample from the subject with a fusion protein as described herein, determining the level of a target in the sample, and comparing the level of the target in the sample to a control level of the target, wherein a level of the target different from the control level indicates disease in the subject. In some embodiments, the disease may be selected from cancer, metabolic disease, autoimmune disease, cardiovascular disease, and orthopedic disorders, as detailed above. In some embodiments, the target may comprise a disease marker or biomarker. In some embodiments, the fusion protein may act as an antibody mimic for binding and/or detecting a target.

c. Methods of Determining the Presence of a Target

In another aspect, disclosed are methods of determining the presence of a target in a sample. The methods may include contacting the sample with a fusion protein as described herein under conditions to allow a complex to form between the fusion protein and the target in the sample, and detecting the presence of the complex. Presence of the complex may be indicative of the target in the sample. In some embodiments, the fusion protein may be labeled with a reporter for detection.

In some embodiments, the sample may be obtained from a subject and the method may further include diagnosing, prognosticating, or assessing the efficacy of a treatment of the subject. When the method includes assessing the efficacy of a treatment of the subject, then the method may further include modifying the treatment of the subject as needed to improve efficacy.

d. Methods of Determining the Effectiveness of a Treatment

In another aspect, disclosed are methods of determining the effectiveness of a treatment for a disease in a subject in need thereof. The methods may include contacting a sample from the subject with a fusion protein as detailed herein under conditions to allow a complex to form between the fusion protein and a target in the sample, determining the level of the complex in the sample, wherein the level of the complex is indicative of the level of the target in the sample, and comparing the level of the target in the sample to a control level of the target, wherein if the level of the target is different from the control level, then the treatment is determined to be effective or ineffective in treating the disease.

Time points may include prior to onset of disease, prior to administration of a therapy, various time points during administration of a therapy, after a therapy has concluded, or a combination thereof. Upon administration of the fusion protein to the subject, the fusion protein may bind a target, wherein the presence of the target indicates the presence of the disease in the subject at the various time points. In some embodiments, the target may comprise a disease marker or biomarker. In some embodiments, the fusion protein may act as an antibody mimic for binding and/or detecting a target. Comparison of the binding of the fusion protein to the target at various time points may indicate whether the disease has progressed, whether the diseased has advanced, whether a therapy is working to treat or prevent the disease, or a combination thereof.

In some embodiments, the control level may correspond to the level in the subject at a time point before or during the period when the subject has begun treatment, and the sample is taken from the subject at a later time point. In some embodiments, the sample may be taken from the subject at a time point during the period when the subject is undergoing treatment, and the control level corresponds to a disease-free level or to the level at a time point before the period when the subject has begun treatment. In some embodiments, the method may further include modifying the treatment or administering a different treatment to the subject when the treatment is determined to be ineffective in treating the disease.

7. Examples

Example 1: Identification of Non-Repetitive Unstructured Polypeptides

Non-repetitive permutated versions of ELPs were produced and examined. A computer algorithm was used to identify sequences comprising 200 or 400 amino acids, each with the same amino acid composition as the ELP counterpart, but with permutated or re-arranged ordering of the amino acids. The generated sequences were sufficiently non-repetitive, as they were rejected if they contained at least one subsequence comprising 5 to 10 amino acids that (a) contained three contiguous identical amino acids, (b) occurred more than once within the sequence, or (c) contained at least 2 prolines (P) separated by zero or more amino acids that are not glycine (G). These constraints promoted well-distributed prolines (P) and glycines (G) which have together been identified as structure-breaking residues.

Figure 2:
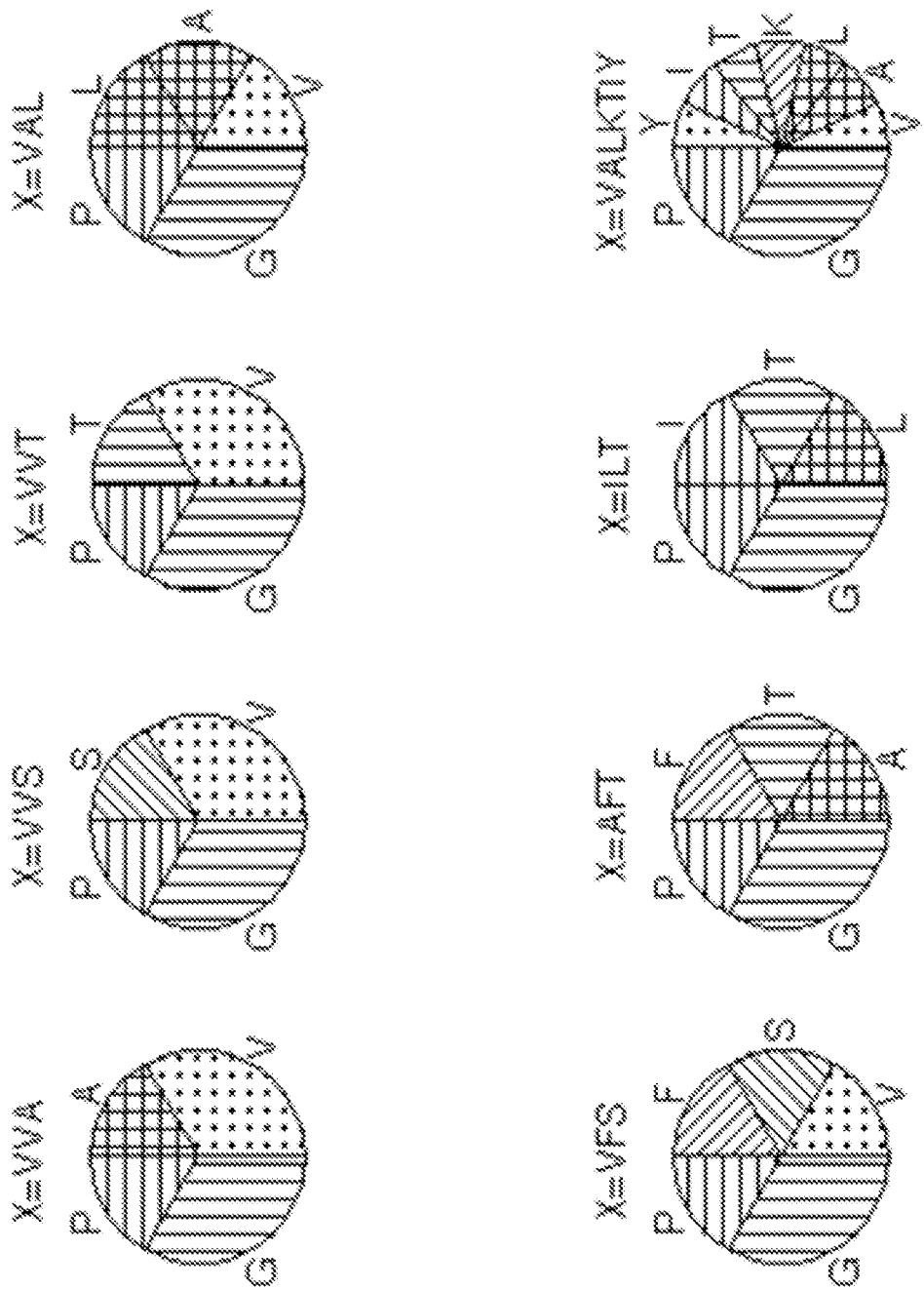
FIG. 2 is a diagram showing the amino acid compositions of exemplary non-repetitive unstructured polypeptides (SEQ ID NOs: 11-18). Each non-repetitive unstructured polypeptide comprises 240 amino acids. Each amino acid sequence comprises approximately ⅙ proline (P) residues, approximately ⅓ glycine (G) residues, and approximately ½ X residues, where X is one or more amino acids selected from the group consisting of valine (V), alanine (A), leucine (L), lysine (K), threonine (T), isoleucine (I), tyrosine (Y), serine (S), and phenylalanine (F). Each of the selected amino acids for X can occur at equal frequencies to each other (SEQ ID NOs: 11-18).
Figure 3A:
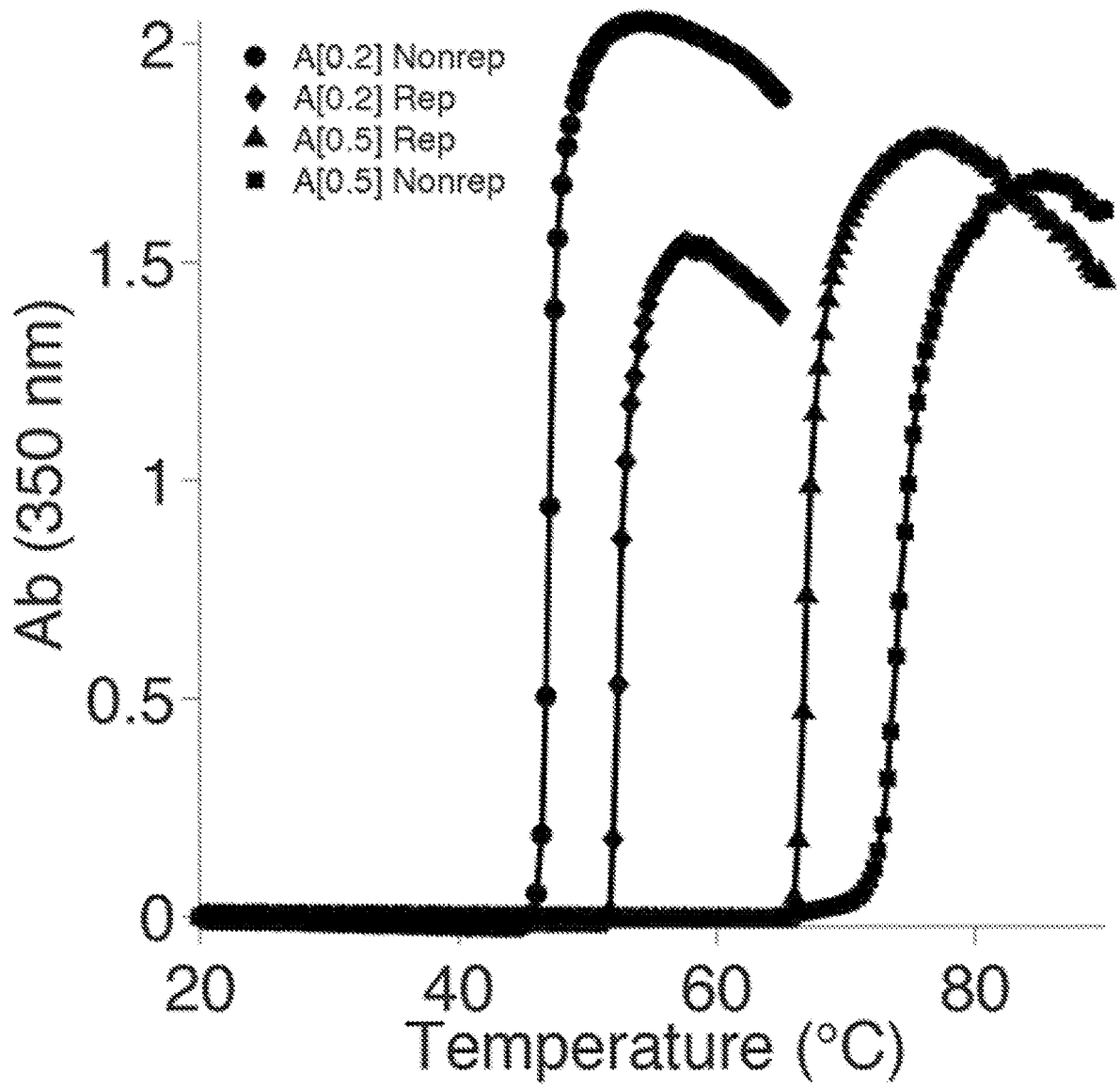
FIG. 3(A)-(B) are graphs showing the characterization of the transition temperatures of the repetitive (SEQ ID NOs: 3-6) and exemplary non-repetitive polypeptides (SEQ ID NOs: 7-10).
Figure 3B:
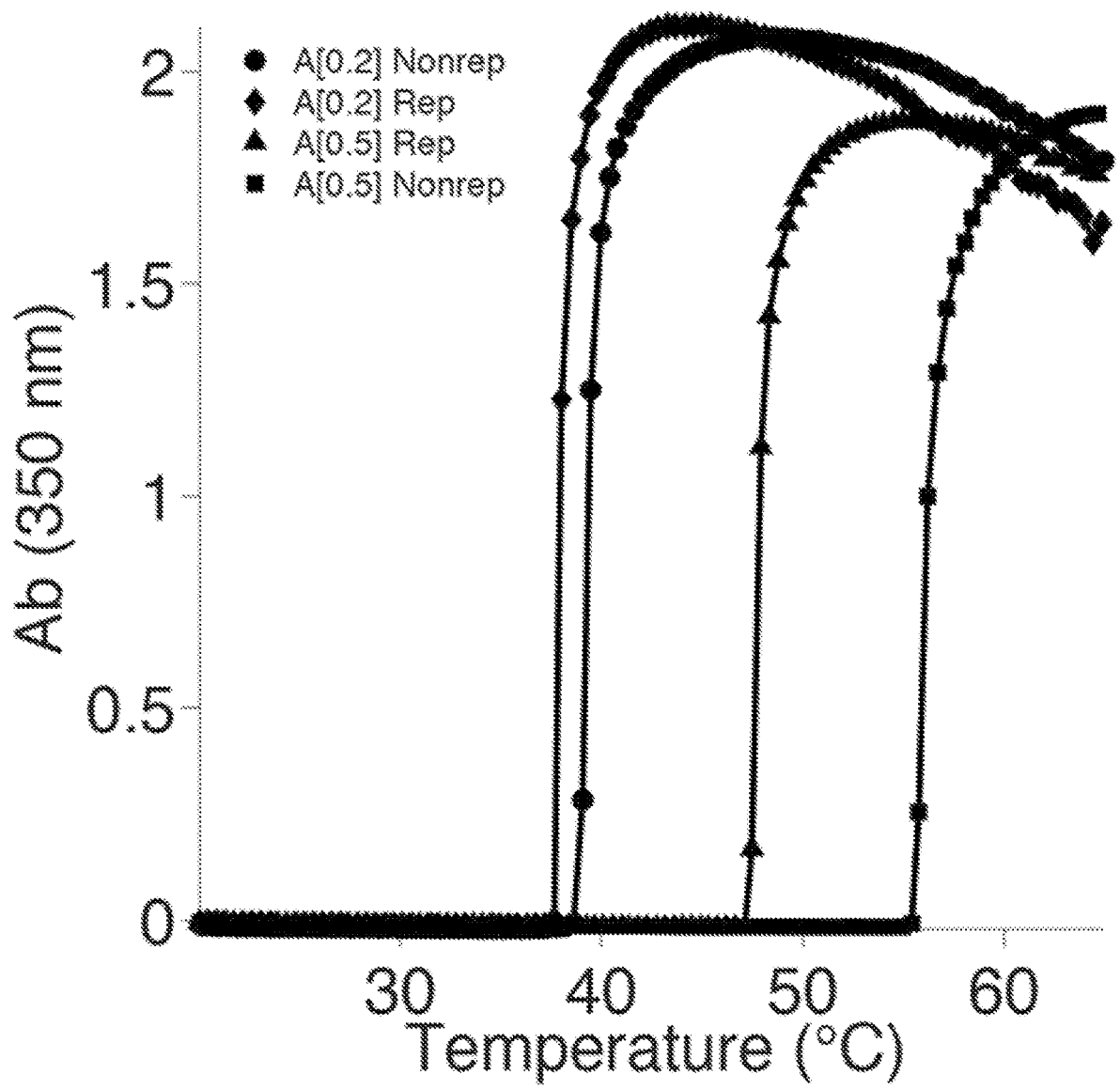
Figure 4A:
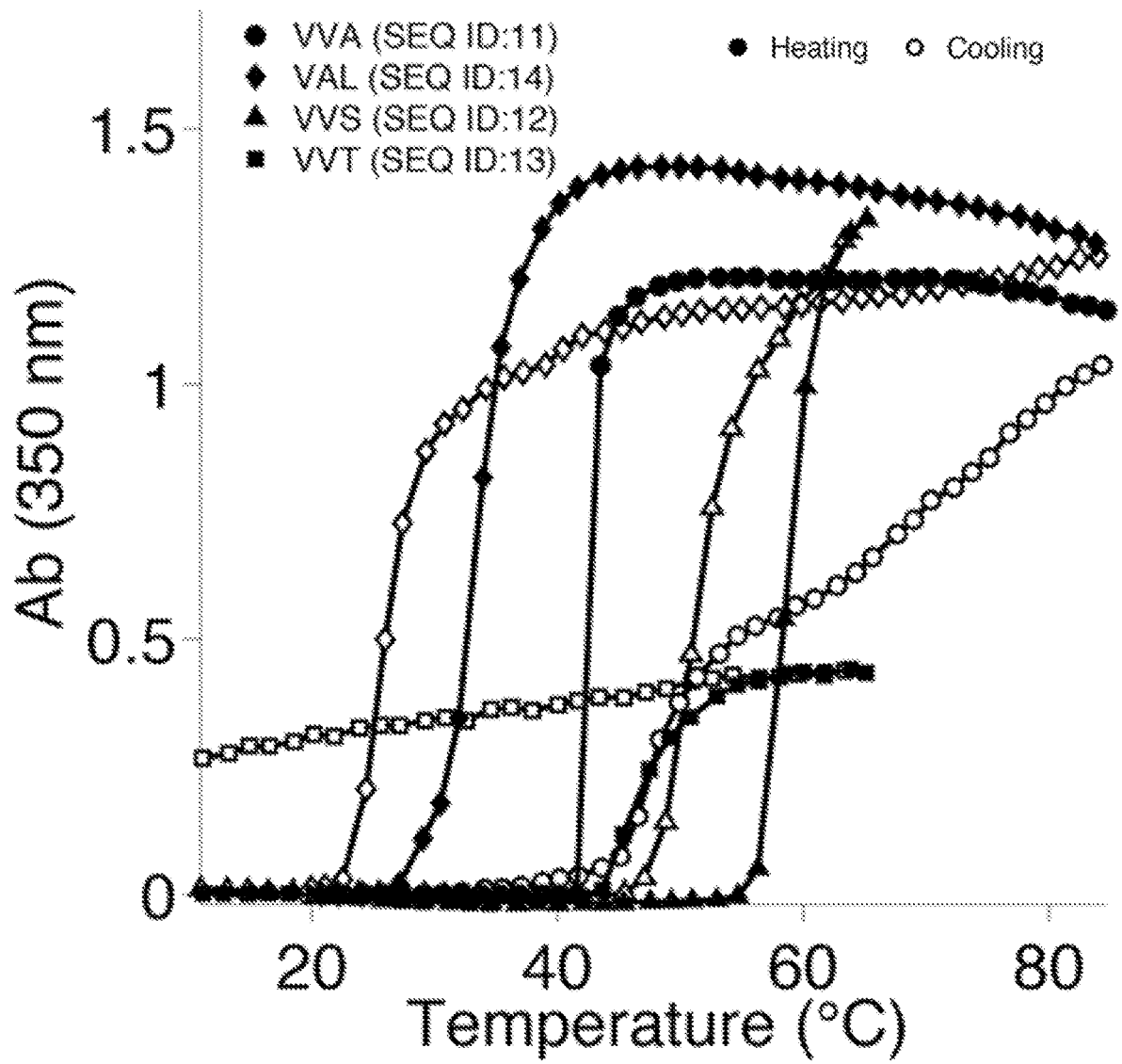
FIG. 4(A)-(B) are graphs showing transition temperature characterization of exemplary non-repetitive unstructured polypeptides (SEQ ID NOs: 11-18).
Figure 4B:
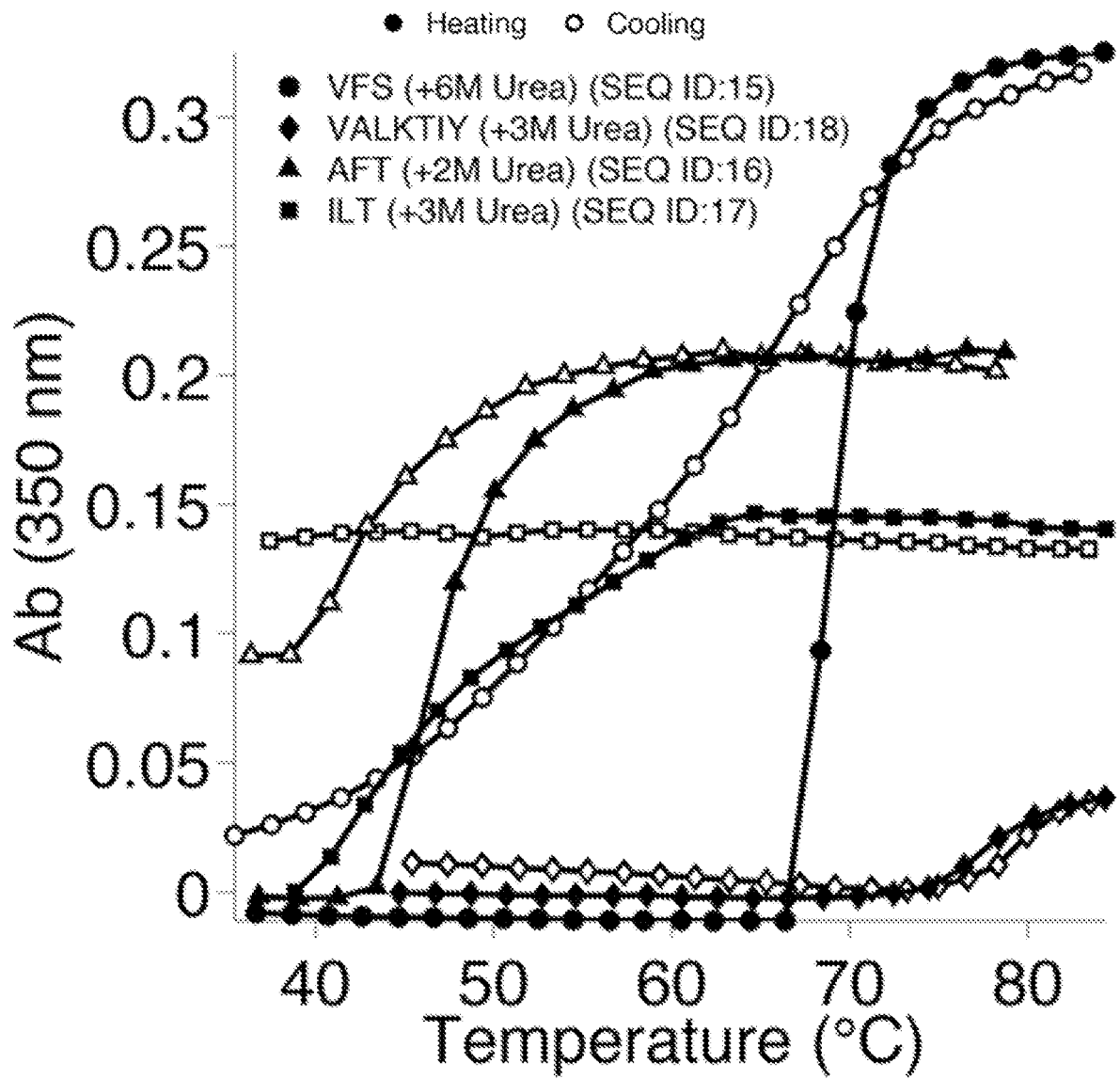

The algorithm was used to additionally identify a panel of 8 non-repetitive sequences, each comprising 240 amino acids with ⅙ being proline (P) and ⅓ being glycine (G). The remaining amino acids were various combinations of 9 different amino acids found in elastin. The amino acid compositions of these sequences are depicted in FIG. 2.

The repetitiveness of each of the unstructured polypeptide sequences was quantified by calculating linguistic complexity scores. Linguistic complexity is defined by the total number of unique subsequences in a given sequence divided by the total number of unique subsequences possible for the same alphabet and window. Scores were calculated using the protein analysis tool, CIDER (see Holehouse et al. (2015) Biophys J., which is incorporated by reference herein in its entirety). The window length was set equal to the total sequence length for each sequence. The final score is given as the product of the linguistic complexity score and total sequence length to account for sequence length. The resulting final scores for the repetitive polypeptide sequences in SEQ ID NOs: 3-6 and non-repetitive polypeptide sequences in SEQ ID NOs: 7-18 are reported in Table 1. All final scores for the non-repetitive polypeptide sequences were greater than 15.0.

TABLE 1

Characterization of the repetitiveness of repetitive (SEQ ID NOs: 3-6) and non-repetitive (SEQ ID NOs: 7-18) polypeptide sequences

| SEQ ID NO | Product of length and linguistic complexity score |
|---|---|
| 3 | 7.9 |
| 4 | 7.9 |
| 5 | 8.0 |
| 6 | 8.0 |
| 7 | 28.7 |
| 8 | 35.6 |
| 9 | 32.8 |
| 10 | 42.8 |
| 11 | 50.6 |
| 12 | 51.6 |
| 13 | 50.6 |
| 14 | 83.3 |
| 15 | 85.3 |
| 16 | 88.3 |
| 17 | 86.3 |
| 18 | 147.8 |

Example 2: Expression of Non-Repetitive Unstructured Polypeptides

All nucleotide sequences, unless indicated, were back-translated from amino acid sequences using codon scrambling (see Tang, N. C. et al. (2016) Nature Mater., which is incorporated by reference herein in its entirety). A N-terminal leader sequence encoding for Met-Ser-Lys-Gly-Pro-Gly (SEQ ID NO: 19) and a C-terminal His-tag tail encoding for Gly-Trp-Pro (SEQ ID NO: 20) were incorporated into the genes, unless indicated. All genes were synthesized by commercial synthesis and cloned into modified pET-24a(+) plasmids (Gen9 Inc., MA, USA and Genscript Inc., NJ, USA). The resulting plasmids were transformed into BL21 competent E. coli cells.

Colonies were inoculated in 2-5 mL of Terrific Broth (TB) plus 50 μg/mL kanamycin and grown overnight at 37° C. and 250 r.p.m. One milliliter of the starter cultures was inoculated in 1 L of TB plus 50 μg/mL kanamycin and grown for 6-7 h at 37° C. and 250 r.p.m. Expression was induced by the addition of IPTG at a final concentration of 1 mM, and the cells were grown for an addition 24 h. The unstructured polypeptides were purified by inverse transition cycling (ITC) as previously described (see Christensen et al. (2009) Curr Protoc Protein Sci., which is incorporated by reference herein in its entirety).

Example 3: Characterization of Non-Repetitive Unstructured Polypeptides

To characterize the inverse transition temperature of unstructured polypeptides, the 350 nm optical densities of 25 μM peptide solutions were monitored with a Cary 300 ultraviolet-visible spectrophotometer (Agilent Technologies) as a function of solution temperature. The inverse transition temperature was also monitored with the SYPRO Orange dye, whose fluorescence increases with the increasing hydrophobicity of the environment. Temperature responsive polymers exhibit phase transition due to the hydrophobic effect in aqueous solutions. Therefore, a StepOnePlus™ Real-Time PCR instrument was used to monitor fluorescence as a function of solution temperature. Inverse transition temperature was defined as the temperature at the maximum of the turbidity or fluorescence gradient.

Turbidity profiles, consisting of heating and cooling curves between about 0° C. and about 100° C., for all constructs at 25 μM in PBS show that non-repetitive versions of A[0.2](SEQ ID NOs: 7 and 9) and A[0.5] (SEQ ID NOs: 8 and 10), retain LCST phase behavior with transition temperatures similar to their repetitive counterparts (SEQ ID NOs: 3 and 5 and SEQ ID NOs: 4 and 6). In addition, the unstructured polypeptides exhibited lower critical solution temperature (LCST) behaviors between 0° C. and 100° C. (see FIG. 3(A)-(B) and FIG. 4(A)-(B)).

SEQUENCES

Repeated subsequences
A[0.5]:

SEQ ID NO: 1

GAGVPGVGVP

A[0.2]:

SEQ ID NO: 2

GVGVPGVGVPGAGVPGVGVPGVGVP

Repetitive polypeptides of A[0.5] and A[0.2]
A[0.2] rep, 200 amino acids:

SEQ ID NO: 3

(GVGVPGVGVPGAGVPGVGVPGVGVP)$_8$

-continued

A[0.5] rep, 200 amino acids:
SEQ ID NO: 4
(GAGVPGVGVP)$_{20}$

A[0.2] rep, 400 amino acids:
SEQ ID NO: 5
(GVGVPGVGVPGAGVPGVGVPGVGVP)$_{16}$

A[0.5] rep, 400 amino acids:
SEQ ID NO: 6
(GAGVPGVGVP)$_{40}$

Non-repetitive polypeptides with permutations of A[0.5] and
A[0.2]
A[0.2] nonrep, 200 amino acids:
SEQ ID NO: 7
PGGGVPGGVPGAVPGVPGAVVPVVGGVPGVVGVPGGVVPVGVVVPGVPVGVPGVPVVGGGVP

AGGVVPGGGVPVGGGVVPGVGVVPGGVPVVVGGGVGVPGVVPGVPGVGVPVGGVPGGGVVV

PGGVGVPVVGVVPGAPGVPGVPGGVGGVPVGVGVPGGGAPGVVPGGAVPGGAPVGGVGGGV

PGVGGVPGAPGGVPGG

A[0.5] nonrep, 200 amino acids:
SEQ ID NO: 8
PGGVPGVPAGGGAGVPGVPGAPAGGGAPGVAPGGVVPGVPGVAPVVGGGAPGGVPGAVPGVP

GGVPGGVVVPGGGVGAPGGVAPVGGGVPVVGGVPVGGVAPGVPVGVPGVGVGVPVGGGV

GGVPGVVPAGVPGGGVAGVVPVGGVINVVGAPGGGVGVPGAPGAGGVPGGAPGAPGVVAPG

GVPVGVVVPGVVPGGG

A[0.2] nonrep, 400 amino acids:
SEQ ID NO: 9
PGGVPGVGGGVPGVPGAPGVVPGVVVPGGVVPVGGVPGVPVVGGGVPVGGGVGGVPGAPGG

GVPGAPVGGVPGGVVPGVGVPGAGGGVPGGVGVVPVGGGAPGGVPGVVPGVPVGGVPAGV

VPGGVGVGGGVVPGVVGVPGGGVGGGVGVPGGAPGGGVVGGGVPGGGVVPVVGGVPGAVP

GVPGVVVPVGGGVVPVGVPGGVVVPGVPGGVGVPVVGVPGVGVVPGVPGVPVGVGVVVPG

VVPVGVGVPGVPGGGVPGVGVPVGGAPGVPGVPGVAVPGVVPGGAPGVPVGVVPGVVPGGG

VGVVPGGVPGGVPGVPAGVPVGVPVGGVGGVVPGGGAPGVGVGVPAGVPGGVPVGVGGVTG

GVVPGVPAGGGVPVGVPGVGGVPVGAPGVPGGVP

A[0.5] nonrep, 400 amino acids:
SEQ ID NO: 10
PAGAVPGGVPVAGGVPVGAGVVAPGAPVGGAPGVVGVPGGGVPGVPVVGVGVGVPVGGGVG

VVPAGGGAPGGVGVVVPGVVPGAPAGGVPGVAPGGVGGVPGVVPGGGVVPGVAPGVPGVPG

GVPVGVPVGAAPGGGVPAVGVPGVGGGVPVVGAGAPGGVPGVAVPGAPGGVPVGGVPGGGV

GGVVPGGVPGAPVGVVPGVGVVPGVRAGVGVPGAPGAPGGGVPGGGAPVGGAGGVPGGVPG

VPGAPGVGVPGVGVPVGVPGVPGVPVGGGAGVPGGVAPGVAVPGGVGVPVVGGVPGAVPGVP

GVGGAPGVPGGGVVGVGVPGGVVPGVPGAGAPGGGAPGAPVGVPGGAPGVVPGVGGVPGAG

GGVVGGGVVPVGGGVVPGAPGGAPVGGVVGGVP

Non-repetitive polypeptides:
Each amino acid sequence comprises $^1/_6$ proline (P) residues,
$^1/_3$ glycine (G) residues, and $^1/_2$ Xresidues, where X is one or
more amino acids selected from the group consisting of valine
(V), alanine (A), leucine (L), lysine (K), threonine (T),
isoleucine (I), tyrosine (Y), serine (S), and phenylalanine
(F). Each of the selected amino acids for X occurs at equal
frequencies to each other.
SEQ ID NO: 11
PVGVPGVGGAPVVVGGAPVGVGGAGGVVPGAPVGAVAGVGAPGGAVPAGGAPGVGAPGVVP

GAVPGVGVGGVGGGVVVVVVVGVGGVPAGAVPVGGVAPVGVPVGAGGGAPAGGVPVAVGV

-continued

PVVGGGVPGVGVVGVAPGAPGAGVGVVAGAGAAAVAPVGVAPGVPGVPGAVVGVPGGVAPA

VVVGAVPGVVGVVPVGAPVVAGGVAVAPVGGAVPGVPGGVPGGGAPGAPVVGVPVGVP

SEQ ID NO: 12
PVGSPGSVPGVVPVSGVVVGGGSVPGSSPVVGVPSGVPVGSPVVGGGVSPGVGVPGVVVGVP

VGGGVGVPGGGVVGGVPVVVGVSVPSGVSPGGGVVVPVGSVSSGVPVVSVVGVSVVPGSVPV

GSPSSGVPGVVPGSPGGVVGSSVPSGSGGVSVPVGVGGSGVPGVPGSGSVVPVGVSPVGGGSG

SGVGSGSPGGSVPGGSPGVVPVGSPGVGGVPGVVGGSGSPGVPGGVGVGVPG

SEQ ID NO: 13
PVGTPGTVPGGVVPVGVTPVGGGTGTPTTVTVVGGVVVPGVPGGGTPGVPVGTPVVGGVGVGT

GTPGGTVPGGTPGVVPGTPGGVVPGTTVPTGTGTTPVVGVPTVGGVTPGVGGVPVVVGTGVPG

VPVGGGVGVVOVVVPGTVPVGVPGVVGGTVPVGTPTTGVPGVVPTGVITGGVGVPGGGVVGG

VVPGVTVPVGTVTTGVPVVTVGVVVPVGTVGGVVVGGGTTPGGVPGTPGVGG

SEQ ID NO: 14
GAVVVPGGAVGVPAGAVGGVGGVLVPAVGAVPGGGVPAVGVPVAGVVPGGLPGGAGVGALG

AAAPGGVPVGAALPGVAGVAPGGGLPGLGAGAGLGLAGALVLPGLGGVPGVPGGGLLPGGVP

LLGLPGVPAGLPGVLPVGLLLPGAPGVPALGVPLGVPGVAPGLPGAGGLPGVGAPCGLLPVGG

APAALGGLGLPGGGALGLLAPGGALVPGVGGVAPVAAGALLPGGAPLGVPALLAL

SEQ ID NO: 15
SSGSSGSGFFSGGVPSGGGVVFVPSFFGFFPSGSGGVVPGVPGGGVGVPGFVGVPVGGFPVGV

PGVFVPSVVGVPGFFVFPGVPGGSSSPGSPFGVFGGGSSGGGFPFGSSPGVVVSPGFGFGVPF

GVPVGGSVFFFPFGGGFPGGFPSGSFGVPGGGFVVPFGVSPGSPGFVPSFGSPGGFGGFSPF

SSGVGSPGGVPGVGVVSPGFPGGSPFGFPGSPGGSFGGSPSVFGSGSPGSFP

SEQ ID NO: 16
AAGGTGFFTGGAPGGTPTAFGGFTPFTFAGGGAPGFFAFPGAPGTFPTFGAPGAAPFGTTPGT

FFGFPGGTPGTPGAATPGFFGAFGFPGAFATFGFPGGGAGAAPAGTPGAPTAAGATTPGAGGT

TGGAPTGGGFAPTFFGFFPTGTGGAAPGAPGGGTTTFPGATPFGFPGGTPGTFGAPGGGFFPG

AGFGGGAPGAPAAAGGGTPGTATPGTFPTGAGTFPGTFPFGGGFPGGFPT

SEQ ID NO: 17
TILPGIGLPGGLPLTIGGILPILLGTTIGGIPGGGIIPGIGGGIPILTILILPTGLPGTPLTT

GTPGITGLGTPLGIGLIGTGIPGGGTGIPTGIPGTTLPGIPTLGGGIPLIGTPGGIGTIGIPG

TGTIIGIPGGGLLLIPGITPLIGLPGGITGTPGGGTGTTPTGLPGILLPGGLPGIPTGTPGTG

TPIGGLLILLTLPGLPGLGLPGLIPLGTGLTGGIPTGGIPGGICHPGILIT

SEQ ID NO: 18
PGTYPGYGYVYPTTGGIPGGVVPGGGTKKLPGKGKGGAKAPGTVPVGAGGGKIVPIYGIAPGK

YGYPGGGIVPGITTPGLPTGKKPYGGVPVLYGKLPGAPGIPTAGAPGYIAPGVPGGLVKGGTG

IAPLGIVILVYIGVGGIKGGALPIGGLYPGAGITGYPVGGGAPAGGIALKPGITPGTAAPGLP

GKGGKYTYPGGAPGGTGGVPGNPGLALKLGIPTKGGGIGLPYIGLLPGKPGG

SEQ ID NO: 19
Met-Ser-Lys-Gly-Pro-Gly

SEQ ID NO: 20
Gly-Trp-Pro

-continued

SEQ ID NO: 21

(Gly$_4$Ser)$_3$

SEQ ID NO: 22

PQPQPKKPQPKPEPEPQPQG

SEQ ID NO: 23

(VPGXG)$_n$, wherein X is any amino acid except proline and n is an integer greater than or equal to 1

What is claimed is:

1. An unstructured polypeptide having a lower critical solution temperature (LCST), an upper critical solution temperature (UCST), or a combination thereof,
   wherein the unstructured polypeptide lacks a serial pentapeptide repeat of an elastin-like polypeptide (ELP), wherein the ELP repeat has the sequence (VPGXG)$_n$, where n is an integer greater than 1 and X is any amino acid except proline,
   wherein the unstructured polypeptide has a linguistic complexity score, and wherein the product of the linguistic complexity score and the amino acid sequence length of the unstructured polypeptide is greater than 15;
   wherein the polypeptide comprises a sequence of at least 50 amino acids, wherein at least 10% of the amino acids are proline (P), and wherein at least 20% of the amino acids are glycine (G),
   wherein the polypeptide phase transitions above the LCST, phase transitions below the UCST, or a combination thereof, and
   wherein the LOST and the UCST are each independently from about 0° C. to about 100° C.

2. The unstructured polypeptide of claim 1, wherein the LCST and UCST are each independently from about 25° C. to about 37° C.

3. The unstructured polypeptide of claim 1, wherein the unstructured polypeptide comprises:
   (a) a sequence wherein at least 40% of the amino acids are selected from the group consisting of valine (V), alanine (A), leucine (L), lysine (K), threonine (T), isoleucine (I), tyrosine (Y), serine (S), and phenylalanine (F);
   (b) a 50 amino acid subsequence of any of SEQ ID NO: 7-18;
   (c) a sequence that does not contain three contiguous identical amino acids,
   wherein any 5-10 amino acid subsequence does not occur more than once in the unstructured polypeptide, and wherein when the unstructured polypeptide comprises a subsequence starting and ending with proline (P), the subsequence further comprises at least one glycine (G);
  (d) a sequence of at least 50 amino acids,
    wherein at least 10% of the amino acids are proline (P),
    wherein at least 20% of the amino acids are glycine (G),
    wherein at least 40% of the amino acids are selected from the group consisting of valine (V), alanine (A), leucine (L), lysine (K), threonine (T), isoleucine (I), tyrosine (Y), serine (S), and phenylalanine (F),
    wherein the sequence does not contain three contiguous identical amino acids,
    wherein any 5-10 amino acid subsequence does not occur more than once in the unstructured polypeptide, and
    wherein when the unstructured polypeptide comprises a subsequence starting and ending with proline (P), the subsequence further comprises at least one glycine (G) or
  (e) an amino acid sequence selected from SEQ ID NOs: 7-18.

4. A fusion protein comprising at least one binding polypeptide and at least one unstructured polypeptide of claim 1.

5. The fusion protein of claim 4, wherein the fusion protein comprises a plurality of unstructured polypeptides.

6. The fusion protein of claim 4, wherein the fusion protein comprises a plurality of binding polypeptides.

7. The fusion protein of claim 6, further comprising a linker positioned between at least two adjacent binding polypeptides.

8. The fusion protein of claim 5, further comprising a linker positioned between at least two adjacent unstructured polypeptides.

9. The fusion protein of claim 7, wherein the linker comprises:
  (a) at least one glycine and at least one serine, preferably wherein the linker comprises an amino acid sequence consisting of SEQ ID NO: 21 ((Gly$_4$Ser)$_3$); or
  (b) an amino acid sequence consisting of SEQ ID NO: 22 (PQPQPKPQPKPEPEPQPQG).

10. The fusion protein of claim 8, wherein the linker comprises:
  (a) at least one glycine and at least one serine, preferably wherein the linker comprises an amino acid sequence consisting of SEQ ID NO: 21 ((Gly$_4$Ser)$_3$); or
  (b) an amino acid sequence consisting of SEQ ID NO: 22 (PQPQPKPQPKPEPEPQPQG).

11. The fusion protein of claim 6, wherein the plurality of binding polypeptides forms an oligomer.

12. The fusion protein of claim 4, wherein the binding polypeptide binds a target, and wherein the fusion protein binds more than one target, and/or wherein the binding polypeptide comprises Protein A.

13. The fusion protein of claim 4, further comprising at least one linker positioned between the at least one binding polypeptide and the at least one unstructured polypeptide, preferably wherein the fusion protein comprises a plurality of linkers between the at least one binding polypeptide and the at least one unstructured polypeptide.

14. The fusion protein of claim 4, wherein the at least one binding polypeptide is positioned a) N-terminal to the at least one unstructured polypeptide or b) C-terminal to the at least one unstructured polypeptide.

\* \* \* \* \*